(12) United States Patent
Loiseleur et al.

(10) Patent No.: US 8,658,801 B2
(45) Date of Patent: Feb. 25, 2014

(54) PESTICIDES CONTAINING A BICYCLIC BISAMIDE STRUCTURE

(75) Inventors: Olivier Loiseleur, Stein (CH); Patricia Durieux, Allschwil (CH); Stephan Trah, Stein (CH); Andrew Edmunds, Stein (CH); André Jeanguenat, Stein (CH); André Stoller, Stein (CH); David John Hughes, Bracknell (GB)

(73) Assignees: Syngenta Crop Protection, LLC, Greensboro, NC (US); Syngenta Limited, Guildford, Surrey (GB)

( * ) Notice: Subject to any disclaimer, the term of this patent is extended or adjusted under 35 U.S.C. 154(b) by 523 days.

(21) Appl. No.: 12/278,807

(22) PCT Filed: Feb. 14, 2007

(86) PCT No.: PCT/EP2007/001283
§ 371 (c)(1),
(2), (4) Date: May 15, 2009

(87) PCT Pub. No.: WO2007/093402
PCT Pub. Date: Aug. 23, 2007

(65) Prior Publication Data
US 2009/0298816 A1   Dec. 3, 2009

(30) Foreign Application Priority Data
Feb. 16, 2006 (EP) .................................... 06003094

(51) Int. Cl.
*C07D 401/14* (2006.01)
(52) U.S. Cl.
CPC .................................... *C07D 401/14* (2013.01)
USPC .................................................... 546/275.7

(58) Field of Classification Search
CPC ...................................................... C07D 401/14
USPC ........................................................ 546/275.7
See application file for complete search history.

(56) References Cited

FOREIGN PATENT DOCUMENTS

WO   2005085234        9/2005
WO   WO 2005085234 A2 * 9/2005

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

* cited by examiner

*Primary Examiner* — Joseph Kosack
*Assistant Examiner* — Matthew Coughlin
(74) *Attorney, Agent, or Firm* — R. Kody Jones

(57) ABSTRACT

Compounds of formula (I), wherein the substituents are as defined in claim 1, and the agrochemically acceptable salts and all stereoisomers and tautomeric forms of the compounds of formula I can be used as agrochemical active ingredients and can be prepared in a manner known per se.

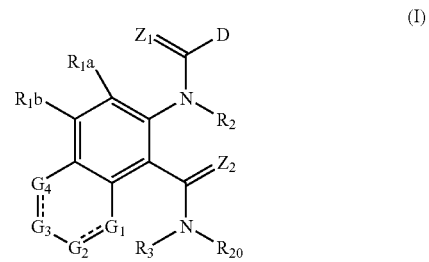

15 Claims, No Drawings

PESTICIDES CONTAINING A BICYCLIC BISAMIDE STRUCTURE

This application is a 371 of International Application No. PCT/EP2007/001283 filed Feb. 14, 2007, the contents of which are incorporated herein by reference, and which claims priority to EP 06003094.7 filed Feb. 16, 2006.

The present invention relates to bicyclic bisamide derivatives, to processes for their preparation, to compositions comprising those compounds, and to their use for controlling insects or representatives of the order Acarina.

Bisamide derivatives with insecticidal action are known and described, for example, in US 2003/0229050 and WO 2005/085234.

There have now been found novel bicyclic bisamide derivatives with pesticidal properties. The present invention accordingly relates to compounds of formula I

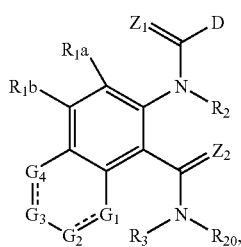

(I)

wherein $G_1$, $G_2$, $G_3$ and $G_4$ form together with the two carbon atoms to which $G_1$ and $G_4$ are attached, an aromatic ring system; wherein $G_1$ is nitrogen, sulfur, oxygen, a direct bond or C—$R_{5a}$;
$G_2$ is nitrogen, sulfur, oxygen, a direct bond or C—$R_{5b}$;
$G_3$ is nitrogen, sulfur, oxygen, a direct bond or C—$R_{5c}$;
$G_4$ is nitrogen, sulfur, oxygen, a direct bond or C—$R_{5d}$;
with the provisos that a) at least one substituent G represents nitrogen, sulfur or oxygen, b) not more than 1 substituent G can at the same time form a direct bond, c) not more than 2 substituents G can be oxygen or sulfur, and d) 2 substituents G as oxygen and/or sulfur are separated by at least one carbon atom; each of $R_{1a}$, $R_{1b}$, $R_{5a}$, $R_{5b}$, $R_{5c}$, and $R_{5d}$ which may be the same or different, represents hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_r$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, $C_3$-$C_6$trialkylsilyl, phenyl, benzyl or phenoxy; or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_8$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl;

each of $R_2$ and $R_3$, which may be the same or different, represents hydrogen, $C_1$-$C_6$alkyl, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_8$cycloalkyl substituted by one or more substituents selected from halogen nitro, cyano, hydroxy, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino and $C_1$-$C_6$alkyl-$C_3$-$C_6$cycloalkylamino;

D is 2-pyridyl, 3-pyridyl or 4-pyridyl; or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl; or D is a group

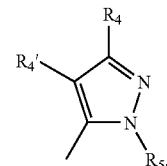

(D$_1$)

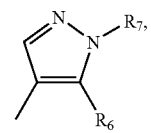

(D$_2$)

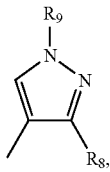

(D$_3$)

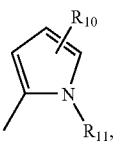

(D$_4$)

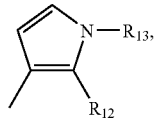

(D$_5$)

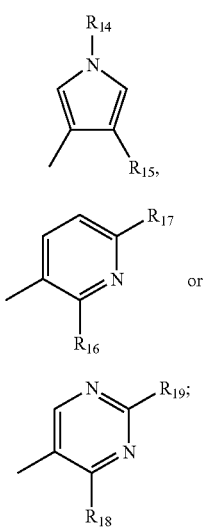

or D is additionally phenyl if $Z_1$ is sulfur;

$R_4$, $R_4'$, $R_{10}$, $R_{17}$, and $R_{19}$ independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_5$, $R_6$, $R_8$, $R_{11}$, $R_{12}$, $R_{15}$, $R_{16}$ and $R_{18}$ independently from each other, are $C_1$-$C_6$alkyl, or $C_1$-$C_6$alkyl mono-, di- or trisubstituted by halogen, cyano, nitro, hydroxy, $C_1$-$C_4$alkoxy, $C_2$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylamino, $C_2$-$C_4$dialkylamino or $C_3$-$C_6$cycloalkylamino; or are phenyl, 2-pyridyl, 3-pyridyl, 4-pyridyl; or are phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_7$, $R_9$, $R_{13}$ and $R_{14}$ independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl;

$R_{20}$ is hydrogen, $C_1$-$C_6$alkyl, $C_2$-$C_6$alkenyl, $C_2$-$C_6$alkynyl, or $C_3$-$C_6$cycloalkyl; or is $C_1$-$C_6$alkyl, $C_2$-$C_6$ alkenyl, $C_2$-$C_6$ alkynyl or $C_3$-$C_6$ cycloalkyl substituted with one, two or three substituents selected from the group consisting of halogen, cyano, nitro, hydroxy, $C_1$-$C_4$alkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_6$ alkoxycarbonyl, $C_2$-$C_6$ alkylcarbonyl, $C_2$-$C_6$trialkylsilyl, benzyl, phenoxy and a three- to ten-membered, monocyclic or fused bicyclic ring system which may be aromatic, partially saturated or fully saturated, wherein the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl;

it being possible for said three- to ten-membered, monocyclic or fused bicyclic ring system to be spiro-bonded to the $C_3$-$C_6$cycloalkyl group;

or $R_{20}$ is $C_1$-$C_4$alkoxy, $C_1$-$C_4$alkylamino, $C_2$-$C_8$dialkylamino, $C_2$-$C_6$ cycloalkylamino, $C_2$-$C_6$alkoxycarbonyl or $C_2$-$C_6$alkylcarbonyl;

or $R_{20}$ is 3-oxetanyl, 3-thietanyl, 1-oxo-3-thietanyl, 1,1-dioxo-3-thietanyl, 1-imino-1-oxo-3-thietanyl, 3-azetdinyl, each optionally substituted with one to five substituents independently selected from $C_1$-$C_4$ alkyl, $C_1$-$C_4$ haloalkyl, halogen, cyano; each of $Z_1$ and $Z_2$, which may be the same or different, represents oxygen or sulfur;

and agronomically acceptable salts/isomers/enantiomers/tautomers/N-oxides of those compounds.

Compounds I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Where appropriate, the corresponding internal salts can furthermore be formed. Preferred within the scope of the invention are agrochemically advantageous salts; however, the invention also encompasses salts which have disadvantage for agrochemical use, for example salts which are toxic to bees or fish, and which are employed, for example, for the isolation or purification of free compounds I or agrochemically utilizable salts thereof. Owing to the close relationship between the compounds I in free form and in the form of their salts, for the purposes of the invention the free compounds I or their salts hereinabove and hereinbelow are respectively to be understood as including, where appropriate, the corresponding salts or the free compounds I. The same applies analogously to tautomers of compounds I and salts thereof. In general, the free form is preferred in each case.

The alkyl groups occurring in the definitions of the substituents can be straight-chain or branched and are, for example, methyl, ethyl, n-propyl, isopropyl, n-butyl, sec-butyl, isobutyl, tert-butyl, pentyl and hexyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_3$-$C_{20}$alkenyl groups which are mono-, di- or trisubstituted by halogen, preference is given to those having a chain length of from 3 to 5 carbon atoms.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl. Among the alkynyl groups which are mono- or polysubstituted by halogen, preference is given to those having a chain length of from 3 to 5 carbon atoms.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tertbutoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms. Alkylthio is, for example, methylthio, ethylthio, propylthio, isopropylthio, n-butylthio, isobutylthio, sec-butylthio or tertbutylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

According to the present invention, a three- to ten-membered monocyclic or fused bicyclic ring system which may be aromatic, partially saturated or fully saturated is, depending of the number of ring members, for example, selected from the group consisting of

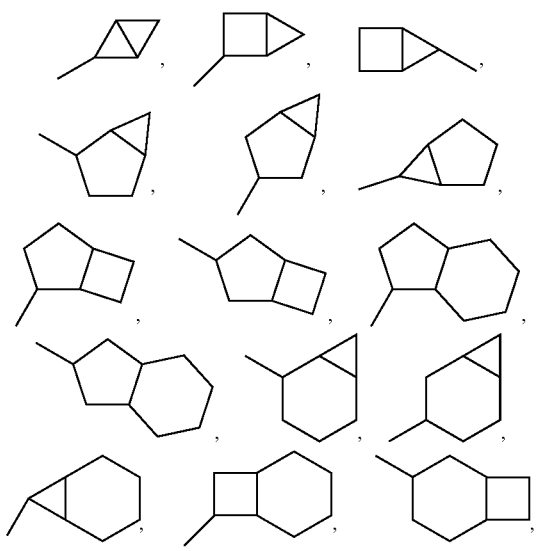

cyclopropyl, cyclobutyl, cyclopentyl, cyclohexyl, where said cycloalkylgroups for their part may be preferably unsubstituted or substituted by $C_1$-$C_6$alkyl or halogen, or is naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4- triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

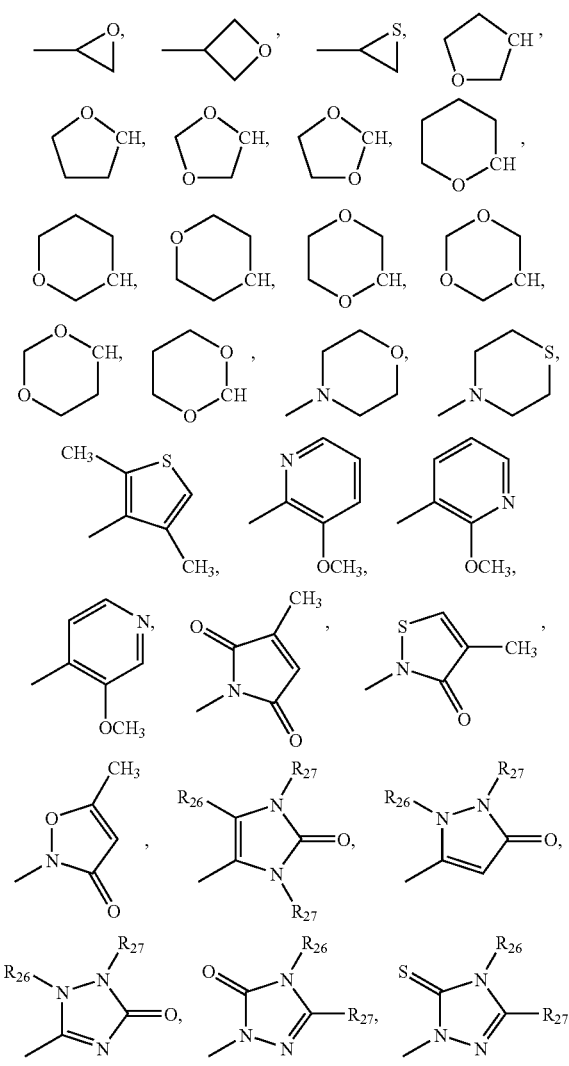

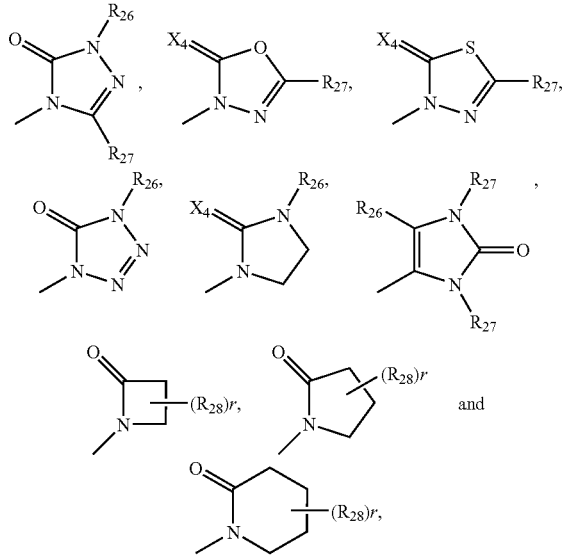

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r is 1, 2, 3 or 4.

Examples for a three- to ten-membered, monocyclic or fused bicyclic ring system which is spiro-bonded to the $C_3$-$C_6$cycloalkyl group of the substituent $R_{20}$ are

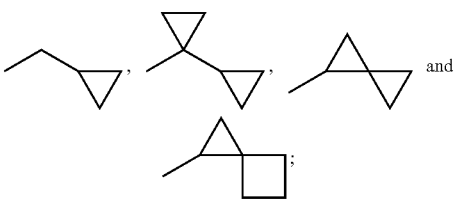

Where no free valency is indicated in those definitions, for example as in

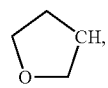

the linkage site is located at the carbon atom labelled "CH" or in a case such as, for example,

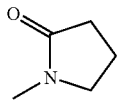

at the bonding site indicated at the bottom left.

Preferably $Z_1$ and/or $Z_2$ is oxygen.
Preferably $R_4$ is hydrogen.
Further compounds of formula I are preferred, wherein $R_2$ and/or $R_3$ is hydrogen.

$R_{20}$ is preferably hydrogen, methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)CH_3$, $C(CH_3)_2CH_2S(O)_2CH_3$, CH$_2$CN, CH(CH$_3$)CH$_3$SCH$_3$, CH(CH$_3$)CH$_3$S(O)CH$_3$ or CH(CH$_3$)CH$_3$S(O)$_2$CH$_3$, 3-methyl-thietan-3-yl, 1-oxo-3-methyl-thietan-3-yl or 1,1-dioxo-3-methyl-thietan-3-yl, in particular hydrogen, methyl, ethyl, i-propyl, tert.-butyl, CH$_2$—C$_3$H$_5$, C(CH$_2$CH$_2$)—C$_3$H$_5$, C(CH$_3$)$_2$CH$_2$SCH$_3$, C(CH$_3$)$_2$CH$_2$S(O)CH$_3$, C(CH$_3$)$_2$CH$_2$S(O)$_2$CH$_3$, CH$_2$CN, CH(CH$_3$)CH$_3$SCH$_3$, CH(CH$_3$)CH$_3$S(O)CH$_3$ or CH(CH$_3$)CH$_3$S(O)$_2$CH$_3$.

Special emphasis should also be given to compounds of formula I wherein D is a group D$_1$, wherein R$_5$ is 2-pyridyl which can be substituted by halogen, preferably which is monosubstituted by chloro at the 3-position of the pyridine ring and R$_4$ is halogen preferably chloro or bromo, C$_1$-C$_6$haloalkyl, C$_1$-C$_4$haloalkoxy most preferably OCF$_2$H or 2,2,2-trifluoroethoxy, preferably C$_1$-C$_6$haloalkyl, most preferably trifluoromethyl.

Special mention should be made of compounds of formula I wherein
each of R$_{1a}$, R$_{1b}$, R$_{5a}$, R$_{5b}$, R$_{5c}$, and R$_{5d}$ which may be the same or different, represents hydrogen, halogen, cyano, hydroxy, CHO, C$_1$-C$_6$alkyl, C$_3$-C$_6$cycloalkyl, C$_1$-C$_6$haloalkyl, C$_1$-C$_4$alkoxy, C$_1$-C$_4$alkoxy-C$_1$-C$_4$alkoxy-C$_1$-C$_4$alkyl, C$_1$-C$_4$alkylthio, C$_1$-C$_4$alkylsulfinyl, C$_1$-C$_4$alkylsulfonyl, C$_1$-C$_4$alkylsulfonyl-C$_1$-C$_4$alkyl, C$_1$-C$_4$alkylsulfoximino-C$_1$-C$_4$alkyl, C$_2$-C$_4$dialkylamino or C$_1$-C$_4$alkoxyimino-C$_1$-C$_4$alkyl.

An outstanding group of compounds of formula I is represented by the formula Ib (Ib)

[structure]

wherein G$_1$, G$_2$, G$_3$ and G$_4$ have the meaning as given for formula I above;

R$_{101}$ is halogen, haloalkyl, haloalkoxy, alkoxy, especially difluoromethyl, trifluoromethyl, chlorine, bromine, OCF$_2$H$_2$O—CH$_2$—CF$_3$ or OCH$_3$, in particular halogen, haloalkyl, haloalkoxy, especially trifluoromethyl, chlorine, bromine, OCF$_2$H or O—CH$_2$—CF$_3$;

R$_{102}$ is halogen, C$_1$-C$_6$-alkyl, C$_2$-C$_6$-alkynyl, cyano, especially methyl, ethynyl, chlorine or bromine; in particular halogen, C$_1$-C$_6$-alkyl, especially methyl, chlorine or bromine; and R$_{103}$ is methyl, ethyl, i-propyl, tert.-butyl, CH$_2$—C$_3$H$_5$, C(CH$_2$CH$_2$)—C$_3$H$_6$, C(CH$_3$)$_2$CH$_2$SCH$_3$, C(CH$_3$)$_2$CH$_2$S(O)CH$_3$ or C(CH$_3$)$_2$CH$_2$S(O)$_2$CH$_3$, CH$_2$CN, CH(CH$_3$)CH$_3$SCH$_3$, CH(CH$_3$)CH$_3$S(O)CH$_3$ or CH(CH$_3$)CH$_3$S(O)$_2$CH$_3$, 3-methyl-thietan-3-yl, 1-oxo-3-methyl-thietan-3-yl or 1,1-dioxo-3-methyl-thietan-3-yl; in particular methyl, ethyl, i-propyl, tert.-butyl, CH$_2$—C$_3$H$_5$, C(CH$_2$CH$_2$)—C$_3$H$_5$, C(CH$_3$)$_2$CH$_2$SCH$_3$, C(CH$_3$)$_2$CH$_2$S(O)CH$_3$ or C(CH$_3$)$_2$CH$_2$S(O)$_2$CH$_3$, CH$_2$CN, CH(CH$_3$)CH$_3$SCH$_3$, CH(CH$_3$)CH$_3$S(O)CH$_3$ or CH(CH$_3$)CH$_3$S(O)$_2$CH$_3$.

Especially preferred compounds of formula I are represented by the following formulae:

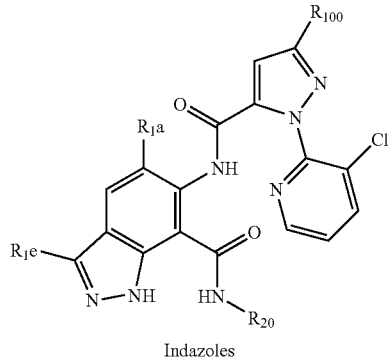

Indazoles (Ic)

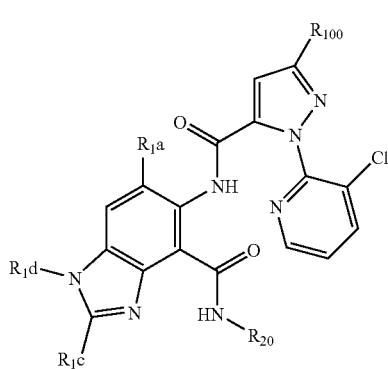

Benzoimidazoles (Id)

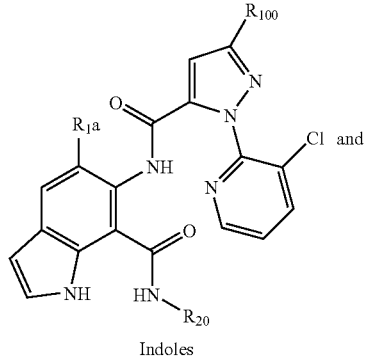

Indoles (Ie)

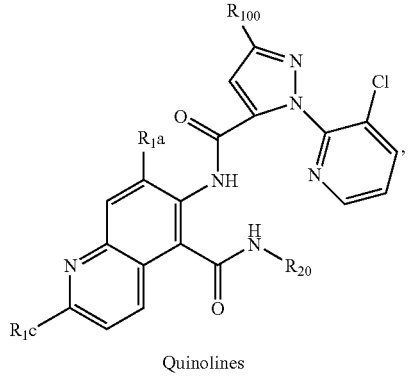

Quinolines (If)

in particular formula (Ic);
wherein
R$_{1a}$ is preferably hydrogen, C$_1$-C$_4$alkyl, C$_2$-C$_4$alkynyl, halogen or cyano;

$R_{20}$ is preferably hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl, thiethan-3-yl, thiethan-3-yl substituted by $C_1$-$C_4$alkyl, preferably 3-methyl-thietan-3-yl,

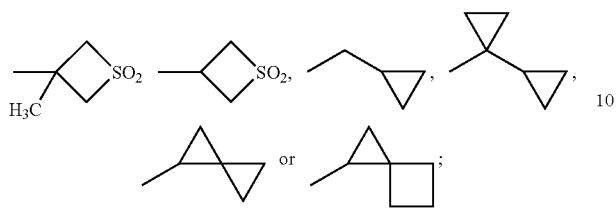

in particular hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl,

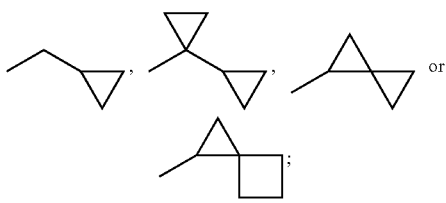

$R_{100}$ is preferably halogen, $C_1$-$C_6$alkyl, $C_1$-$C_6$haloalkyl, $C_1$-$C_6$alkoxy or $C_1$-$C_6$haloalkoxy; in particular halogen, $C_1$-$C_6$alkyl, $C_1$-$C_6$haloalkyl or $C_1$-$C_6$haloalkoxy;

$R_{1c}$ is hydrogen, $CH_3$, $CH_2CH_3$, $OCH_3$, $SCH_3$, Cl, O, $NH_2$, Br, $NHCH_3$ or $N(CH_3)_2$;

$R_{1d}$ is hydrogen or $CH_3$; in particular $CH_3$; and $R_{1e}$ is hydrogen, halogen or $CH_3$; preferably hydrogen.

Further preferred embodiments of the present invention are the embodiments E1 to E99, which are defined as compounds of formula I which are represented by one formula selected from the group consisting of the formulae T1 to T99 as described below, wherein in formulae T1 to T99

$R_{1a}$ is preferably hydrogen, $C_1$-$C_4$alkyl, $C_2$-$C_4$alkynyl, halogen or cyano; in particular chloro or methyl;

$R_{20}$ is preferably hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl, thiethan-3-yl, thiethan-3-yl substituted by $C_1$-$C_4$alkyl, preferably 3-methyl-thietan-3-yl,

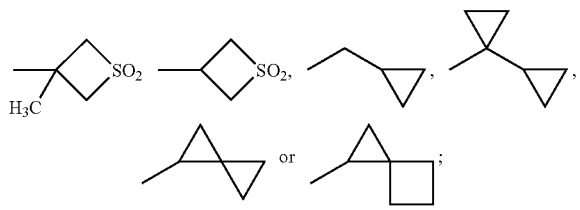

in particular hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl,

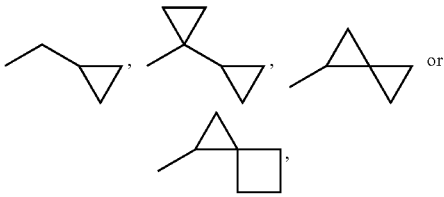

especially isopropyl; and $R_{100}$ is preferably halogen, $C_1$-$C_6$alkyl, $C_1$-$C_6$haloalkyl, $C_1$-$C_6$alkoxy or $C_1$-$C_6$haloalkoxy; in particular halogen, $C_1$-$C_6$alkyl, $C_1$-$C_6$haloalkyl or $C_1$-$C_6$alkoxy; in particular trifluoromethyl, difluoromethyl, methoxy, bromo, chloro or 2,2,2-trifluoroethoxy.

For example, embodiment E1 is represented by the compounds of formula T1

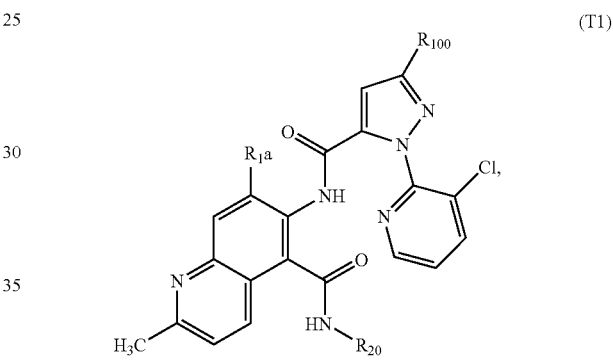

(T1)

wherein $R_{1a}$ is preferably hydrogen, $C_1$-$C_4$alkyl, $C_2$-$C_4$alkynyl, halogen or cyano; in particular chloro or methyl;

$R_{20}$ is preferably hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl, thiethan-3-yl, thiethan-3-yl substituted by $C_1$-$C_4$alkyl, preferably 3-methyl-thietan-3-yl,

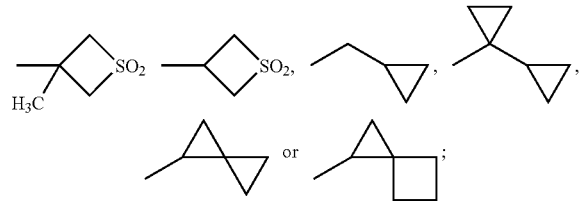

in particular hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl,

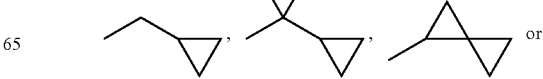

-continued

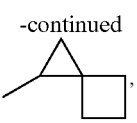

especially isopropyl; and $R_{100}$ is preferably halogen, $C_1$-$C_6$alkyl, $C_1$-$C_6$haloalkyl, $C_1$-$C_6$alkoxy or $C_1$-$C_6$haloalkoxy; in particular halogen, $C_1$-$C_6$alkyl, $C_1$-$C_6$haloalkyl or $C_1$-$C_6$alkoxy; in particular trifluoromethyl, difluoromethyl, methoxy, bromo, chloro or 2,2,2-trifluoroethoxy.

Embodiments E2 to E99 are defined accordingly.

The process according to the invention for preparing compounds of the formula I is carried out analogously to known processes, for example as described in described, for example, in US 2003/0229050 and WO 2005/085234.

The general preparation of the compounds of formula I is illustrated in the following reaction schemes:

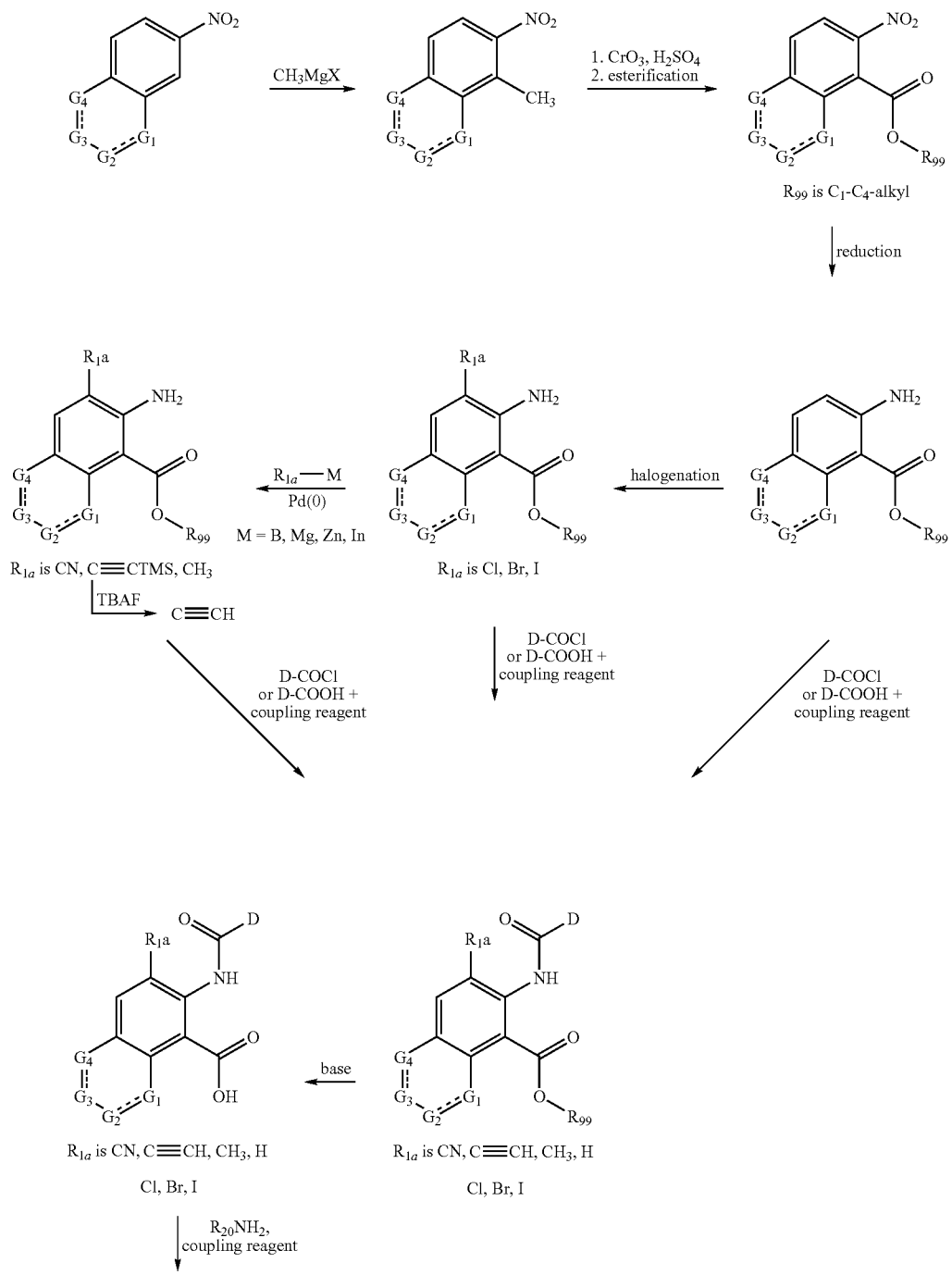

Reaction Scheme 1: Preparation of Compounds of Formula I:

-continued
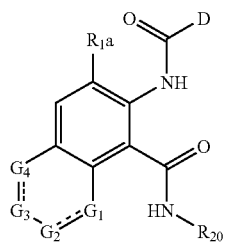
Reaction Scheme 2: Preparation of Compounds of Formula I:
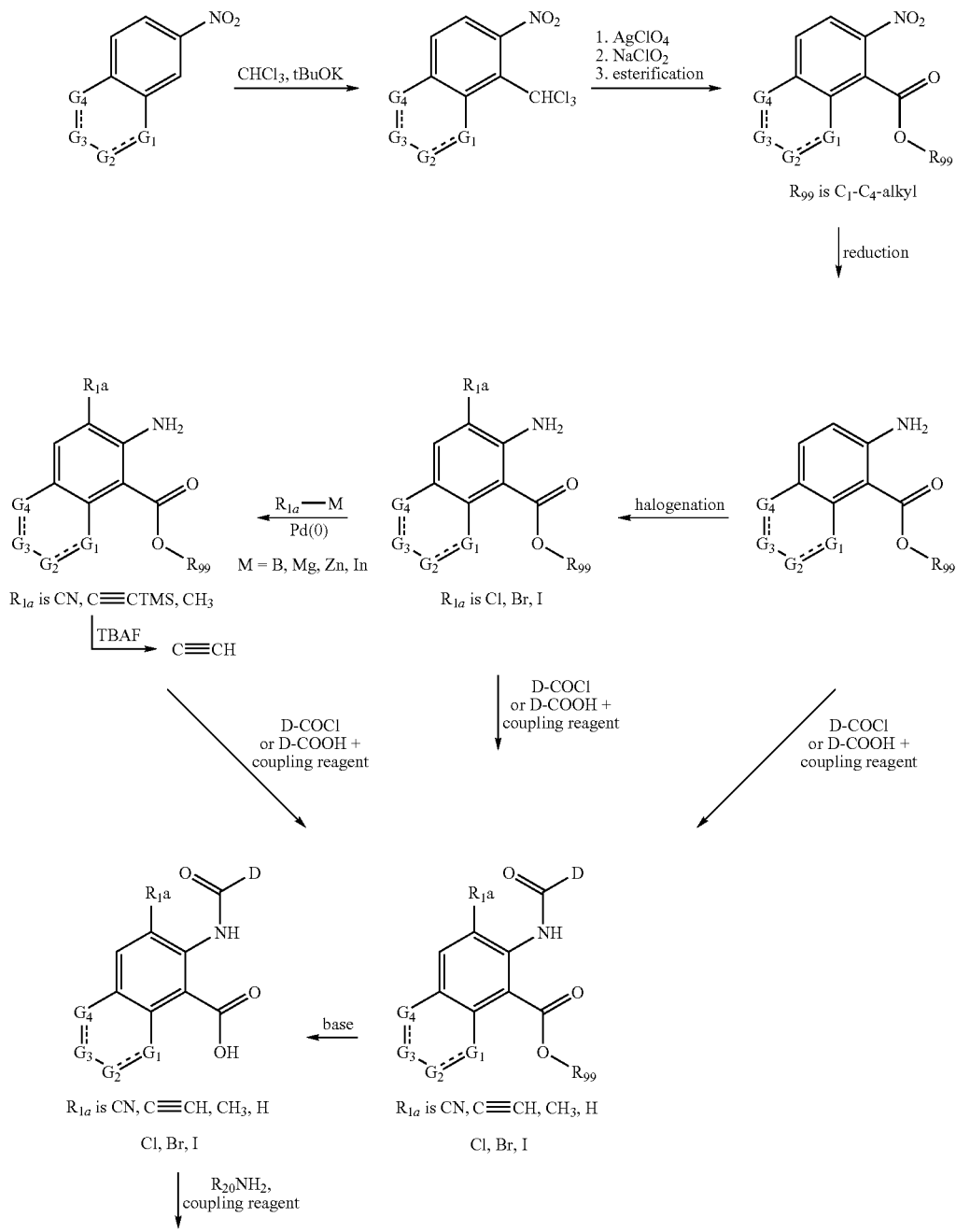

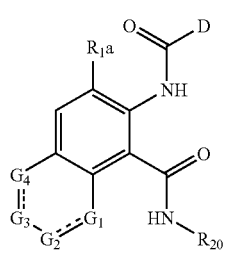
-continued
Reaction Scheme 3: Preparation of Compounds of Formula I:
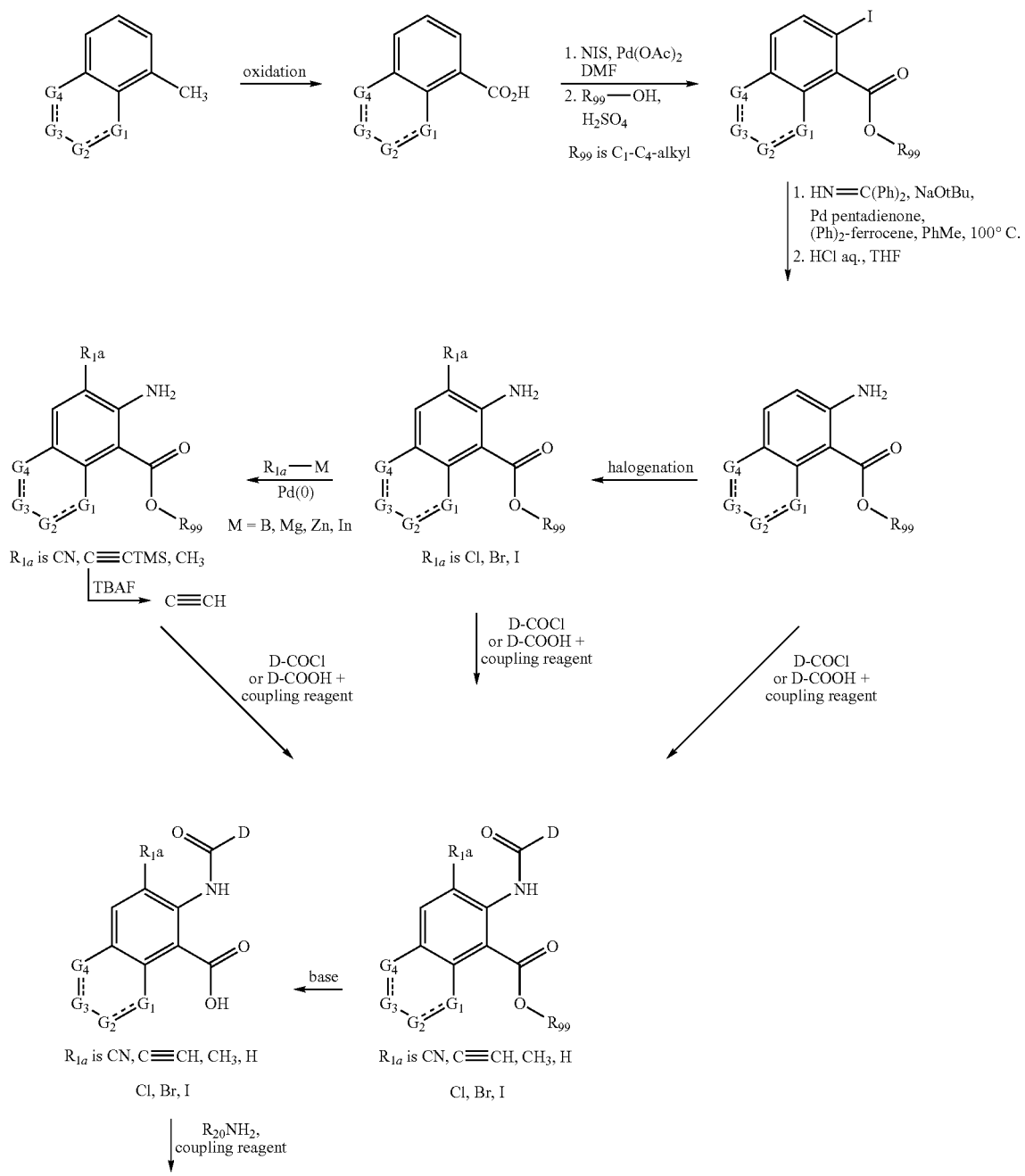

-continued
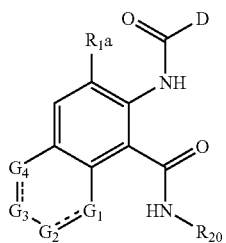
Reaction Scheme 4: Preparation of Compounds of Formula I:
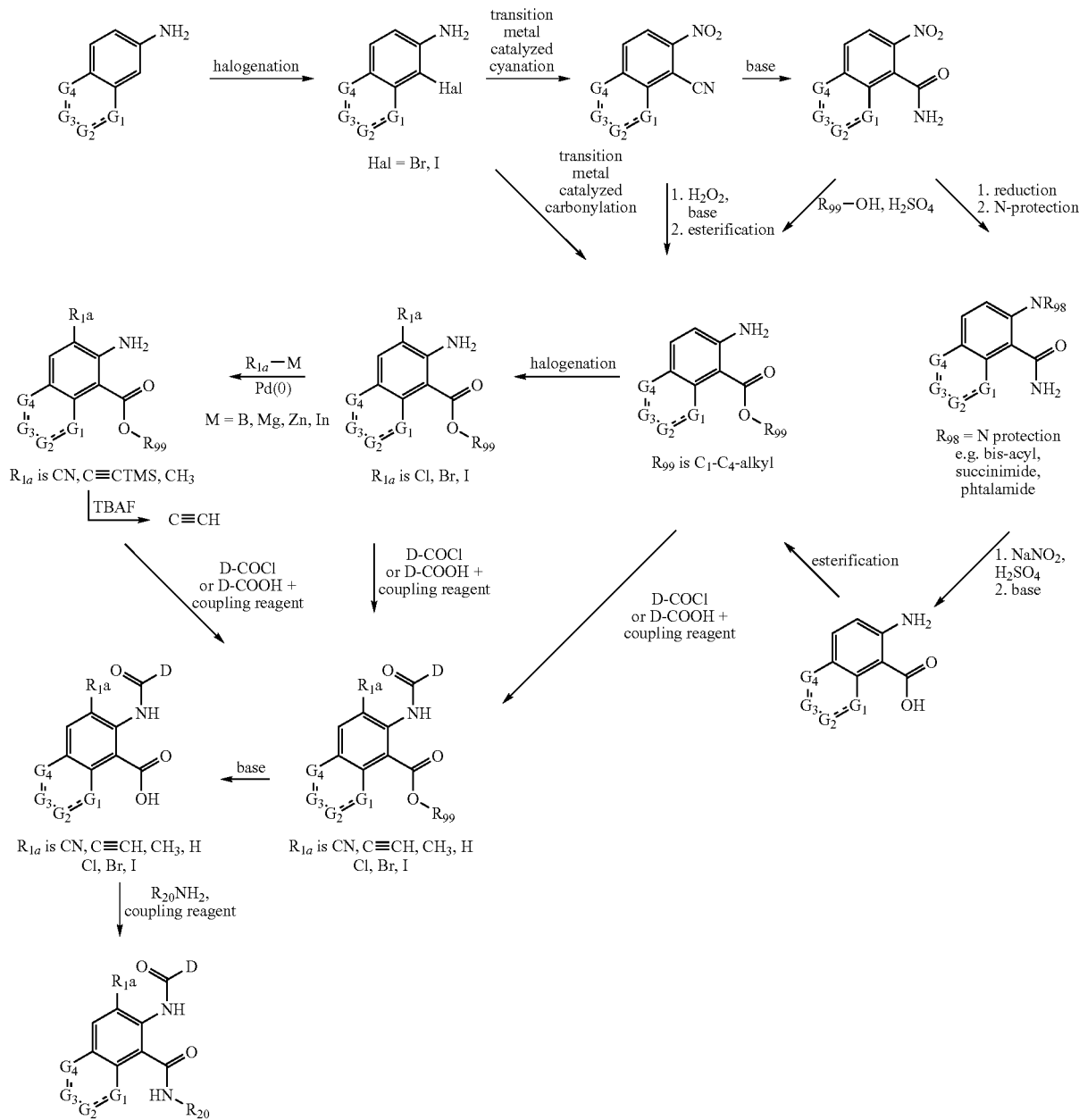

Reaction Scheme 5: Preparation of Compounds of Formula I:
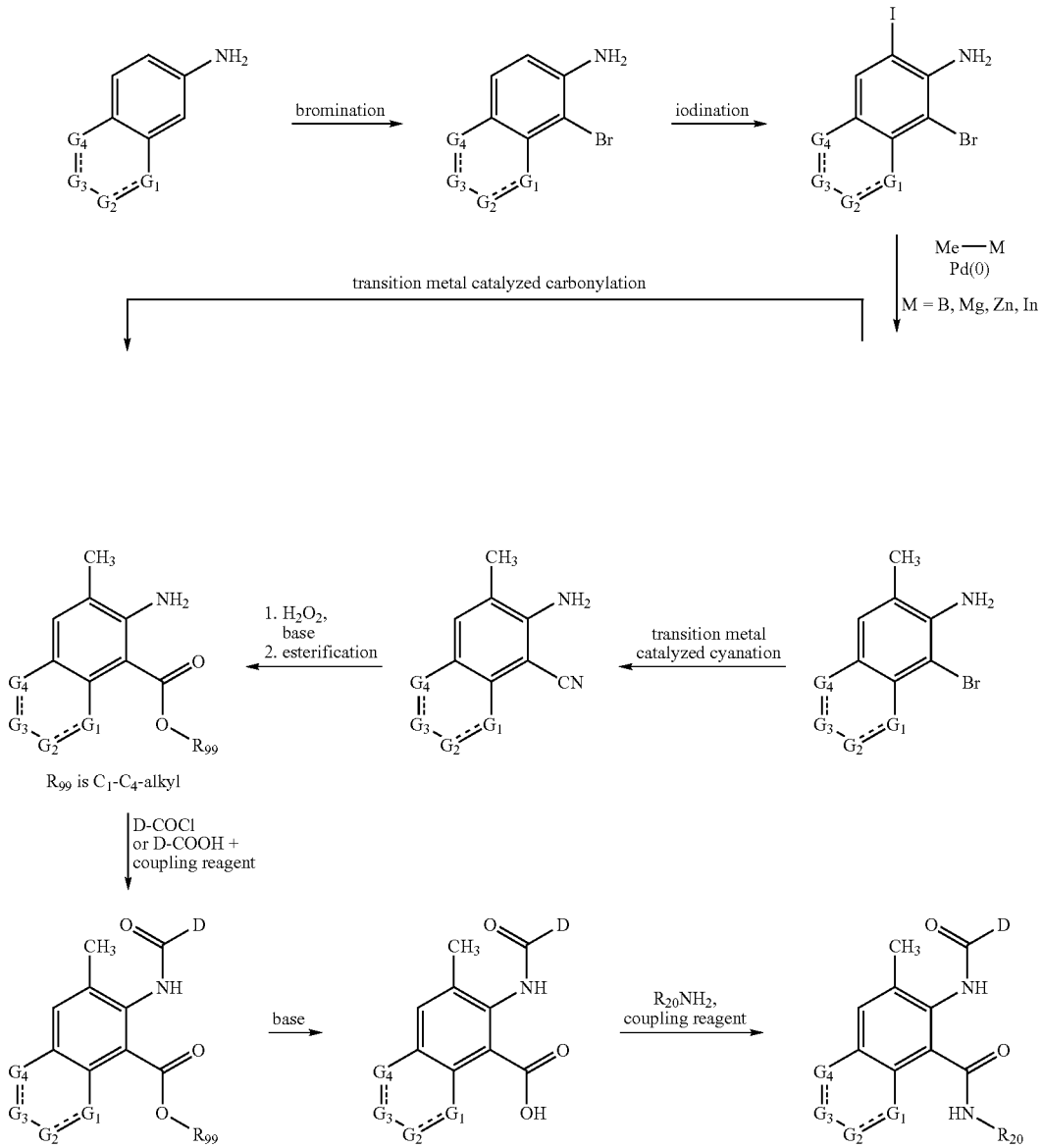
Reaction Scheme 6: Preparation of Compounds of Formula I (for indazoles):
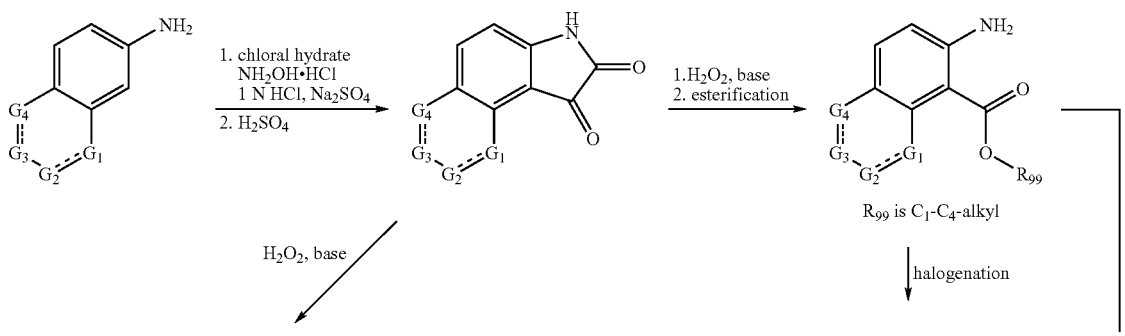

-continued
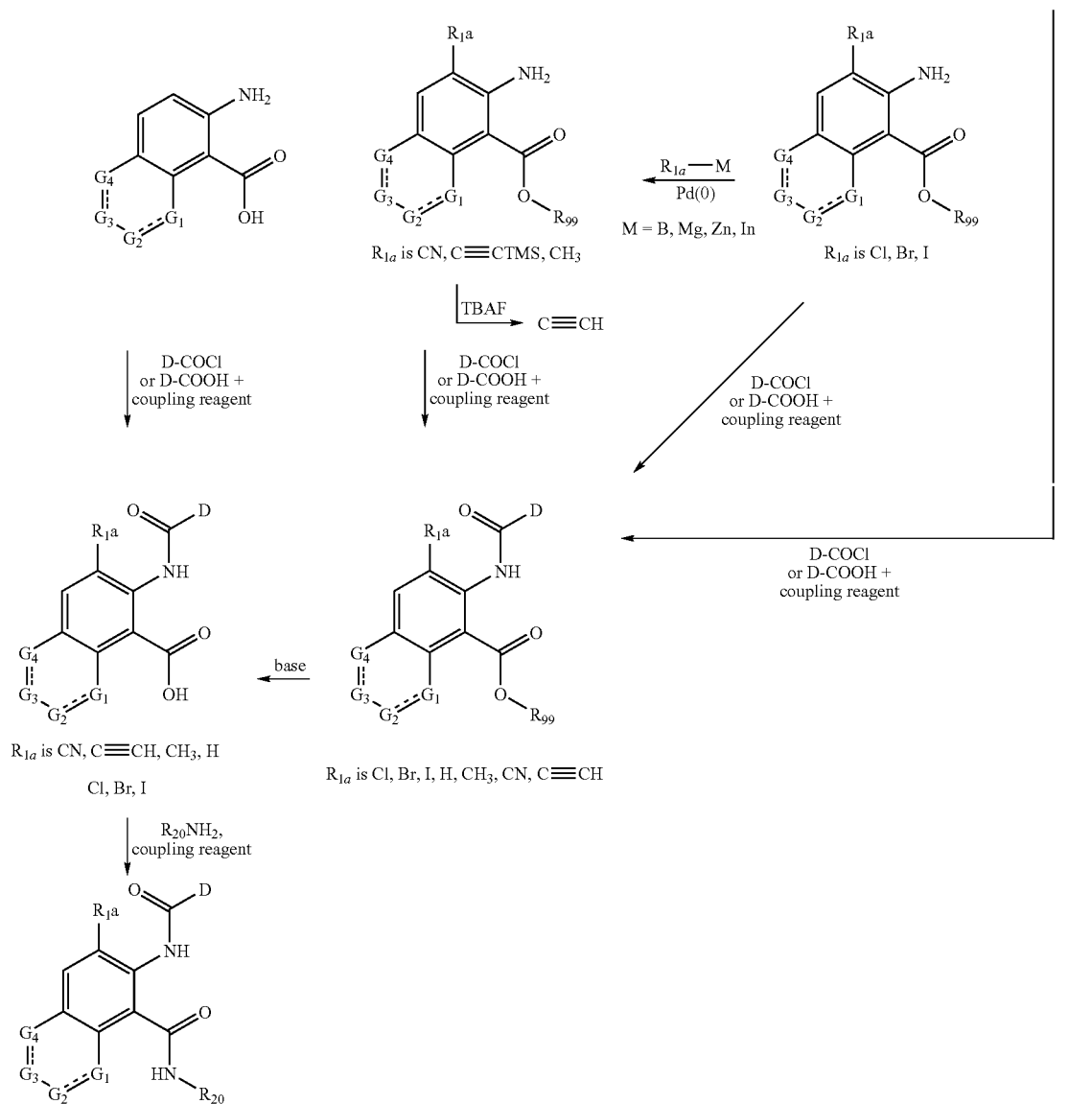
Reaction Scheme 7: Preparation of Compounds of Formula I:
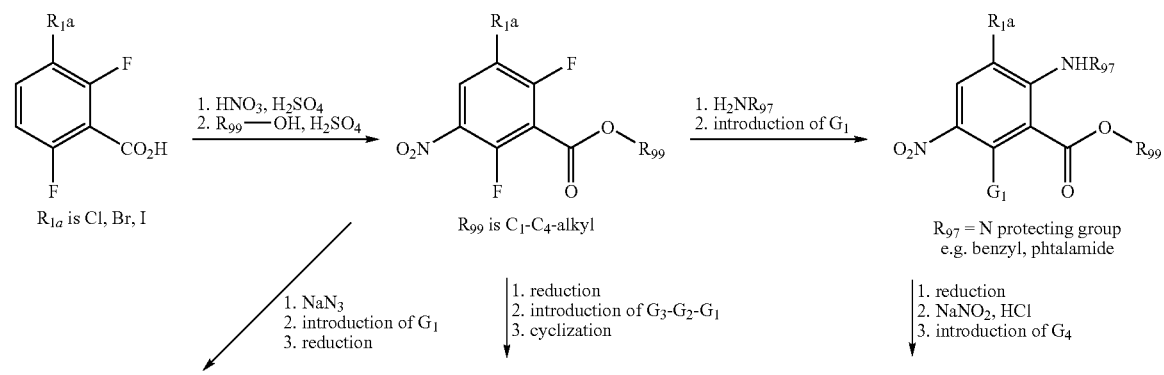

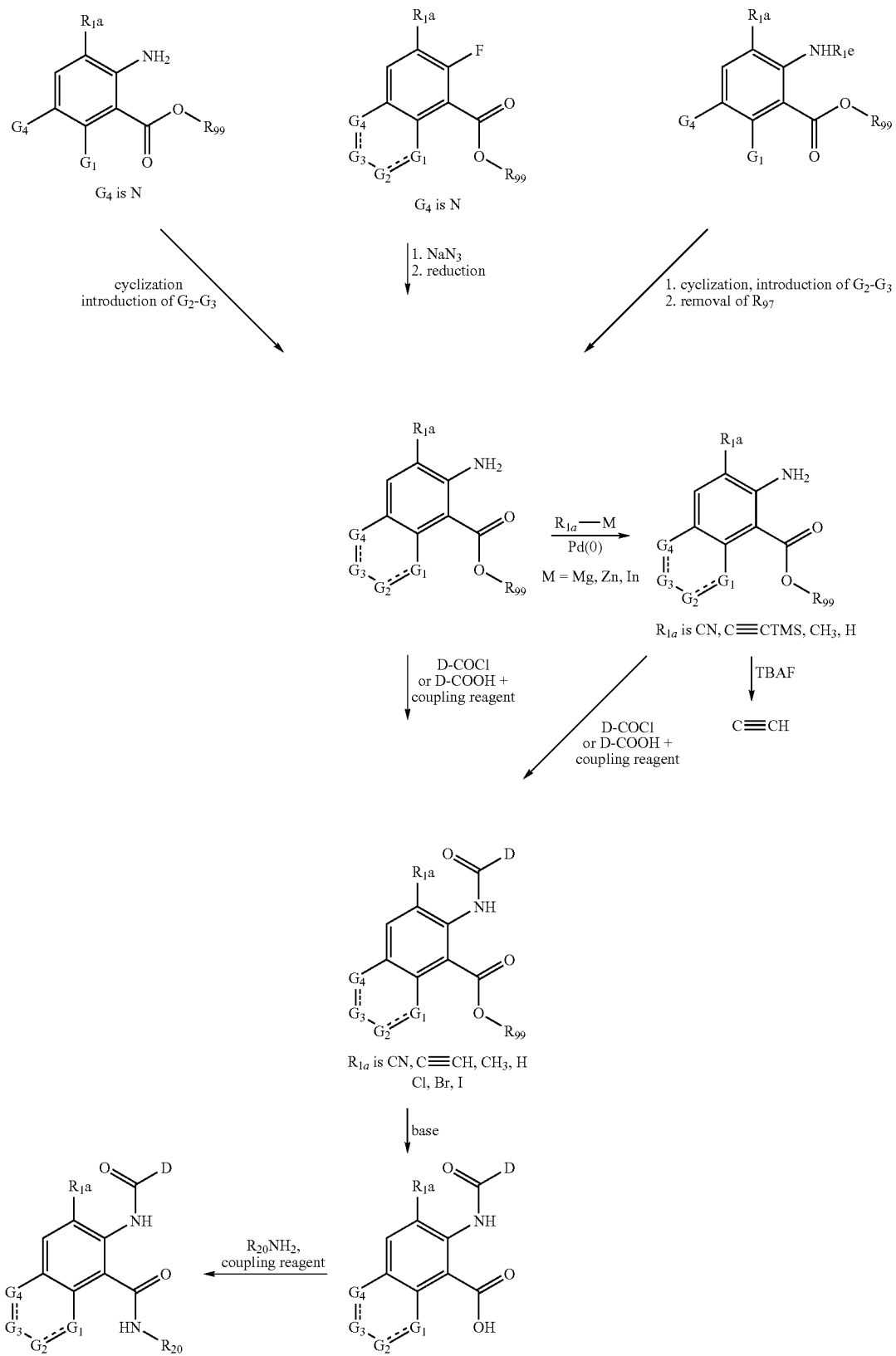

Reaction Scheme 7: Preparation of Compounds of Formula I (for indoles):

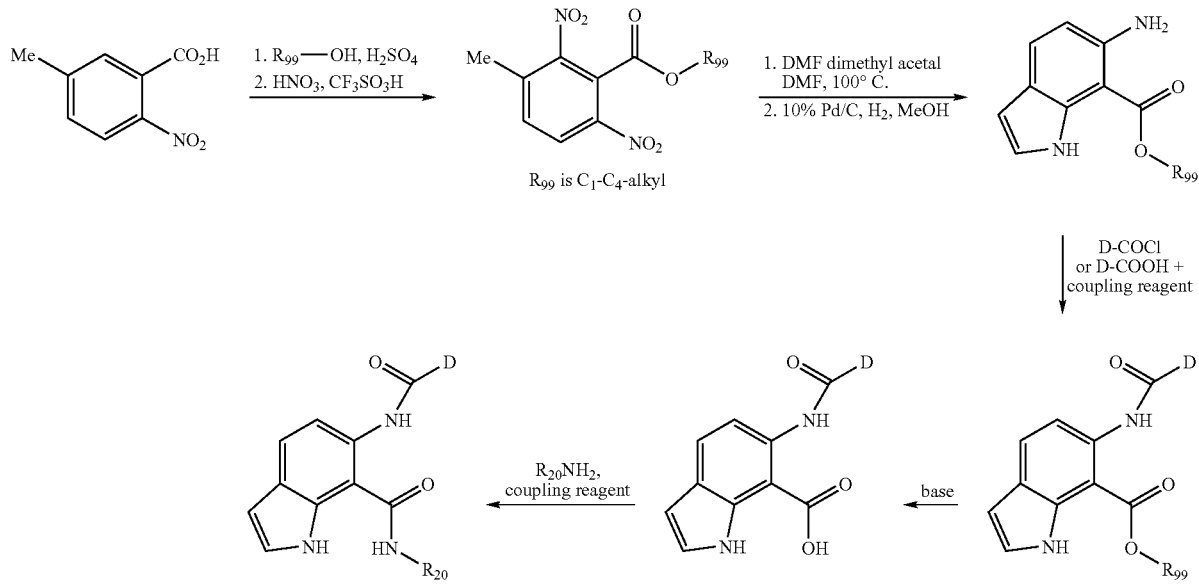

TABLE B

Intermediates:

| Anthranilic Acids And Methyl Ester Derivatives | MS/NMR |
|---|---|
| ![structure: 6-amino-1H-indole-7-carboxylic acid] | $^1$H-NMR (MeOD$_4$, 400 MHz): 7.51 (m, 1 H), 7.05 (d, 1 H), 6.55 (d, 1 H), 6.33 (m, 1 H) ppm |
| ![structure: 6-amino-1H-indazole-7-carboxylic acid] | 178/179 (M + H)$^+$ |
| ![structure: 6-amino-5-chloro-1H-indazole-7-carboxylic acid] | 212/214 (M + H)$^+$ |
| ![structure: 6-amino-5-bromo-1H-indazole-7-carboxylic acid] | 256/258 (M + H)$^+$ |

TABLE B-continued

Intermediates:

| Anthranilic Acids And Methyl Ester Derivatives | MS/NMR |
|---|---|
| ![structure: methyl 6-amino-5-methyl-1H-indazole-7-carboxylate] | 318/319 (M + H)$^+$ |
| ![structure: 6-amino-5-methyl-1H-indazole-7-carboxylic acid] | 192/193 (M + H)$^+$ |
| ![structure: 6-amino-5-cyano-1H-indazole-7-carboxylic acid] | 203/204 (M + H)$^+$ |

TABLE B-continued

Intermediates:

| Anthranilic Acids And Methyl Ester Derivatives | MS/NMR |
|---|---|
| 5-(trimethylsilylethynyl)-6-amino-7-methoxycarbonyl-1H-indazole | 288/289 (M + H)+ |
| 5-ethynyl-6-amino-7-carboxy-1H-indazole | 202/203 (M + H)+ |
| 6-amino-5-carboxyquinoline | 189/190 (M + H)+ |
| 7-bromo-6-amino-5-methoxycarbonylquinoline | 280/282 (M + H)+ |
| 7-methyl-6-amino-5-carboxyquinoline | 203/204 (M + H)+ |
| 3-bromo-5-chloro-6-amino-7-carboxy-1H-indazole | 290/292 (M + H)+ |
| 5-chloro-6-amino-7-carboxy-3-methyl-1H-indazole | 226/228 (M + H)+ |
| 7-amino-8-carboxyquinoline | 189/190 (M + H)+ |
| 5-chloro-6-amino-7-carboxy-2,1,3-benzothiadiazole | 228/230 (M − H)− |
| 5-chloro-6-amino-7-methoxycarbonyl-2-methyl-1H-benzimidazole | 1H-NMR (CDCl3, 400 MHz): 8.36 (s, 1 H), 7.60 (s, 1 H), 4.02 (s, 3 H), 3.99 (s, 3 H) ppm |
| 6-chloro-7-amino-8-carboxy-2,3-dimethylquinoxaline | 274/276 (M + Na)+ |
| 5-chloro-6-amino-7-methoxycarbonyl-1H-benzimidazole | 226/228 (M + H)+ |

The starting compounds and intermediates of the reaction schemes are known or can be prepared according to methods known to a person skilled in the art.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound I can be converted in a manner known per se into another compound I by replacing one or more substituents of the starting compound I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,

*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa* decemLineata, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp.;

from the order Diptera, for example,

*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;

from the order Heteroptera, for example,

*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;

from the order Homoptera, for example,

*Aleurothrixus floccosus, Aleyrodes brassicae, Aonidiella* spp., Aphididae, *Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* from the order Hymenoptera, for example,

Acromyrmex, *Atta* spp., *Cephus* spp., *Diprion* spp., Diprionidae, *Gilpinia polytoma, Hoplocampa* spp., *Lasius* spp., *Monomorium pharaonis, Neodiprion* spp., *Solenopsis* spp. and *Vespa* spp.;

from the order Isoptera, for example,

*Reticulitermes* spp.;

from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola* fusca, *Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora* gossypiela, *Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order *Mallophaga*, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Periplaneta* spp. and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Frankliniella* spp., *Hercinothrips* spp., *Scirtothrips aurantii, Taeniothrips* spp., *Thrips palmi* and *Thrips tabaci;* and from the order Thysanura, for example,

*Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on or gans, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above.

CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus,* and also hymenopterans such as *Sirex juvencus, Urocerus gigas, Urocerus gigas taignus* and *Urocerus augur,* and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus,* and bristletails such as *Lepisma saccharina.*

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a pnonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:

| active ingredient: | 1 to 95%, preferably 5 to 20% |
| surfactant: | 1 to 30%, preferably 10 to 20% |
| solvent: | 5 to 98%, preferably 70 to 85% |

Dusts:

| active ingredient: | 0.1 to 10%, preferably 0.1 to 1% |
| solid carrier: | 99.9 to 90%, preferably 99.9 to 99% |

Suspension Concentrates:

| active ingredient: | 5 to 75%, preferably 10 to 50% |
| water: | 94 to 24%, preferably 88 to 30% |
| surfactant: | 1 to 40%, preferably 2 to 30% |

Wettable Powders:

| active ingredient: | 0.5 to 90%, preferably 1 to 80% |
| surfactant: | 0.5 to 20%, preferably 1 to 15% |
| solid carrier: | 5 to 99%, preferably 15 to 98% |

Granulates:

| active ingredient: | 0.5 to 30%, preferably 3 to 15% |
| solid carrier: | 99.5 to 70%, preferably 97 to 85% |

PREPARATORY EXAMPLES

Example 1

Preparation of 6-{[2-(3-chloro-pyridin-2-yl)-5-trifluoromethyl-2H-pyrazole-3-carbonyl]-amino}-1H-indole-7-carboxylic acid isopropylamide a) Preparation of 6-amino-1H-indole-7-carboxylic acid methyl ester

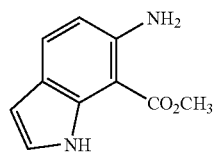 [SMILES: COC(=O)c1c(N)ccc2cc[nH]c12]

This compound is prepared as described in *J. Org. Chem.*, 1996, 61, 1155; LC/MS:191/192 (M+H)⁺.

b) Preparation of 6-amino-1H-indole-7-carboxylic acid

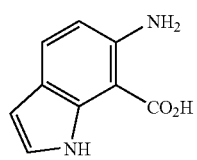 [SMILES: Nc1ccc2cc[nH]c2c1C(=O)O]

To a solution of 85.2 mg (0.45 mmol) of 6-amino-1H-indole-7-carboxylic acid methyl ester in 4 mL of dioxane and 1 mL of methanol, is added 0.45 mL (0.9 mmol) of an aqueous solution of NaOH 2N. The mixture is stirred over the night at 60° C. A new addition of 0.22 mL (0.45 mmol) of an aqueous solution of NaOH 2N is made and the mixture is stirred again 6 h at 60° C. and then cooled to ambient temperature. After evaporation of all the solvents, a crude yellowish residue is obtained and used directly in the next step; $^1$H-NMR (MeOD$_4$, 400 MHz): 7.51 (m, 1H), 7.05 (d, 1H), 6.55 (d, 1H), 6.33 (m, 1H) ppm.

c) Preparation of 7-[2-(3-chloro-pyridin-2-yl)-5-trifluoromethyl-2H-pyrazol-3-yl]-1H-8-oxa-1,6-diaza-cyclopenta[a]naphthalen-9-one

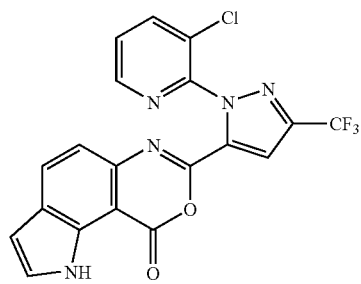 [SMILES: O=c1oc(-c2cc(C(F)(F)F)nn2-c2ncccc2Cl)nc2ccc3cc[nH]c3c12]

To a suspension of 79 mg (0.45 mmol) of 6-amino-1H-indole-7-carboxylic acid in 7 mL of acetonitrile, is added 130 mg (0.45 mmol) of 2-(3-chloro-pyridin-2-yl)-5-trifluoromethyl-2H-pyrazole-3-carboxylic acid followed by 0.16 mL (2.06 mmol) of pyridine. The mixture is stirred at ambient temperature during 30 minutes. Then the suspension is cooled to 0° C. and 0.12 mL (1.57 mmol) of methanesulfonyl chloride is added dropwise. The mixture is stirred at 0° C. during 30 minutes and 2 hours at ambient temperature. After evaporation of the solvent, the residue is triturated with a minimum of cold water. The precipitate which is formed is filtrated and washed with cold water. The residue is then purified by column chromatography on silica gel with hexanes and ethyl acetate as eluents and 47.1 mg (0.11 mmol, 25%) of a yellowish solid are obtained; LC/MS:432/434 (M+H)⁺.

d) Preparation of 6-{[2-(3-chloro-pyridin-2-yl)-5-trifluoromethyl-2H-pyrazol-3-carbonyl]-amino}-1H-indole-7-carboxylic acid isopropylamide

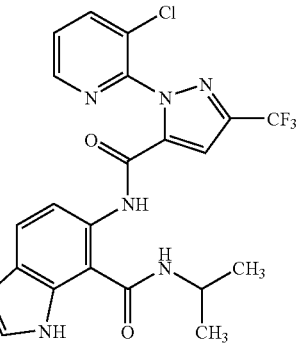

To a solution of 110 mg (0.25 mmol) of the crude 7-[2-(3-chloro-pyridin-2-yl)-5-trifluoromethyl-2H-pyrazol-3-yl]-1H-8-oxa-1,6-diaza-cyclopenta[a]naphthalen-9-one in 2.5 mL of anhydrous tetrahydrofuran, under Argon, is added 0.07 mL (0.77 mmol) of isopropylamine. The reaction is stirred during 5 hours at ambient temperature and then quenched with an aqueous saturated solution of ammonium chloride. The product is extracted twice with ethyl acetate and the combined organic phases are dried on Na$_2$SO$_4$, filtrated and the solvent is evaporated. After purification by flash chromatography on silica gel with hexanes and ethyl acetate as eluents and a preparative thin layer chromatography, 18.5 mg (0.04 mmol, 16%) of a white solid are obtained; LC/MS:513/515 (M+Na)⁺, m.p.: 240-242° C.

Example 2

Preparation of 6-{[2-(3-chloro-pyridin-2-yl)-5-trifluoromethyl-2H-pyrazole-3-carbonyl]-amino}-1H-indole-7-carboxylic acid cyclopropylamide

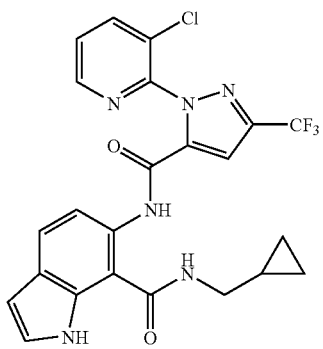 [SMILES: O=C(NCC1CC1)c1c(NC(=O)c2cc(C(F)(F)F)nn2-c2ncccc2Cl)ccc2cc[nH]c12]

See step d of example 1 with 7-[2-(3-chloro-pyridin-2-yl)-5-trifluoromethyl-2H-pyrazol-3-yl]-1H-8-oxa-1,6-diaza-cyclopenta[a]naphthalen-9-one as starting material and cyclopropanemethylamine. After 3 hours of reaction, work-up and column chromatography purification, a white powder is obtained (75%); LC/MS:525/527 (M+Na)$^+$, m.p.: 239-241° C.

Example 3

Preparation of 6-{[2-(3-chloro-pyridin-2-yl)-5-trifluoromethyl-2H-pyrazole-3-carbonyl]-amino}-1H-indazole-7-carboxylic acid isopropylamide a) Preparation of 1,6-dihydro-pyrrolo[2,3-g]indazole-7,8-dione

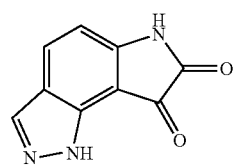 [SMILES: O=C1Nc2ccc3cn[nH]c3c2C1=O]

This compound is prepared as described in *Tet. Lett.*, 1980, 21, 3029; LC/MS:188/189 (M+H)$^+$.

b) Preparation of 6-amino-1H-indazole-7-carboxylic acid

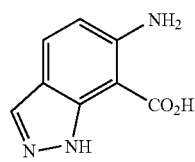 [SMILES: Nc1ccc2cn[nH]c2c1C(=O)O]

This compound is prepared as described in *J. Org. Chem.*, 2000, 65, 4193 using 1,6-dihydro-pyrrolo[2,3-g]indazole-7,8-dione as starting material; LC/MS:178/179 (M+H)$^+$.

c) Preparation of 7-[2-(3-chloro-pyridin-2-yl)-5-trifluoromethyl-2H-pyrazole-3-carbonyl]-1H-8-oxa-1,2,6-triaza-cyclopenta[a]naphthalen-9-one

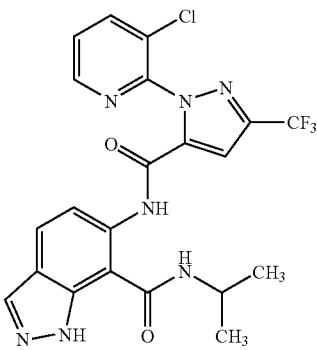 [SMILES: CC(C)NC(=O)c1c(NC(=O)c2cc(C(F)(F)F)nn2-c2ncccc2Cl)ccc2cn[nH]c12]

See step c example 1 with 6-amino-1H-indazole-7-carboxylic acid as starting material. After overnight reaction, work-up and column chromatography purification on silica gel with hexanes and ethyl acetate as eluents, a yellowish solid is obtained (63%); LC/MS:433/435 (M+H)$^+$.

d) Preparation of 6-{[2-(3-chloro-pyridin-2-yl)-5-trifluoromethyl-2H-pyrazole-3-carbonyl]-amino}-indazole-7-carboxylic acid isopropylamide See step d example 1 with 7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material. After overnight reaction and column chromatography purification on silica gel with hexanes and ethyl acetate as eluents, a slightly beige solid is obtained (72%); LC/MS:492/494 (M+H)$^+$, m.p.: 203-205° C.

Example 4

Preparation of 6-{[2-(3-chloro-pyridin-2-yl)-5-trifluoromethyl-2H-pyrazole-3-carbonyl]-amino}-1H-indazole-7-carboxylic acid cyclopropylmethyl-amide

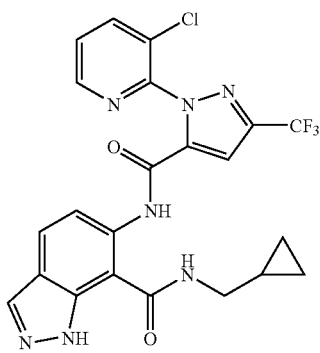 [SMILES: O=C(NCC1CC1)c1c(NC(=O)c2cc(C(F)(F)F)nn2-c2ncccc2Cl)ccc2cn[nH]c12]

See example 2 with 7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material. After overnight reaction and column chromatography purification on silica gel with hexanes and ethyl acetate as eluents, a slightly beige solid is obtained (77%); LC/MS:504/506 (M+H)$^+$, m.p.: 240-242° C.

Example 5

Preparation of 6-{[2-(3-chloro-pyridin-2-yl)-5-trifluoromethyl-2H-pyrazole-3-carbonyl]-amino}-1H-indazole-7-carboxylic acid bicyclopropyl-1-ylamide

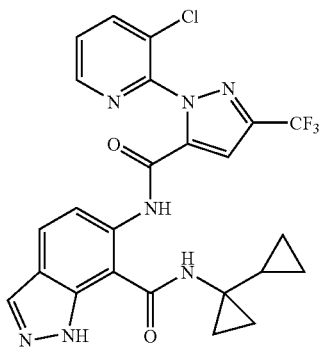 [SMILES: O=C(NC1(C2CC2)CC1)c1c(NC(=O)c2cc(C(F)(F)F)nn2-c2ncccc2Cl)ccc2cn[nH]c12]

See step d in example 1 with 7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material. The reaction is performed with 1.5 equivalents of bicyclopropyl-1-ylamine hydrochloride and triethylamine. After overnight reaction at ambient temperature, 0.3 equivalents of the amine and the base are added and the reaction is stirred overnight at 50° C. After column chromatography purification on silica gel with hexanes and ethyl acetate as eluents, a yellowish solid is obtained (70%); LC/MS:530/532 (M+H)$^+$, m.p.: 224-227° C.

Example 6

Preparation of 6-{[2-(3-chloro-pyridin-2-yl)-5-trifluoromethyl-2H-pyrazole-3-carbonyl]-amino}-1H-indazole-7-carboxylic acid methylamide

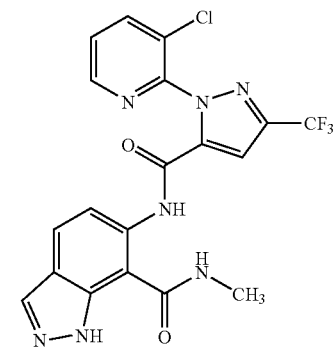 [SMILES: CNC(=O)c1c(NC(=O)c2cc(C(F)(F)F)nn2-c2ncccc2Cl)ccc2cn[nH]c12]

This compound is prepared as described in step d in example 1 with 7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material and 2 equivalents of methylamine (40% in water). After overnight reaction at ambient temperature, the mixture is evaporated and submitted to column chromatography purification with hexanes and ethyl acetate as eluents. A slightly beige solid is obtained (96%); LC/MS:464/466 (M+H)$^+$, m.p.: 190-192° C.

Example 7

Preparation of 6-{[2-(3-chloro-pyridin-2-yl)-5-trifluoromethyl-2H-pyrazole-3-carbonyl]-amino}-1H-indazole-7-carboxylic acid (1,1-dimethyl-2-methylsulfanyl-ethyl)-amide

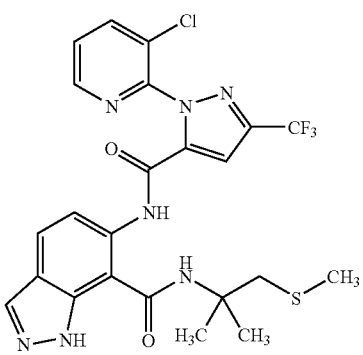 [SMILES: CSCC(C)(C)NC(=O)c1c(NC(=O)c2cc(C(F)(F)F)nn2-c2ncccc2Cl)ccc2cn[nH]c12]

To a mixture of 200 mg (0.46 mmol) of 7-[2-(3-chloro-pyridin-2-yl)-5-trifluoromethyl-2H-pyrazole-3-carbonyl]-1H-8-oxa-1,2,6-triaza-cyclopenta[a]naphthalen-9-one in 4 mL of anhydrous tetrahydrofuran is added 110 mg (0.92 mmol) of 1,1-dimethyl-2-methylsulfanylethylamine. The mixture is stirred overnight at ambient temperature, then 3 days at 50° C. Then 55 mg (0.46 mmol) of the amine is added again and the mixture is stirred overnight at 65° C. After column chromatography purification on silica gel with hexanes and ethyl acetate, a slightly beige solid (169 mg, 0.31 mmol, 66%) are obtained after evaporation; LC/MS: 552/554 (M+H)$^+$, m.p.: 100-105° C.

Example 8

Preparation of 6-{[2-(3-chloro-pyridin-2-yl)-5-trifluoromethyl-2H-pyrazole-3-carbonyl]-amino}-1H-indazole-7-carboxylic acid (2-methanesulfinyl-1,1-dimethyl-ethyl)-amide

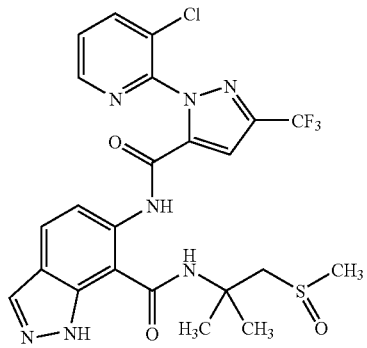 [SMILES: CS(=O)CC(C)(C)NC(=O)c1c(NC(=O)c2cc(C(F)(F)F)nn2-c2ncccc2Cl)ccc2cn[nH]c12]

To a mixture of 144 mg (0.26 mmol) of 6-{[2-(3-chloro-pyridin-2-yl)-5-trifluoromethyl-2H-pyrazole-3-carbonyl]-amino}-1H-indazole-7-carboxylic acid (1,1-dimethyl-2-methylsulfanylethyl)-amide, prepared in example 7 in 2.88 mL of methylene chloride at 0° C. is added dropwise 64 mg (0.26 mmol) of m-chloroperbenzoic acid dissolved in 0.5 mL of methylene chloride. The mixture is stirred and let warm-up to ambient temperature within 1 hour. The reaction is quenched by the addition of an aqueous saturated sodium carbonate solution. The product is extracted with ethyl acetate (3 times) and the combined organic extracts are dried on $Na_2SO_4$, filtrated and evaporated. After a flash chromatography with hexanes and ethyl acetate as eluents, 111 mg (0.17 mmol, 75%) of a white solid are obtained; LC/MS: 568/570 (M+H)$^+$.

Example 9

Preparation of 6-{[2-(3-chloro-pyridin-2-yl)-5-trifluoromethyl-2H-pyrazole-3-carbonyl]-amino}-1H-indazole-7-carboxylic acid (2-methanesulfonyl-1,1-dimethyl-ethyl)amide

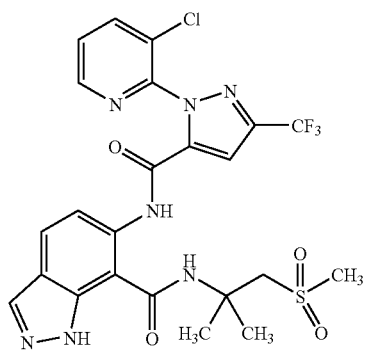 [SMILES: CC(C)(CS(C)(=O)=O)NC(=O)c1c(NC(=O)c2cc(C(F)(F)F)nn2-c2ncccc2Cl)ccc2cn[nH]c12]

See example 8 for the preparation of this compound using 6-{[2-(3-chloro-pyridin-2-yl)-5-trifluoromethyl-2H-pyrazole-3-carbonyl]-amino}-1H-indazole-7-carboxylic acid (1,1-dimethyl-2-methylsulfanyl-ethyl)-amide, prepared as in example 7, as starting material and 2 equivalents of m-chloroperbenzoic acid. After 30 minutes of stirring at ambient temperature under nitrogen, the reaction is quenched as described previously. After flash chromatography on silica gel with hexanes and ethyl acetate as eluents, a yellowish solid is obtained (67%); LC/MS:584/586 (M+H)$^+$.

Example 10

Preparation of 5-chloro-6-{[2-(3-chloro-pyridin-2-yl)-5-trifluoromethyl-2H-pyrazole-3-carbonyl]-amino}-1H-indazole-7-carboxylic acid isopropylamide a) Preparation of 6-amino-1H-indazole-7-carboxylic acid methyl ester

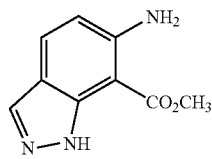 [SMILES: COC(=O)c1c(N)ccc2cn[nH]c12]

This compound is prepared as described in *Angew. Chem. Int. Ed. Engl.,* 1981, 20, 882 using 6-dihydro-pyrrolo[2,3-g]indazole-7,8-dione, prepared in step a example 3, as starting material; LC/MS:192/193 (M+H)$^+$.

b) Preparation of 6-amino-5-chloro-1H-indazole-7-carboxylic acid methyl ester

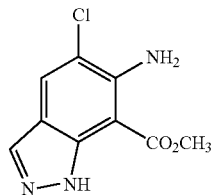

To a mixture of 1.66 g (8.71 mmol) of 6-amino-1H-indazole-7-carboxylic acid methyl ester in 17 mL of N,N-dimethylformamide, is added 1.21 g (8.71 mmol) of N-chlorosuccinimide. The mixture is stirred during 4 hours at 50° C. and then the solvent is evaporated. The residue is precipitated in ethyl acetate and after filtration and washings with ethyl acetate, 927 mg of a pure white solid are obtained. The filtrate is evaporated and submitted to a flash chromatography which gives an additional 723 mg of the compound. In totality, 1.65 g (84%) of a product are obtained as a white solid; LC/MS: 226/228 (M+H)$^+$.

c) Preparation of 6-amino-5-chloro-1H-indazole-7-carboxylic acid

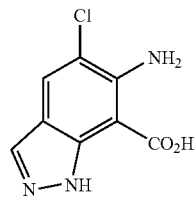

See step b example 1 for the preparation of this compound using 6-amino-5-chloro-1H-indazole-7-carboxylic acid methyl ester as starting material. The reaction is stirred 6 hours at 50° C. Then after evaporation, the residue is dissolved in a minimum of water and the pH of the mixture is adjusted to 2 with an aqueous solution of HCl 1N. The white precipitate, which is formed is filtrated and washed with a minimum of water. A white solid is obtained (96%); LC/MS: 212/214 (M+H)$^+$.

d) Preparation of 5-chloro-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one

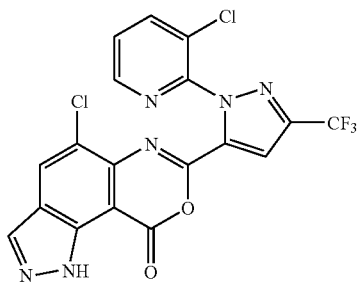 [SMILES: O=c1oc(-c2cc(C(F)(F)F)nn2-c2ncccc2Cl)nc2c(Cl)cc3cn[nH]c3c12]

See step c example 1 with 6-amino-5-chloro-1H-indazole-7-carboxylic acid as starting material. After overnight reaction at ambient temperature, work-up and a column chromatography purification on silica gel with hexanes and ethyl acetate as eluents affords the product (39%) as a yellowish solid; LC/MS:467/469 (M+H)$^+$.

e) Preparation of 5-chloro-6-{[2-(3-chloro-pyridin-2-yl)-5-trifluoromethyl-2H-pyrazole-3-carbonyl]-amino}-1H-indazole-7-carboxylic acid isopropylamide

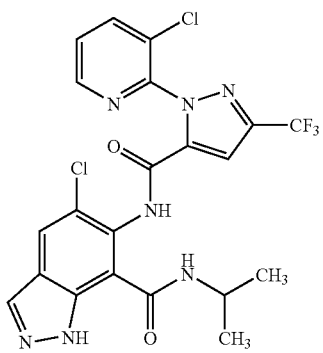

See step d example 1 with 5-chloro-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material. After overnight reaction and flash column chromatography purification a slightly beige solid is obtained (44%); LC/MS:526/528 (M+H)$^+$, m.p.: 245-247° C.

Example 11

Preparation of 5-chloro-6-{[2-(3-chloro-pyridin-2-yl)-5-trifluoromethyl-2H-pyrazole-3-carbonyl]-amino}-1H-indazole-7-carboxylic acid cyclopropyl-methyl-amide

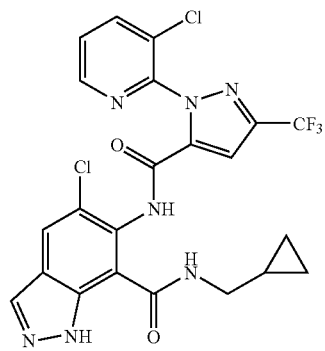 [SMILES: O=C(NCC1CC1)c1c(NC(=O)c2cc(C(F)(F)F)nn2-c2ncccc2Cl)c(Cl)cc2cn[nH]c12]

See example 2 with 5-chloro-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material with 2 equivalents of cyclopropanemethylamine and 1.5 equivalents of triethylamine. The reaction is stirred over the night at ambient temperature and after a flash chromatography, a white solid is obtained (43%); LC/MS:538/540 (M+H)$^+$, m.p.: >250° C.

Example 12

Preparation of 5-chloro-6-{[2-(3-chloro-pyridin-2-yl)-5-trifluoromethyl-2H-pyrazole-3-carbonyl]-amino}-1H-indazole-7-carboxylic acid bicyclopropyl-1-ylamide

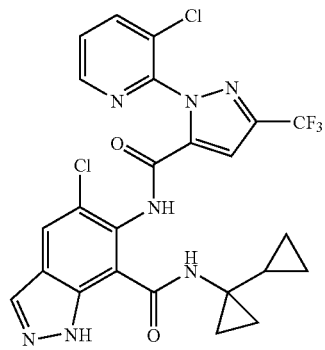

This compound is prepared as described in step d example 1 with 5-chloro-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material. The reaction is performed with 2 equivalents of bicyclopropyl-1-ylamine hydrochloride and triethylamine. After overnight stirring at ambient temperature, 0.3 equivalents of amine and base are added and the mixture is stirred again overnight at 50° C. After work-up and flash chromatography, a white solid is obtained (62%); LC/MS:564/566 (M+H)$^+$, m.p.: >250° C.

Example 13

Preparation of 5-chloro-6-{[2-(3-chloro-pyridin-2-yl)-5-trifluoromethyl-2H-pyrazole-3-carbonyl]-amino}-1H-indazole-7-carboxylic acid (1,1-dimethyl-2-methylsulfanylethyl)-amide

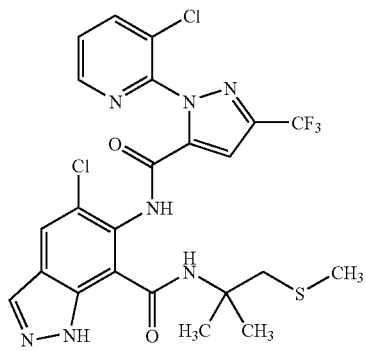 [SMILES: CSCC(C)(C)NC(=O)c1c(NC(=O)c2cc(C(F)(F)F)nn2-c2ncccc2Cl)c(Cl)cc2cn[nH]c12]

This compound is prepared as in example 7 with 5-chloro-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one, prepared in step d in example 10, as starting material and 2.5 equivalents of 1,1-dimethyl-2-methylsulfanyl-ethylamine. The reaction is stirred during 2 days at 65° C. and then 1 more equivalent of amine is added. The reaction is stirred for a further 2 days at 65° C. After work-up and flash chromatography purification, a yellowish solid is obtained (56%); LC/MS:586/588 (M+H)$^+$, m.p.: 100-105° C.

Example 14

Preparation of 5-chloro-6-{[2-(3-chloro-pyridin-2-yl)-5-trifluoromethyl-2H-pyrazole-3-carbonyl]-amino}-1H-indazole-7-carboxylic acid (2-methanesulfinyl-1,1-dimethylethyl)-amide

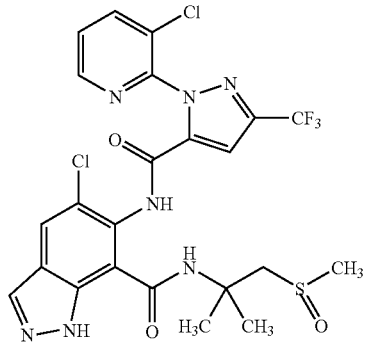 [SMILES: CS(=O)CC(C)(C)NC(=O)c1c(NC(=O)c2cc(C(F)(F)F)nn2-c2ncccc2Cl)c(Cl)cc2cn[nH]c12]

See example 8 for the preparation of this compound starting from 5-chloro-6-{[2-(3-chloro-pyridin-2-yl)-5-trifluoromethyl-2H-pyrazole-3-carbonyl]-amino}-1H-indazole-7-carboxylic acid (1,1-dimethyl-2-methylsulfanyl-ethyl)-amide, prepared in example 13. After 1 hour of reaction, work-up as described before and column chromatography purification, a yellowish solid is obtained (80%); LC/MS: 602/604 (M+H)$^+$, 624/626 (M+Na)$^+$.

Example 15

Preparation of 5-chloro-6-{[2-(3-chloro-pyridin-2-yl)-5-trifluoromethyl-2H-pyrazole-3-carbonyl]-amino}-1H-indazole-7-carboxylic acid (2-methanesulfonyl-1,1-dimethylethyl)-amide

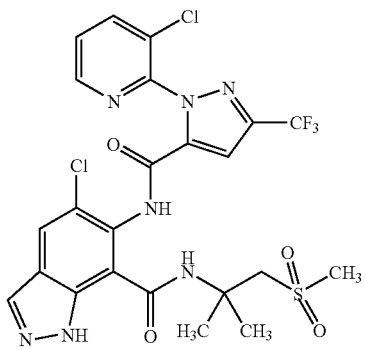 [SMILES: CC(C)(CS(C)(=O)=O)NC(=O)c1c(NC(=O)c2cc(C(F)(F)F)nn2-c2ncccc2Cl)c(Cl)cc2cn[nH]c12]

This compound is prepared as described in example 9 with 5-chloro-6-{[2-(3-chloro-pyridin-2-yl)-5-trifluoromethyl-2H-pyrazole-3-carbonyl]-amino}-1H-indazole-7-carboxylic acid (1,1-dimethyl-2-methylsulfanyl-ethyl)-amide as starting material, prepared in example 13, with 2 equivalents of m-chloroperbenzoic acid. After 30 minutes of stirring at ambient temperature under nitrogen, the reaction is quenched as described previously. After flash chromatography on silica gel with hexanes and ethyl acetate as eluents, a yellowish solid is obtained (57%); LC/MS:640/642 (M+Na)$^+$, m.p.: 173-176° C.

Example 16

Preparation of 5-bromo-6-{[2-(3-chloro-pyridin-2-yl)-5-trifluoromethyl-2H-pyrazole-3-carbonyl]-amino}-1H-indazole-7-carboxylic acid isopropylamide a) Preparation of 6-amino-5-bromo-1H-indazole-7-carboxylic acid methyl ester

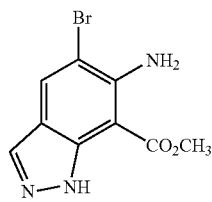 [SMILES: COC(=O)c1c(N)c(Br)cc2cn[nH]c12]

To a mixture of 3.4 g (17.78 mmol) of 6-amino-1H-indazole-7-carboxylic acid methyl ester, prepared as in step a in example 10, in 34 mL of N,N-dimethylformamide is added 3.16 g (17.78 mmol) of N-bromosuccinimide. The reaction is stirred at ambient temperature 4 hours. After concentration in vacuo the residue is triturated in ethyl acetate and after filtration 3.38 g of a brownish solid are obtained. The filtrate is evaporated and submitted to column chromatography purification on silica gel with hexanes and ethyl acetate as eluents to afford 563 mg of a white solid. In totality 3.95 g (82%) of a product are obtained; LC/MS:270/272 (M+H)$^+$.

b) Preparation of 6-amino-5-bromo-1H-indazole-7-carboxylic acid

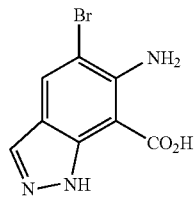

See step b example 1 for the preparation of this compound with 6-amino-5-bromo-1H-indazole-7-carboxylic acid methyl ester as starting material. After overnight reaction at 50° C., the solvent is evaporated and the product is precipitated with an aqueous solution of HCl 1N. The solid obtained is filtered and washed with a minimum of water. The crude white solid obtained is used directly in the next step; LC-MS: 256/258 (M+H)$^+$.

c) Preparation of 5-bromo-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one

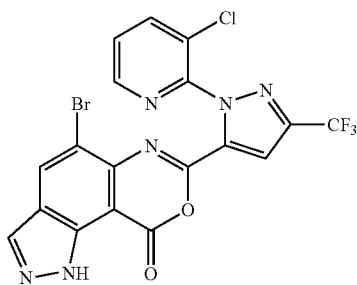 [SMILES: O=c1oc(-c2cc(C(F)(F)F)nn2-c2ncccc2Cl)nc2c(Br)cc3cn[nH]c3c12]

See step c in example 1 for the preparation of this compound with 6-amino-5-bromo-1H-indazole-7-carboxylic acid as starting material. The reaction is stirred for 30 minutes at 0° C. and then overnight at ambient temperature. After concentration in vacuo, the residue is precipitated with a minimum of water and filtrated. Column chromatography purification on silica gel with hexanes and ethyl acetate as eluents affords the product (51%) as a yellow solid; LC/MS: 511/513 (M+H)$^+$.

d) Preparation of 5-bromo-6-{[2-(3-chloro-pyridin-2-yl)-5-trifluoromethyl-2H-pyrazole-3-carbonyl]-amino}-1H-indazole-7-carboxylic acid isopropylamide

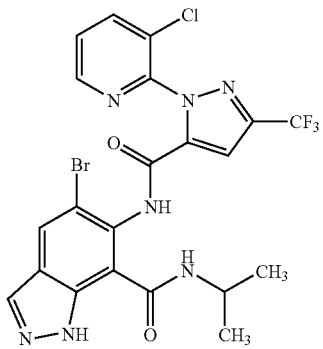 [SMILES: CC(C)NC(=O)c1c(NC(=O)c2cc(C(F)(F)F)nn2-c2ncccc2Cl)c(Br)cc2cn[nH]c12]

This compound is prepared as described in step d in example 1 with 5-bromo-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material. The reaction is performed with 3 equivalents of isopropylamine and the reaction mixture is stirred at ambient temperature overnight. After column chromatography purification, a white solid is obtained (57%); LC/MS: 570/572 (M+H)$^+$, m.p.: 189-190° C.

Example 17

Preparation of 5-bromo-6-{[2-(3-chloro-pyridin-2-yl)-5-trifluoromethyl-2H-pyrazole-3-carbonyl]-amino}-1H-indazole-7-carboxylic acid methylamide

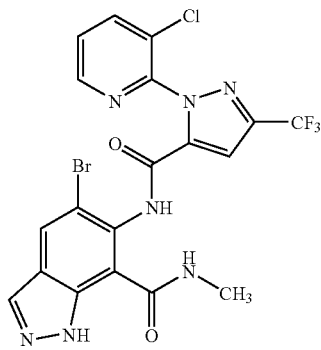

This compound is prepared as described in step d in example 1 with 5-bromo-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material and 3 equivalents of an aqueous solution of methylamine (40%). After overnight reaction at ambient temperature and purification by column chromatography on silica gel with hexanes and ethyl acetate as eluents, a white solid is obtained (59%); LC/MS:564/566 (M+Na)$^+$, m.p: >255° C.

Example 18

Preparation of 5-bromo-6-{[2-(3-chloro-pyridin-2-yl)-5-trifluoromethyl-2H-pyrazole-3-carbonyl]-amino}-1H-indazole-7-carboxylic acid bicyclopropyl-1-ylamide

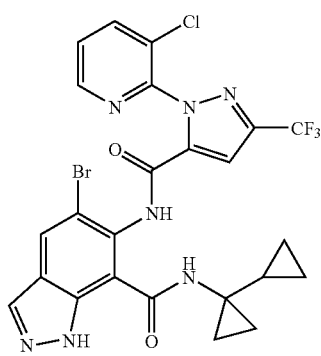 [SMILES: O=C(NC1(C2CC2)CC1)c1c(NC(=O)c2cc(C(F)(F)F)nn2-c2ncccc2Cl)c(Br)cc2cn[nH]c12]

This compound is prepared as described in step d of example 1 with 5-bromo-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material, 3 equivalents of bicyclopropyl-1-ylamine hydrochloride and 3 equivalents of triethylamine. After overnight reaction at ambient temperature, the mixture is warmed at 50° C. and stirred again during overnight, then 2 equivalents of amine and triethylamine are added and the reaction is stirred at 50° C. during 24 hours. After flash chromatography purification, a yellowish solid is obtained (53%); LC/MS:608/610 (M+H)$^+$, m.p.: 212-214° C.

Example 19

Preparation of 5-bromo-6-{[2-(3-chloro-pyridin-2-yl)-5-trifluoromethyl-2H-pyrazole-3-carbonyl]-amino}-1H-indazole-7-carboxylic acid cyclopropyl-methyl-amide

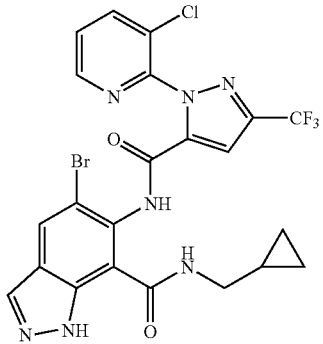

See example 2 for the preparation of this compound with 5-bromo-7-[2-(3-chloro-pyridin-2-yl)-5-trifluoromethyl-2H-pyrazole-3-carbonyl]-1H-8-oxa-1,2,6-triaza-cyclopenta[a]naphthalen-9-one as starting material and 3 equivalents of cyclopropanemethylamine. After overnight reaction at ambient temperature and flash chromatography with hexanes and ethyl acetate as eluents, a yellowish solid is obtained (72%); LC/MS:582/584 (M+H)$^+$, m.p.: 144-150° C.

Example 20

Preparation of 6-{[2-(3-chloro-pyridin-2-yl)-5-trifluoromethyl-2H-pyrazole-3-carbonyl]-amino}-2,7-dimethyl-quinoline-5-carboxylic acid isopropylamide

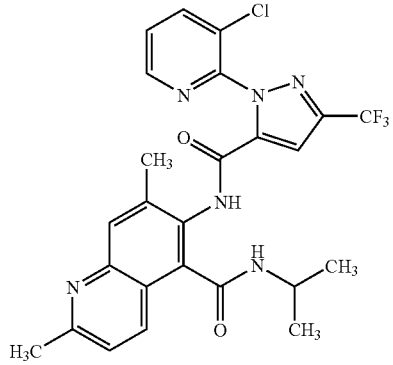 [SMILES: Cc1ccc2c(C(=O)NC(C)C)c(NC(=O)c3cc(C(F)(F)F)nn3-c3ncccc3Cl)c(C)cc2n1]

1.70 g (3.53 mMol) N-(4-amino-2-methyl-6-(((1-methylethyl)amino)carbonyl)phenyl)-1-(3-chloro-2-pyridinyl)-3-(trifluoromethyl)-1H-pyrazole-5-carboxamide (known from WO 03/016284) and 41 mg (0.18 mmol) benzyltriethylammonium chloride in 35 mL conc. HCl and 35 mL toluene are vigorously stirred at 60° C. Then 0.58 mL (7 mmol) crotonaldehyde is added and the reaction mixture is stirred under reflux during 1 hour. The mixture is then cooled to ambient temperature, diluted with 10 mL ethyl acetate/tetrahydrofuran (1:1, v/v) and neutralised with an aqueous solution of concentrated ammonia. The organic phase is extracted and washed once with brine, then dried on Na$_2$SO$_4$, filtrated and evaporated. After column chromatography purification on silica gel with dichloromethane/tetrahydrofuran (3:1) as eluents, the compound is recrystallised from tetrahydrofuran/hexane to afford a colourless solid; LC/MS:531/533 (M+H)$^+$, m.p.: >240° C.

Example 21

Preparation of 6-{[2-(3-chloro-pyridin-2-yl)-5-trifluoromethyl-2H-pyrazole-3-carbonyl]-amino}-2,7-dimethyl-quinoline-1-oxy-5-carboxylic acid isopropylamide

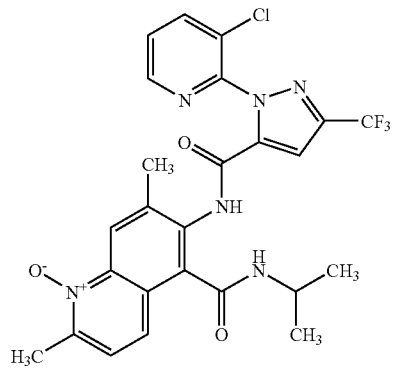 [SMILES: Cc1cc2c(ccc(C)[n+]2[O-])c(C(=O)NC(C)C)c1NC(=O)c1cc(C(F)(F)F)nn1-c1ncccc1Cl]

To 530 mg (1.0 mmol) 6-{[2-(3-chloro-pyridin-2-yl)-5-trifluoromethyl-2H-pyrazole-3-carbonyl]-amino}-2,7-dimethyl-quinoline-5-carboxylic acid isopropylamide prepared in example 20 in 25 mL dichloroethane, is added 380 mg (4.0 mMol) urea hydrogen peroxide addition compound and 0.31 mL trifluoroacetic acid. The mixture is stirred at 40° C. during 72 hours. After evaporation of the solvent, ethyl acetate is added and the mixture is washed with brine, dried and the solvent evaporated. Filtration of the residue over silica gel (eluent: tetrahydrofuran/hexane=2:1) gives a colourless solid, which is recrystallised from dichloromethane/hexane; LC/MS:547/549 (M+H)$^+$, m.p.: >230° C.

Example 22

Preparation of 6-{[2-(3-chloro-pyridin-2-yl)-5-trifluoromethyl-2H-pyrazole-3-carbonyl]-amino}-2,7-dimethyl-quinoline-5-carboxylic acid methylamide

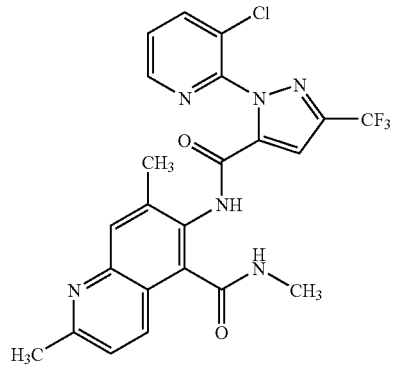 [SMILES: CNC(=O)c1c(NC(=O)c2cc(C(F)(F)F)nn2-c2ncccc2Cl)c(C)cc2nc(C)ccc12]

See example 20 for the preparation of this compound from N-(4-amino-2-methyl-6-(((1-methyl)amino)carbonyl)phenyl)-1-(3-chloro-2-pyridinyl)-3-(trifluoromethyl)-1H-pyrazole-5-carboxamide. After chromatography on silica gel (eluent: tetrahydrofuran/hexane=1:1) a colourless solid is obtained; m.p.: >134° C.

Example 23

Preparation of 6-{[2-(3-chloro-pyridin-2-yl)-5-trifluoromethyl-2H-pyrazole-3-carbonyl]-amino}-2,7-dimethyl-quinoline-5-carboxylic acid ethylamide

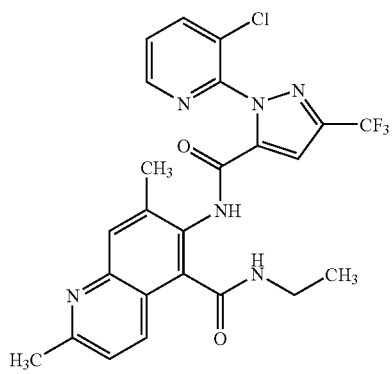 [SMILES: CCNC(=O)c1c(NC(=O)c2cc(C(F)(F)F)nn2-c2ncccc2Cl)c(C)cc2nc(C)ccc12]

See example 20 for the preparation of this compound from N-(4-amino-2-methyl-6-(((1-ethyl)amino)carbonyl)phenyl)-1-(3-chloro-2-pyridinyl)-3-(trifluoromethyl)-1H-pyrazole-5-carboxamide. After chromatography on silica gel (eluent: THF/hexane=1:1) a colourless solid is obtained; LC/MS: 517/519 (M+H)$^+$, m.p.: >230° C.

Example 24

Preparation of 6-{[2-(3-chloro-pyridin-2-yl)-5-trifluoromethyl-2H-pyrazole-3-carbonyl]-amino}-3-ethyl-7-methyl-2-propyl-quinoline-5-carboxylic acid isopropylamide

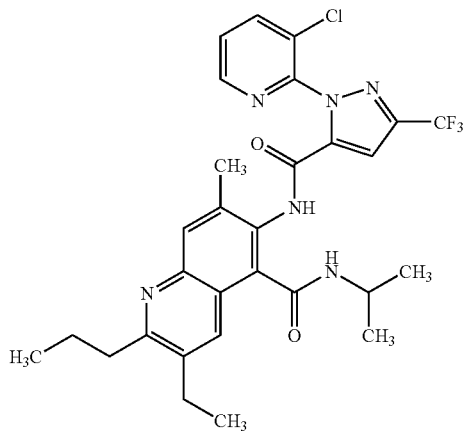 [SMILES: CCCc1nc2cc(C)c(NC(=O)c3cc(C(F)(F)F)nn3-c3ncccc3Cl)c(C(=O)NC(C)C)c2cc1CC]

0.48 g (1.0 mMol) N-(4-amino-2-methyl-6-(((1-methylethyl)amino)carbonyl)phenyl)-1-(3-chloro-2-pyridinyl)-3-(trifluoromethyl)-1H-pyrazole-5-carboxamide (known from WO 03/016284), 0.27 mL (3.0 mMol) butyraldehyde and 31 mg (0.05 mMol) ytterbium(III) trifluoromethanesulfonate in 20 mL dimethylsulfoxide are stirred at 100° C. during 24 hours. After cooling the mixture is diluted with ethyl acetate, washed with brine, dried and the solvent evaporated. Chromatography of the residue on silica gel (eluent: ethyl acetate/hexane=1:1) gives a colourless solid, which is recrystallised from dichloromethane/hexane; LC/MS:587/589 (M+H)$^+$, m.p. 213-220° C.

Example 25

Preparation of 6-{[2-(3-chloro-pyridin-2-yl)-5-trifluoromethyl-2H-pyrazole-3-carbonyl]-amino}-5-cyano-1H-indazole-7-carboxylic acid isopropylamide a) Preparation of 6-amino-5-cyano-1H-indazole-7-carboxylic acid methyl ester

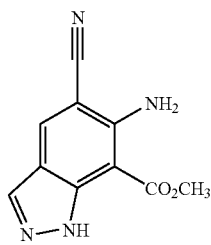 [SMILES: COC(=O)c1c(N)c(C#N)cc2cn[nH]c12]

To a solution of 500 mg (1.85 mmol) of 6-amino-5-bromo-1H-indazole-7-carboxylic acid methyl ester, prepared as in step a in example 16, in 10 mL of N,N-dimethylformamide under an atmosphere of argon is added 135 mg (1.15 mmol) of zinc cyanide and 206 mg (0.185 mmol) of tetrakis(triphenylphsophine)palladium. The reaction mixture is stirred in a microwave oven at 180° C. for 5 minutes. Then, a 1:1 v/v mixture of ethyl acetate and tertbutylmethyl ether and brine are added to the reaction and the phases are separated. The aqueous layer is extracted with tert-butylmethylether. The organic extracts are washed twice with brine, dried over MgSO$_4$ and concentrated in vacuo. The residue is purified by flash chromatography (SiO$_2$, hexane/ethyl acetate 2:1 to 1:1, gradient) to afford 380 mg of product (94%) as a yellowish solid; LC/MS:217/218 (M+H)$^+$.

b) Preparation of 6-amino-5-cyano-1H-indazole-7-carboxylic acid

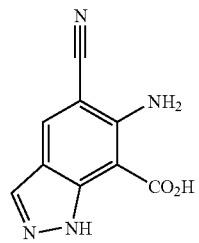 [SMILES: N#Cc1cc2cn[nH]c2c(C(=O)O)c1N]

See step b example 1 for the preparation of this compound with 6-amino-5-cyano-1H-indazole-7-carboxylic acid methyl ester as starting material. After 5 hours of reaction time at ambient temperature, the solvents are evaporated and water is added to the residue. The product is precipitated at pH 3 by addition of 1N aqueous HCl, filtrated, washed with a minimum of water and dried by azeotropic distillation with toluene. The yellowish solid (90%) obtained is used directly in the next step; LC/MS: 203 (M+H)$^+$.

c) Preparation of 7-[2-(3-chloro-pyridin-2-yl)-5-trifluoromethyl-2H-pyrazol-3-yl]-9-oxo-1,9-dihydro-8-oxa-1,2,6-triaza-cyclopenta[a]naphthalene-5-carbonitrile

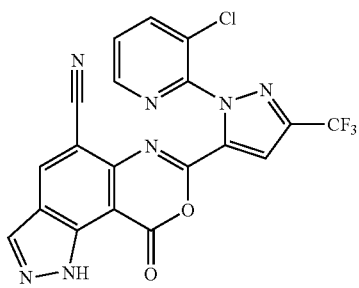 [SMILES: N#Cc1cc2cn[nH]c2c2c(=O)oc(-c3cc(C(F)(F)F)nn3-c3ncccc3Cl)nc12]

See step c in example 1 for the preparation of this compound with 6-amino-5-cyano-1H-indazole-7-carboxylic acid as starting material. The reaction mixture is stirred at 50° C. for 16 hours and then concentrated in vacuo. The solid residue is triturated with a minimum of water and filtrated. The yellow solid isolated is dried and engaged in the next step; LC/MS: 458/460 (M+H)$^+$.

d) Preparation of 6-{[2-(3-chloro-pyridin-2-yl)-5-trifluoromethyl-2H-pyrazole-3-carbonyl]-amino}-5-cyano-1H-indazole-7-carboxylic acid isopropylamide

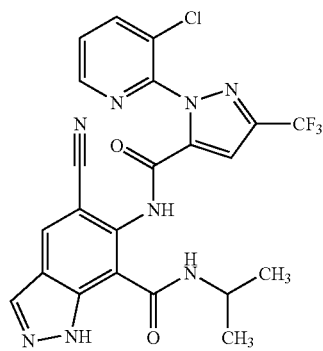 [SMILES: CC(C)NC(=O)c1c(NC(=O)c2cc(C(F)(F)F)nn2-c2ncccc2Cl)c(C#N)cc2cn[nH]c12]

To a mixture of 600 mg of the above 7-[2-(3-chloro-pyridin-2-yl)-5-trifluoromethyl-2H-pyrazol-3-yl]-9-oxo-1,9-dihydro-8-oxa-1,2,6-triaza-cyclopenta[a]naphthalene-5-carbonitrile in 5 mL of acetonitrile/water (4:1, v/v) is added 1.1 mL (12.9 mmol) of isopropylamine. The reaction mixture is stirred during 4 hours at ambient temperature and then concentrated in vacuo. After purification by flash chromatography (SiO$_2$, hexanes/ethyl acetate 4:1), 250 mg (38%) of a white solid are obtained; LC/MS:518/520 (M+H)$^+$.

Example 26

Preparation of 6-{[2-(3-chloro-pyridin-2-yl)-5-trifluoromethyl-2H-pyrazole-3-carbonyl]-amino}-5-cyano-1H-indazole-7-carboxylic acid bicyclopropyl-1-ylamide

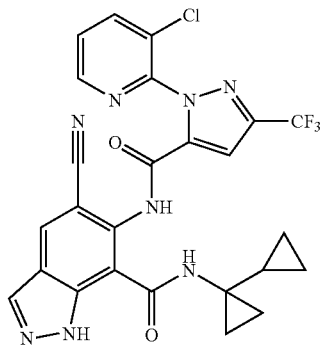 [SMILES: N#Cc1cc2cn[nH]c2c(C(=O)NC2(C3CC3)CC2)c1NC(=O)c1cc(C(F)(F)F)nn1-c1ncccc1Cl]

To a solution of 500 mg of the above 7-[2-(3-chloro-pyridin-2-yl)-5-trifluoromethyl-2H-pyrazol-3-yl]-9-oxo-1,9-dihydro-8-oxa-1,2,6-triaza-cyclopenta[a]naphthalene-5-carbonitrile in 8 mL of N,N-dimethylformamide is added 218 mg (1.63 mmol) of bicyclopropyl-1-ylamine hydrochloride and 303 µL (2.18 mmol) of triethylamine. The reaction is stirred at 60° C. for 24 hours and then concentrated in vacuo. The residue is taken-up with water and ethyl acetate. The phases are separated and the aqueous layer is washed with ethyl acetate. The combined organic layers are washed several times with brine, dried over MgSO$_4$ and concentrated in vacuo. Purification of the residue by flash chromatography (SiO$_2$, hexanes/ethyl acetate 3:9) affords 76 mg (12% over two steps) of the product as white solid; LC/MS: 555/557 (M+H)$^+$.

Example 27

Preparation of 6-{[2-(3-chloro-pyridin-2-yl)-5-methoxy-2H-pyrazole-3-carbonyl]-amino}-5-methyl-1H-indazole-7-carboxylic acid isopropylamide a) Preparation of 6-amino-5-methyl-1H-indazole-7-carboxylic acid methyl ester

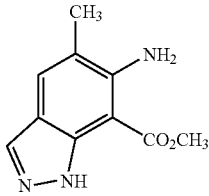

To a solution of 500 mg (1.85 mmol) of 6-amino-5-bromo-1H-indazole-7-carboxylic acid methyl ester, prepared as in step a in example 16, in 10 mL of dioxane under an atmosphere of argon is added 767 mg (5.55 mmol) of K$_2$CO$_3$, 106 mg (0.09 mmol) of tetrakis(triphenylphsophine)palladium and 232 mg (1.85 mmol) of trimethylboroxine. The reaction mixture is stirred in a microwave oven at 180° C. for 5 minutes. After filtration over Celite and concentration in vacuo, the residue is purified sequentially by flash chromatography (SiO₂, hexanes/ethyl acetate 6:4) and reverse phase chromatography to afford 163 mg of product (43% over two steps) as a pale yellowish solid; LC/MS:206/207 (M+H)⁺.

b) Preparation of 6-amino-5-methyl-1H-indazole-7-carboxylic acid

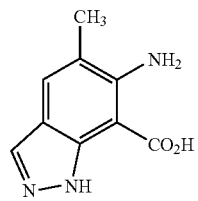

See step b example 1 for the preparation of this compound with 6-amino-5-methyl-1H-indazole-7-carboxylic acid methyl ester as starting material. After 24 h of reaction time at ambient temperature, the solvents are evaporated and water is added to the residue. The product is precipitated at pH 3 by addition of 1N aqueous HCl, filtrated, washed with a minimum of water and dried by azeotropic distillation with toluene. The yellowish solid (91%) obtained is used directly in the next step; LC/MS:5192/193 (M+H)⁺.

c) Preparation of 7-[2-(3-chloro-pyridin-2-yl)-5-methoxy-2H-pyrazol-3-yl]-5-methyl-1H-8-oxa-1,2,6-triaza-cyclopenta[a]naphthalen-9-one

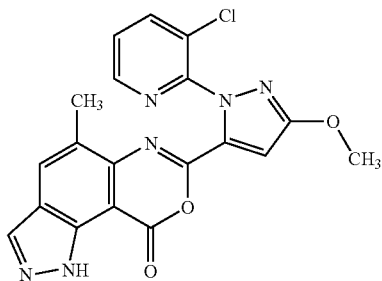 [SMILES: COc1cc(-c2nc3c(C)cc4cn[nH]c4c3c(=O)o2)n(-c2ncccc2Cl)n1]

See step c in example 1 for the preparation of this compound with 6-amino-5-methyl-1H-indazole-7-carboxylic acid as starting material. The reaction mixture is stirred at ambient temperature for 16 hours and then concentrated in vacuo. The solid residue is triturated with a minimum of water and filtrated. The yellowish solid isolated is dried and engaged in the next step; LC/MS:409/411 (M+H)⁺.

d) Preparation of 6-{[2-(3-chloro-pyridin-2-yl)-5-methoxy-2H-pyrazole-3-carbonyl]-amino}-5-methyl-1H-indazole-7-carboxylic acid isopropylamide

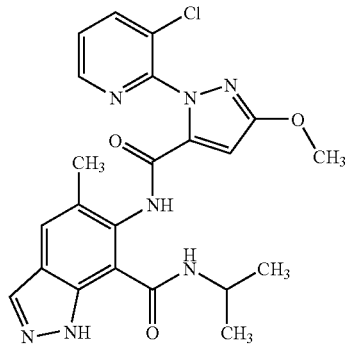 [SMILES: COc1cc(C(=O)Nc2c(C)cc3cn[nH]c3c2C(=O)NC(C)C)n(-c2ncccc2Cl)n1]

To a mixture of 500 mg of the above 7-[2-(3-chloro-pyridin-2-yl)-5-methoxy-2H-pyrazol-3-yl]-5-methyl-1H-8-oxa-1,2,6-triaza-cyclopenta[a]naphthalen-9-one in 10 mL of 4:1 (v/v) mixture of acetonitrile/water is added 1.0 mL (12.2 mmol) of isopropylamine. The reaction mixture is stirred during 1 hour at ambient temperature and for 2.5 hours at 60° C. and then concentrated in vacuo. The residue is taken-up with brine and tert-butylmethylether. The phases are separated and the aqueous layer is washed with tert-butylmethylether. The combined organic layers are washed with brine, dried over MgSO₄ and concentrated in vacuo. Purification of the residue by flash chromatography (SiO₂, hexanes/ethyl acetate 3:7) affords 118 mg (19% over two steps) of the product as white solid; LC/MS:468/470 (M+H)⁺, m.p.: 148-151° C.

Example 28

Preparation of 6-{[2-(3-chloro-pyridin-2-yl)-5-methoxy-2H-pyrazole-3-carbonyl]-amino}-5-methyl-1H-indazole-7-carboxylic acid bicyclopropyl-1-ylamide

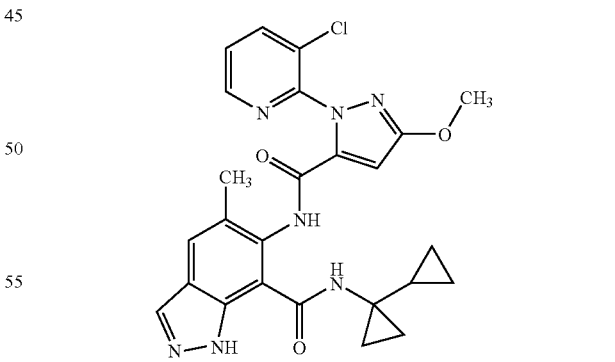

To a solution of 500 mg of the above 7-[2-(3-chloro-pyridin-2-yl)-5-methoxy-2H-pyrazol-3-yl]-5-methyl-1H-8-oxa-1,2,6-triaza-cyclopenta[a]naphthalen-9-one in 8 mL of N,N-dimethylformamide is added 244 mg (1.83 mmol) of bicyclopropyl-1-ylamine hydrochloride and 340 μL (2.44 mmol) of triethylamine. The reaction is stirred at 70° C. for 16 hours and then concentrated in vacuo. The residue is taken-up with water and ethyl acetate. The phases are separated and the aqueous layer is washed with ethyl acetate. The combined organic layers are washed several times with brine, dried over MgSO$_4$ and concentrated in vacuo. Purification of the residue by flash chromatography (SiO$_2$, hexanes/ethyl acetate 3:7) affords 90 mg (15% over two steps) of product as a pale yellowish solid; LC/MS:506/508 (M+H)$^+$, m.p.: 150-154° C.

Example 29

Preparation of 6-{[2-(3-chloro-pyridin-2-yl)-5-(2,2,2-trifluoro-ethoxy)-2H-pyrazole-3-carbonyl]-amino}-5-methyl-1H-indazole-7-carboxylic acid isopropylamide a) Preparation of 7-[2-(3-chloro-pyridin-2-yl)-5-(2,2,2-trifluoro-ethoxy)-2H-pyrazol-3-yl]-5-methyl-1H-8-oxa-1,2,6-triaza-cyclopenta[a]naphthalen-9-one

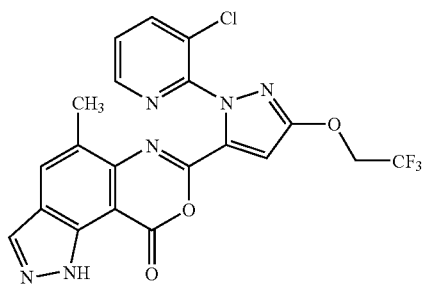 [SMILES: Cc1cc2cn[nH]c2c2c(=O)oc(-c3cc(OCC(F)(F)F)nn3-c3ncccc3Cl)nc12]

To a suspension of 500 mg (2.61 mmol) of 6-amino-5-methyl-1H-indazole-7-carboxylic acid in 20 mL of anhydrous tetrahydrofuran is added 790 mg (2.61 mmol) of 2-(3-chloro-pyridin-2-yl)-5-(2,2,2-trifluoro-ethoxy)-2H-pyrazole-3-carboxylic acid followed by 945 µL (11.7 mmol) of pyridine. The mixture is stirred at ambient temperature during 30 minutes. Then the suspension is cooled to 0° C. and 708 µL (9.1 mmol) of methanesulfonyl chloride are added dropwise. The mixture is stirred at 50° C. for 16 hours. Then the solvent is evaporated and the residue is triturated with a minimum of cold water. The precipitate, which is formed is filtrated and washed with cold water. The pale yellowish product obtained (1.0 g) is engaged in the next step: LC/MS: 477/479 (M+H)$^+$.

b) Preparation of 6-{[2-(3-chloro-pyridin-2-yl)-5-(2,2,2-trifluoro-ethoxy)-2H-pyrazole-3-carbonyl]-amino}-5-methyl-1H-indazole-7-carboxylic acid isopropylamide

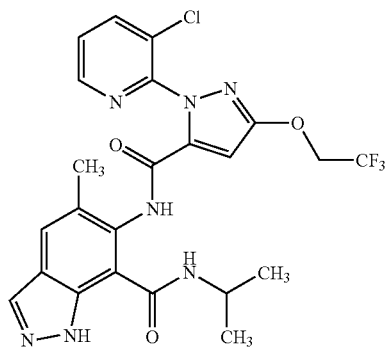 [SMILES: Cc1cc2cn[nH]c2c(C(=O)NC(C)C)c1NC(=O)c1cc(OCC(F)(F)F)nn1-c1ncccc1Cl]

To a suspension of 500 mg of the above 7-[2-(3-chloro-pyridin-2-yl)-5-(2,2,2-trifluoro-ethoxy)-2H-pyrazol-3-yl]-5-methyl-1H-8-oxa-1,2,6-triaza-cyclopenta[a]naphthalen-9-one in 10 mL of acetonitrile/water (4:1, v/v) is added 885 µL (10.4 mmol) of isopropylamine. The reaction mixture is stirred for 16 hours at ambient temperature and then concentrated in vacuo. The residue is taken-up with brine and ethyl acetate. The phases are separated and the aqueous layer is washed with ethyl acetate. The combined organic layers are washed with brine, dried over MgSO$_4$ and concentrated in vacuo. Purification of the residue by flash chromatography (SiO$_2$, hexane/ethyl acetate 4:6) affords 60 mg (10% over two steps) of the product as a white solid; LC/MS:536/538 (M+H)$^+$, m.p.: 247-250° C.

Example 30

6-{[2-(3-chloro-pyridin-2-yl)-5-(2,2,2-trifluoro-ethoxy)-2H-pyrazole-3-carbonyl]-amino}-5-methyl-1H-indazole-7-carboxylic acid bicyclopropyl-1-ylamide

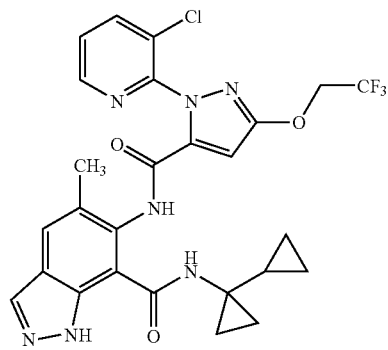 [SMILES: Cc1cc2cn[nH]c2c(C(=O)NC2(C3CC3)CC2)c1NC(=O)c1cc(OCC(F)(F)F)nn1-c1ncccc1Cl]

See example 28 for the preparation of this compound with 7-[2-(3-chloro-pyridin-2-yl)-5-(2,2,2-trifluoro-ethoxy)-2H-pyrazol-3-yl]-5-methyl-1H-8-oxa-1,2,6-triaza-cyclopenta[a]naphthalen-9-one as the starting material. The reaction is stirred at 60° C. for 24 hours and then concentrated in vacuo. The residue is taken-up with water and ethyl acetate. The phases are separated and the aqueous layer is washed with ethyl acetate. The combined organic layers are washed several times with brine, dried over MgSO$_4$ and concentrated in vacuo. Purification of the residue by flash chromatography (SiO$_2$, hexane/ethyl acetate 3:7) affords 75 mg (10% over two steps) of the product as a white solid; LC/MS:574/576 (M+H)$^+$, m.p.: 240-242° C.

Example 31

Preparation of 6-{[5-bromo-2-(3-chloro-pyridin-2-yl)-2H-pyrazole-3-carbonyl]-amino}-5-methyl-1H-indazole-7-carboxylic acid isopropylamide a) Preparation of 7-[5-bromo-2-(3-chloro-pyridin-2-yl)-2H-pyrazol-3-yl]-5-methyl-1H-8-oxa-1,2,6-triaza-cyclopenta[a]naphthalen-9-one

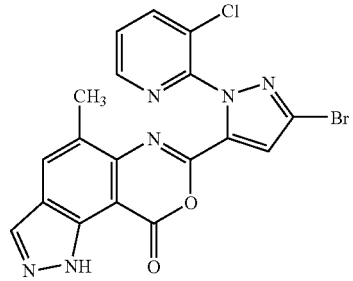 [SMILES: Cc1cc2cn[nH]c2c2c(=O)oc(-c3cc(Br)nn3-c3ncccc3Cl)nc12]

To a suspension of 700 mg (3.66 mmol) of 6-amino-5-methyl-1H-indazole-7-carboxylic acid in 26 mL of anhydrous acetonitrile is added 1.11 g (3.66 mmol) of 5-bromo- 2-(3-chloro-pyridin-2-yl)-2H-pyrazole-3-carboxylic acid followed by 1.3 mL (16.2 mmol) of pyridine. The mixture is stirred at ambient temperature during 30 minutes. Then the suspension is cooled to 0° C. and 1.0 mL (12.9 mmol) of methanesulfonyl chloride is added drop wise. The mixture is stirred at ambient temperature for 16 hours. Then the solvent is evaporated and the residue is triturated with a minimum of cold water. The precipitate, which is formed is filtrated, washed with cold water and dried. The pale yellowish product obtained (1.6 g) is engaged in the next step; LC/MS:459/461 (M+H)+.

b) Preparation of 6-{[5-bromo-2-(3-chloro-pyridin-2-yl)-2H-pyrazole-3-carbonyl]-amino}-5-methyl-1H-indazole-7-carboxylic acid isopropylamide

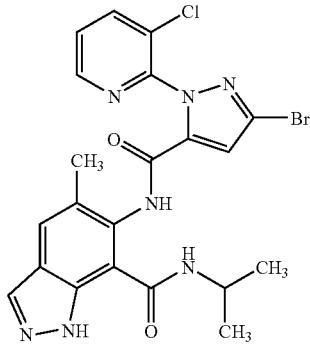

To a suspension of 600 mg of the above 7-[5-bromo-2-(3-chloro-pyridin-2-yl)-2H-pyrazol-3-yl]-5-methyl-1H-8-oxa-1,2,6-triaza-cyclopenta[a]naphthalen-9-one in 10 mL of acetonitrile/water (4:1, v/v) is added 1.11 mL (13.1 mmol) of isopropylamine. The reaction mixture is stirred for 9 hours at ambient temperature and then concentrated in vacuo. The residue is taken-up with brine and ethyl acetate. The phases are separated and the aqueous layer is washed with ethyl acetate. The combined organic layers are washed with brine, dried over MgSO4 and concentrated in vacuo. Purification of the residue by flash chromatography (SiO2, hexane/ethyl acetate 1:2) affords 110 mg (16% over two steps) of the product as a white solid; LC/MS:518/520 (M+H)+, m.p.: 163-166° C.

Example 32

Preparation of 6-{[5-bromo-2-(3-chloro-pyridin-2-yl)-2H-pyrazole-3-carbonyl]-amino}-5-methyl-1H-indazole-7-carboxylic acid bicyclopropyl-1-ylamide

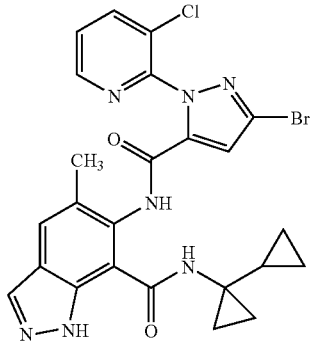 [SMILES: Cc1cc2cn[nH]c2c(C(=O)NC2(C3CC3)CC2)c1NC(=O)c1cc(Br)nn1-c1ncccc1Cl]

See example 28 for the preparation of this compound with 7-[5-bromo-2-(3-chloro-pyridin-2-yl)-2H-pyrazol-3-yl]-5-methyl-1H-8-oxa-1,2,6-triaza-cyclopenta[a]naphthalen-9-one as the starting material. The reaction is stirred at 50° C. for 27 hours and then concentrated in vacuo. Purification of the residue by flash chromatography (SiO2, hexane/ethyl acetate 1:2) and crystallisation in hexanes affords 20 mg (5% over two steps) of the product as a white solid; LC/MS:556/558 (M+H)+, m.p.: 170-173° C.

Example 33

Preparation of 6-{[2-(3-chloro-pyridin-2-yl)-5-difluoromethyl-2H-pyrazole-3-carbonyl]-amino}-5-methyl-1H-indazole-7-carboxylic acid isopropylamide a) Preparation of 7-[2-(3-chloro-pyridin-2-yl)-5-difluoromethyl-2H-pyrazol-3-yl]-5-methyl-1H-8-oxa-1,2,6-triaza-cyclopenta[a]naphthalen-9-one

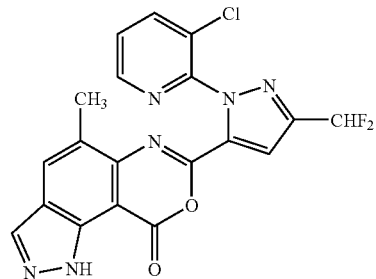 [SMILES: Cc1cc2cn[nH]c2c2c(=O)oc(-c3cc(C(F)F)nn3-c3ncccc3Cl)nc12]

To a suspension of 540 mg (2.82 mmol) of 6-amino-5-methyl-1H-indazole-7-carboxylic acid in 20 mL of anhydrous acetonitrile is added 771 mg (2.82 mmol) of 2-(3-chloro-pyridin-2-yl)-5-difluoromethyl-2H-pyrazole-3-carboxylic acid followed by 1.02 mL (12.7 mmol) of pyridine. The mixture is stirred at ambient temperature during 30 minutes. Then the suspension is cooled to 0° C. and 766 µL (9.9 mmol) of methanesulfonyl chloride is added dropwise. The mixture is stirred at 50° C. for 16 hours. Then the solvent is evaporated and the residue is triturated with a minimum of cold water. The precipitate, which is formed is filtrated, washed with cold water and dried. The pale yellowish product obtained is engaged in the next step; LC/MS:429/431 (M+H)+.

b) Preparation of 6-{[2-(3-chloro-pyridin-2-yl)-5-difluoromethyl-2H-pyrazole-3-carbonyl]-amino}-5-methyl-1H-indazole-7-carboxylic acid isopropylamide

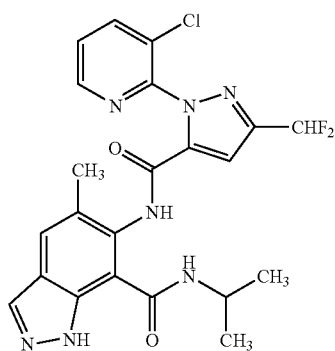 [SMILES: Cc1cc2cn[nH]c2c(C(=O)NC(C)C)c1NC(=O)c1cc(C(F)F)nn1-c1ncccc1Cl]

To a suspension of 600 mg of the above 7-[2-(3-chloro-pyridin-2-yl)-5-difluoromethyl-2H-pyrazol-3-yl]-5-methyl- 1H-8-oxa-1,2,6-triaza-cyclopenta[a]naphthalen-9-one in 10 mL of acetonitrile/water (4:1, v/v), is added 1.2 mL (14.0 mmol) of isopropylamine. The reaction mixture is stirred for 6 hours at ambient temperature and then concentrated in vacuo. The residue is taken-up with brine and ethyl acetate. The phases are separated and the aqueous layer is washed with ethyl acetate. The combined organic layers are washed with brine, dried over MgSO$_4$ and concentrated in vacuo. Trituration of the residue in ethyl acetate affords 106 mg (15% over two steps) of the product as a pale yellowish solid; LC/MS:488/490 (M+H)$^+$; m.p.: 250-253° C.

Example 34

Preparation of 6-{[2-(3-chloro-pyridin-2-yl)-5-trifluoromethyl-2H-pyrazole-3-carbonyl]-amino}-5-ethynyl-1H-indazole-7-carboxylic acid isopropylamide a) Preparation of 6-amino-5-trimethylsilanylethynyl-1H-indazole-7-carboxylic acid methyl ester

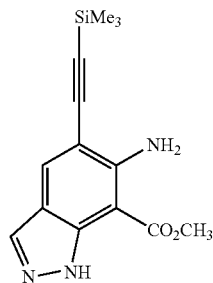 [SMILES: COC(=O)c1c(N)c(C#C[Si](C)(C)C)cc2cn[nH]c12]

To a solution of 1.5 g (5.6 mmol) of 6-amino-5-bromo-1H-indazole-7-carboxylic acid methyl ester, prepared as in step a in example 16, in 3 mL of N,N-dimethylformamide under an atmosphere of argon is added 785 μL (5.6 mmol) of trimethylsilylacetylene, 8.65 mL of diethylamine (83.2 mmol), 194 mg (0.28 mmol) of dichlorobis(triphenylphosphine)palladium II and 53 mg (0.28 mmol) of copper iodide. The reaction mixture is stirred in a microwave oven at 150° C. for 5 minutes, filtrated over Celite (washing with ethyl actetate) and concentrated in vacuo. The residue is purified by flash chromatography (SiO$_2$, hexane/ethyl acetate 2:1) to afford 970 mg of the product (61%) as a yellowish solid; LC/MS:288/289 (M+H)$^+$.

b) Preparation of 6-amino-5-ethynyl-1H-indazole-7-carboxylic acid methyl ester

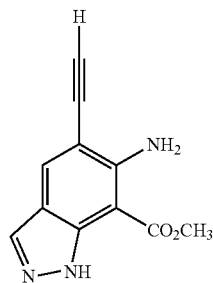 [SMILES: C#Cc1cc2cn[nH]c2c(C(=O)OC)c1N]

To a solution of 500 mg (1.74 mmol) of 6-amino-5-trimethylsilanylethynyl-1H-indazole-7-carboxylic acid methyl ester in 17 mL of anhydrous tetrahydrofuran under an atmosphere of argon is added 2.6 mL (2.6 mmol) of a 1 M solution tetrabutylamonium fluoride in tetrahydrofuran. The reaction mixture is stirred at ambient temperature for 2 hours. Water and tert-butylmethylether are added and the two phases are separated. The aqueous layer is extracted with tert-butylmethylether. The combined organic extracts are washed with brine, dried over MgSO$_4$ and concentrated in vacuo. The residue is suspended in hexanes. Filtration affords 210 mg (56%) of the product as a yellowish solid; LC/MS:216/217 (M+H)$^+$.

c) Preparation of 6-amino-5-ethynyl-1H-indazole-7-carboxylic acid

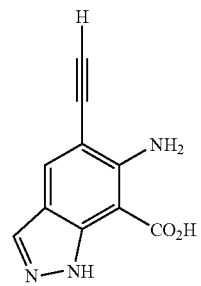 [SMILES: C#Cc1cc2cn[nH]c2c(C(=O)O)c1N]

To a solution of 200 mg (0.93 mmol) of 6-amino-5-ethynyl-1H-indazole-7-carboxylic acid methyl ester in 4.2 mL of dioxane and 0.2 mL of methanol is added 2.3 mL (2.3 mmol) of a 1N aqueous solution of NaOH. The mixture is stirred for 5 hours at 50° C. The solvents are evaporated and water is added to the residue. The product is precipitated at pH 4 by addition of 1N aqueous HCl, filtrated, washed with a minimum of water and dried by azeotropic distillation with toluene. The yellowish solid obtained is used directly in the next step; LC/MS: 202/203 (M+H)$^+$.

d) Preparation of 7-[2-(3-chloro-pyridin-2-yl)-5-trifluoromethyl-2H-pyrazol-3-yl]-5-ethynyl-1H-8-oxa-1,2,6-triaza-cyclopenta[a]naphthalen-9-one

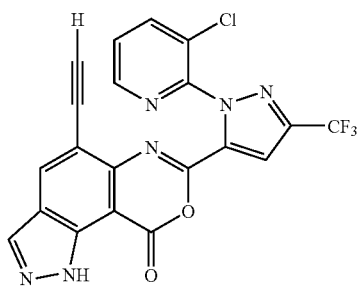 [SMILES: C#Cc1cc2cn[nH]c2c2c(=O)oc(-c3cc(C(F)(F)F)nn3-c3ncccc3Cl)nc12]

To a suspension of 200 mg (0.99 mmol) of 6-amino-5-ethynyl-1H-indazole-7-carboxylic acid in 7 mL of anhydrous acetonitrile is added 290 mg (0.99 mmol) of 2-(3-chloropyridin-2-yl)-5-triluoromethyl-2H-pyrazole-3-carboxylic acid followed by 360 μL (4.5 mmol) of pyridine. The mixture is stirred at ambient temperature during 30 minutes. Then the suspension is cooled to 0° C. and 270 μL (3.5 mmol) of methanesulfonyl chloride is added dropwise. The resulting mixture is stirred at ambient temperature for 16 hours. Then the solvent is evaporated and the residue is triturated with a minimum of cold water. The precipitate, which is formed is filtrated and washed with cold water. The pale yellowish product obtained (426 mg) is engaged in the next step; LC/MS:457/459 (M+H)+.

e) Preparation of 6-{[2-(3-chloro-pyridin-2-yl)-5-trifluoromethyl-2H-pyrazole-3-carbonyl]-amino}-5-cyano-1H-indazole-7-carboxylic acid isopropylamide

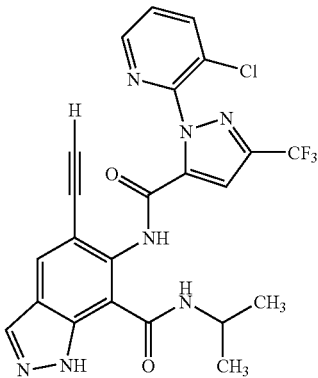 [SMILES: C#Cc1cc2cn[nH]c2c(C(=O)NC(C)C)c1NC(=O)c1cc(C(F)(F)F)nn1-c1ncccc1Cl]

To a mixture of 426 mg of the above 7-[2-(3-chloro-pyridin-2-yl)-5-trifluoromethyl-2H-pyrazol-3-yl]-5-ethynyl-1H-8-oxa-1,2,6-triaza-cyclopenta[a]naphthalen-9-one in 7 mL of 4:1 (v/v) mixture of acetonitrile/water is added 0.79 mL (9.3 mmol) of isopropylamine. The reaction mixture is stirred during 4 hours at ambient temperature and then concentrated in vacuo. After purification by flash chromatography (SiO₂, hexane/ethyl acetate 4:1), 250 mg (38%) of product are obtained as a yellow solid; LC/MS:516/518 (M+H)+; m.p.: 226-229° C.

Example 35

Preparation of 6-{[2-(3-chloro-pyridin-2-yl)-5-trifluoromethyl-2H-pyrazole-3-carbonyl]-amino}-5-ethynyl-1H-indazole-7-carboxylic acid bicyclopropyl-1-ylamide

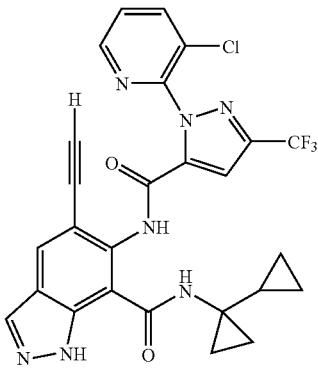 [SMILES: C#Cc1cc2cn[nH]c2c(C(=O)NC2(C3CC3)CC2)c1NC(=O)c1cc(C(F)(F)F)nn1-c1ncccc1Cl]

To a solution of 530 mg of the above 7-[2-(3-chloro-pyridin-2-yl)-5-trifluoromethyl-2H-pyrazol-3-yl]-5-ethynyl-1H-8-oxa-1,2,6-triaza-cyclopenta[a]naphthalen-9-one in 10 mL of N,N-dimethylformamide, is added 465 mg (3.48 mmol) of bicyclopropyl-1-ylamine hydrochloride and 485 µL (3.48 mmol) of triethylamine. The mixture is stirred at 50° C. for 16 hours and then concentrated in vacuo. Purification of the residue by flash chromatography (SiO₂, hexane/ethyl acetate 3:7) affords 200 mg (31% over two steps) of the product as white solid; LC/MS:554/556 (M+H)+, m.p.: 246-248° C.

Example 36

Preparation of 5-chloro-6-{[5-chloro-2-(3-chloro-pyridin-2-yl)-2H-pyrazole-3-carbonyl]-amino}-1H-indazole-7-carboxylic acid isopropylamide a) Preparation of 5-chloro-7-[5-chloro-2-(3-chloro-pyridin-2-yl)-2H-pyrazol-3-yl]-1H-8-oxa-1,2,6-triaza-cyclopenta[a]naphthalen-9-one

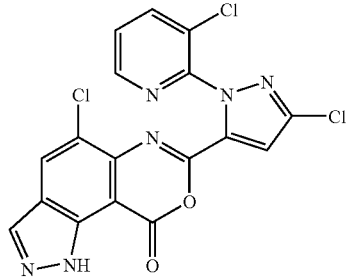 [SMILES: O=c1oc(-c2cc(Cl)nn2-c2ncccc2Cl)nc2c(Cl)cc3cn[nH]c3c12]

To a suspension of 1.00 g (4.58 mmol) of 6-amino-5-chloro-1H-indazole-7-carboxylic acid in 40 mL of anhydrous acetonitrile is added 1.18 g (4.58 mmol) of 5-chloro-2-(3-chloro-pyridin-2-yl)-2H-pyrazole-3-carboxylic acid followed by 1.7 mL (20.6 mmol) of pyridine. The mixture is stirred at ambient temperature during 30 minutes. Then the suspension is cooled to 0° C. and 1.25 mL (16.0 mmol) of methanesulfonyl chloride is added dropwise. The mixture is stirred at ambient temperature for 6 hours. Then the solvent is evaporated and the residue is triturated with a minimum of cold water. The precipitate, which is formed is filtrated, washed with cold water and dried. Purification by flash chromatography (SiO₂, toluene/methylene chloride/ethyl acetate 10:10:3) affords 910 mg (39%) of the product as a yellowish solid; LC/MS:433/435 (M+H)+.

b) Preparation of 5-chloro-6-{[5-chloro-2-(3-chloro-pyridin-2-yl)-2H-pyrazole-3-carbonyl]-amino}-1H-indazole-7-carboxylic acid isopropylamide

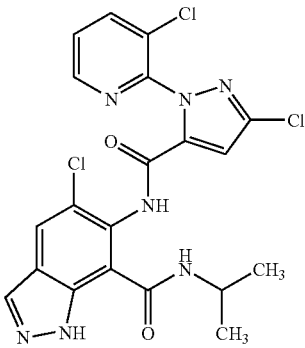 [SMILES: CC(C)NC(=O)c1c(NC(=O)c2cc(Cl)nn2-c2ncccc2Cl)c(Cl)cc2cn[nH]c12]

To a suspension of 210 mg (0.40 mmol) of the above 5-chloro-7-[5-chloro-2-(3-chloro-pyridin-2-yl)-2H-pyrazol-3-yl]-1H-8-oxa-1,2,6-triaza-cyclopenta[a]naphthalen-9-one in 4.2 mL of tetrahydrofuran is added 110 µl (1.3 mmol) of isopropylamine. The reaction mixture is stirred for 4 hours at ambient temperature and then concentrated in vacuo. The residue is Purification of the residue by reverse-phase chromatography affords 111 mg (52%) of the product as a white solid; LC/MS:514/516 (M+Na)+.

Example 37

Preparation of 5-chloro-6-{[5-chloro-2-(3-chloro-pyridin-2-yl)-2H-pyrazole-3-carbonyl]-amino}-1H-indazole-7-carboxylic acid bicyclopropyl-1-ylamide

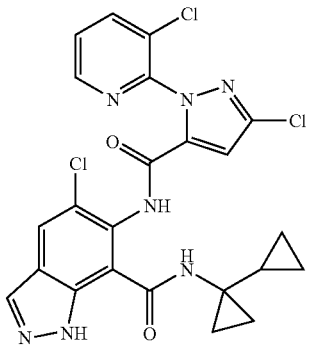 [SMILES: O=C(NC1(C2CC2)CC1)c1c(NC(=O)c2cc(Cl)nn2-c2ncccc2Cl)c(Cl)cc2cn[nH]c12]

To a solution of 400 mg (0.78 mmol) of the above 5-chloro-7-[5-chloro-2-(3-chloro-pyridin-2-yl)-2H-pyrazol-3-yl]-1H-8-oxa-1,2,6-triaza-cyclopenta[a]naphthalen-9-one in 8 mL of N,N-dimethylformamide is added 262 mg (1.96 mmol) of bicyclopropyl-1-ylamine hydrochloride and 273 µL (1.96 mmol) of triethylamine. The reaction is stirred at 50° C. for 16 hours and then concentrated in vacuo. The residue is taken-up with water and tert-butylmethylether. The phases are separated and the aqueous layer is washed twice with tert-butyl-methylether. The combined organic layers are washed with brine, dried over MgSO$_4$ and concentrated in vacuo. Purification of the residue by flash chromatography (SiO$_2$, hexanes/ethyl acetate 1:1 to 1:2, gradient) affords 380 mg (91%) of the product as a white solid; LC/MS:530/532 (M+H)$^+$, m.p.: 173-175° C.

Example 38

Preparation of 5-chloro-6-{[2-(3-chloro-pyridin-2-yl)-5-methoxy-2H-pyrazole-3-carbonyl]-amino}-1H-indazole-7-carboxylic acid (3-methyl-1,1-dioxo-1lambda*6*-thietan-3-yl)-amide a) Preparation of 5-chloro-7-[2-(3-chloro-pyridin-2-yl)-5-methoxy-2H-pyrazol-3-yl]-1H-8-oxa-1,2,6-triaza-cyclopenta[a]naphthalen-9-one

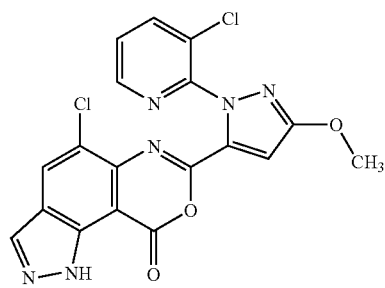 [SMILES: COc1cc(-c2nc3c(Cl)cc4cn[nH]c4c3c(=O)o2)n(-c2ncccc2Cl)n1]

To a suspension of 400 mg (1.89 mmol) of 6-amino-5-chloro-1H-indazole-7-carboxylic acid in 16 mL of anhydrous tetrahydrofuran is added 479 mg (1.89 mmol) of 2-(3-chloro-pyridin-2-yl)-5-methoxy-2H-pyrazole-3-carboxylic acid followed by 684 µL (8.50 mmol) of pyridine. The mixture is stirred at ambient temperature during 30 minutes. Then the suspension is cooled to 0° C. and 516 µL (6.66 mmol) of methanesulfonyl chloride are added dropwise. The mixture is stirred at ambient temperature for 5 hours. Then the solvent is evaporated and the residue is triturated with a minimum of cold water. The precipitate, which is formed is filtrated and washed with cold water. The pale yellowish product obtained (870 mg) is engaged in the next step; LC/MS:530/532 (M+H)$^+$.

b) Preparation of 5-chloro-6-{[2-(3-chloro-pyridin-2-yl)-5-methoxy-2H-pyrazole-3-carbonyl]-amino}-1H-indazole-7-carboxylic acid (3-methyl-thietan-3-yl)-amide

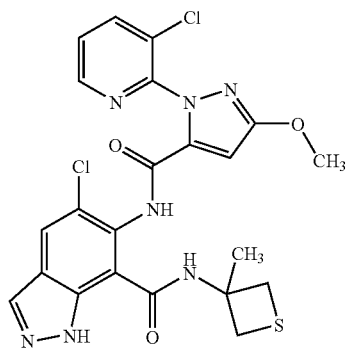 [SMILES: COc1cc(C(=O)Nc2c(Cl)cc3cn[nH]c3c2C(=O)NC2(C)CSC2)n(-c2ncccc2Cl)n1]

To a solution of 500 mg (1.16 mmol) of the above 5-chloro-7-[2-(3-chloro-pyridin-2-yl)-5-methoxy-2H-pyrazol-3-yl]-1H-8-oxa-1,2,6-triaza-cyclopenta[a]naphthalen-9-one in 10 mL of N,N-dimethylformamide is added 396 mg (3.49 mmol) of 3-methyl-thietan-3-ylamine. The reaction is stirred at 60° C. for 72 hours and then concentrated in vacuo. The residue is taken-up with water and ethyl acetate. The phases are separated and the aqueous layer is washed three times with ethyl acetate. The combined organic layers are washed with brine, dried over MgSO$_4$ and concentrated in vacuo. Purification of the residue by flash chromatography (SiO$_2$, hexanes/ethyl acetate 1:2) affords 276 mg (44%) of the product as a white solid; LC/MS:532/534 (M+H)$^+$, m.p.: 162-165° C.

c) Preparation of 5-chloro-6-{[2-(3-chloro-pyridin-2-yl)-5-methoxy-2H-pyrazole-3-carbonyl]-amino}-1H-indazole-7-carboxylic acid (3-methyl-1,1-dioxo-1lambda*6*-thietan-3-yl)-amide

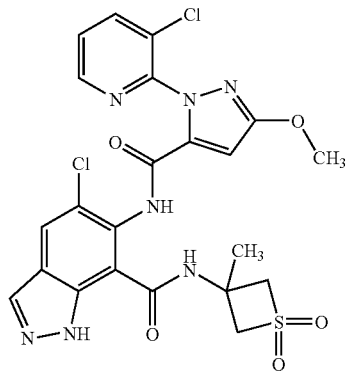 [SMILES: COc1cc(C(=O)Nc2c(Cl)cc3cn[nH]c3c2C(=O)NC2(C)CS(=O)(=O)C2)n(-c2ncccc2Cl)n1]

To a mixture of 240 mg (0.41 mmol) of 5-chloro-6-{[2-(3-chloro-pyridin-2-yl)-5-methoxy-2H-pyrazole-3-carbonyl]-amino}-1H-indazole-7-carboxylic acid (3-methyl-thietan-3- yl)-amide in 16.8 mL of methylene chloride at ambient temperature is added dropwise 300 mg (1.22 mmol) of m-chloroperbenzoic acid dissolved in 2.0 mL of methylene chloride. The mixture is stirred at ambient temperature for 16 hours. The solvent is then evaporated and ethyl acetate and aqueous saturated sodium bicarbonate are added. The phases are separated and the aqueous layer is washed with ethyl acetate. The combined organic layers are washed with brine, dried over MgSO$_4$ and concentrated in vacuo. Purification of the residue by flash chromatography (SiO$_2$, ethyl acetate) affords 115 mg (50%) of the product as a white solid; LC/MS: 564/566 (M+H)$^+$; m.p.: 167-170° C.

Example 39

Preparation of 3-bromo-5-chloro-6-{[2-(3-chloro-pyridin-2-yl)-5-methoxy-2H-pyrazole-3-carbonyl]-amino}-1H-indazole-7-carboxylic acid isopropyl-amide a) Preparation of 6-amino-3-bromo-5-chloro-1H-indazole-7-carboxylic acid methyl ester

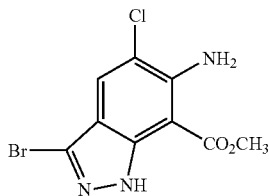 [SMILES: COC(=O)c1c(N)c(Cl)cc2c(Br)n[nH]c12]

To a solution of 9 g (29.92 mmol) of 6-amino-5-chloro-1H-indazole-7-carboxylic acid methyl ester in 68 mL of acetic acid at 80° C., is added dropwise 2 mL (38.89 mmol) of bromine. The mixture is stirred over the night at 80° C. The solvents are evaporated and water is added to the residue. The product is precipitated at pH 5 by addition of 1N aqueous NaOH, filtrated, washed with a minimum of water and dried under high vacuum. 1 g (3.28 mmol, 11%) of pure product is obtained; LC/MS:305/306 (M+H)$^+$.

b) Preparation of 6-amino-3-bromo-5-chloro-1H-indazole-7-carboxylic acid

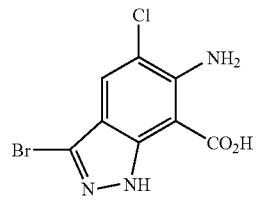 [SMILES: Nc1c(Cl)cc2c(Br)n[nH]c2c1C(=O)O]

See step b example 1 for the preparation of this compound with 6-amino-3-bromo-5-chloro-1H-indazole-7-carboxylic acid methyl ester as starting material. After 24 h of reaction time at ambient temperature, the solvents are evaporated and water is added to the residue. The product is precipitated at pH 4 by addition of concentrated HCl, filtrated, washed with a minimum of water and dried on high vacuum pump. The crude solid (832 mg) obtained is used directly in the next step; LC/MS:291/292 (M+H)$^+$.

c) Preparation of 3-bromo-5-chloro-7-[2-(3-chloro-pyridin-2-yl)-5-methoxy-2H-pyrazol-3-yl]-1H-8-oxa-1,2,6-triaza-cyclopenta[a]naphthalen-9-one

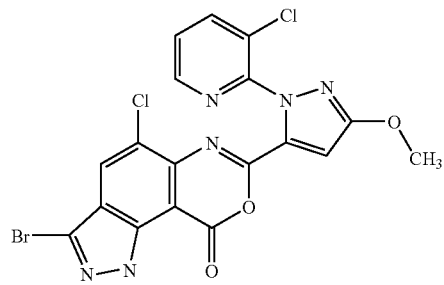 [SMILES: COc1cc(-c2nc3c(Cl)cc4c(Br)n[nH]c4c3c(=O)o2)n(-c2ncccc2Cl)n1]

To a suspension of 400 mg (1.38 mmol) of 6-amino-3-bromo-5-chloro-1H-indazole-7-carboxylic acid in 16 mL of anhydrous tetrahydrofuran at 10° C., is added 349 mg (1.38 mmol) of 2-(3-chloro-pyridin-2-yl)-5-methoxy-2H-pyrazole-3-carboxylic acid followed by 499 µL (6.20 mmol) of pyridine. Then the suspension is cooled to 0° C. and 376 µL (4.82 mmol) of methanesulfonyl chloride are added dropwise. The mixture is stirred at ambient temperature over the night. The reaction is not complete and therefore 166 µL (2.07 mmol) of pyridine are added followed by 349 mg (1.38 mmol) of 2-(3-chloro-pyridin-2-yl)-5-methoxy-2H-pyrazole-3-carboxylic acid. The reaction is stirred again at ambient temperature for 5 hours. Then the solvent is evaporated and the residue is triturated with a minimum of cold water. The precipitate, which is formed is filtrated and washed with cold water. The pale yellowish product obtained is purified by flash chromatography (SiO$_2$, heptane/ethyl acetate 1:1) affords 200 mg (0.47 mmol, 34%) of the product as a solid; LC/MS: 509/511 (M+H)$^+$.

d) Preparation of 3-bromo-5-chloro-6-{[2-(3-chloro-pyridin-2-yl)-5-methoxy-2H-pyrazole-3-carbonyl]-amino}-1H-indazole-7-carboxylic acid isopropyl-amide

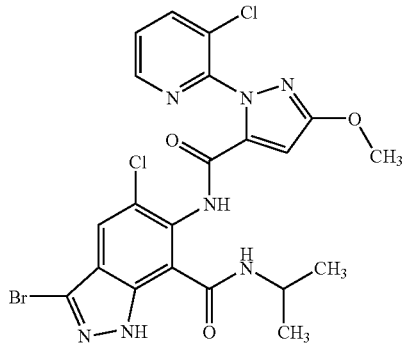 [SMILES: COc1cc(C(=O)Nc2c(Cl)cc3c(Br)n[nH]c3c2C(=O)NC(C)C)n(-c2ncccc2Cl)n1]

To a suspension of 120 mg (0.24 mmol) of the above 3-bromo-5-chloro-7-[2-(3-chloro-pyridin-2-yl)-5-methoxy-2H-pyrazol-3-yl]-1H-8-oxa-1,2,6-triaza-cyclopenta[a]naphthalen-9-one in 2.4 mL of a mixture acetonitrile:H$_2$O 4:2 (v/v) is added 60 µL (0.71 mmol) of isopropylamine. The reaction mixture is stirred for 6 hours at ambient temperature. Brine is then added to the mixture and the product is extracted with ethyl acetate (3 times). The regrouped organic phases are dried on Na$_2$SO$_4$, filtrated and evaporated. The purification of the residue by flash chromatography (SiO$_2$, heptane/ethyl acetate 1:2) affords 56 mg (42%) of a white solid; LC/MS: 568/570 (M+H)⁺, m.p.: 217-218° C.

Example 40

Preparation of 3-bromo-5-chloro-6-{[2-(3-chloro-pyridin-2-yl)-5-methoxy-2H-pyrazole-3-carbonyl]-amino}-1H-indazole-7-carboxylic acid bicyclopropyl-1-ylamide

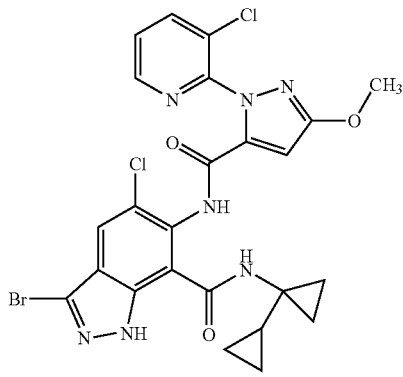 [SMILES: COc1cc(C(=O)Nc2c(Cl)cc3c(Br)n[nH]c3c2C(=O)NC2(C3CC3)CC2)n(-c2ncccc2Cl)n1]

To a solution of 120 mg (0.24 mmol) of the above 3-bromo-5-chloro-7-[2-(3-chloro-pyridin-2-yl)-5-methoxy-2H-pyrazol-3-yl]-1H-8-oxa-1,2,6-triaza-cyclopenta[a]naphthalen-9-one in 2.4 mL of N,N-dimethylformamide is added 95 mg (0.71 mmol) of bicyclopropyl-1-ylamine hydrochloride and 99 μL (0.71 mmol) of triethylamine. The reaction is stirred at 50° C. for 24 hours and then concentrated in vacuo. The residue is taken-up with acetone and after filtration the filtrate is evaporated. Purification of the residue by flash chromatography (SiO₂, hexanes/ethyl acetate 1:1) affords 80 mg (56%) of a solid; LC/MS:606/608 (M+H)⁺, m.p.: 190-194° C.

Example 41

Preparation of 5-chloro-6-{[2-(3-chloro-pyridin-2-yl)-5-trifluoromethyl-2H-pyrazole-3-carbonyl]-amino}-3-methyl-1H-indazole-7-carboxylic acid isopropylamide a) Preparation of 6-amino-5-chloro-3-methyl-1H-indazole-7-carboxylic acid methyl ester

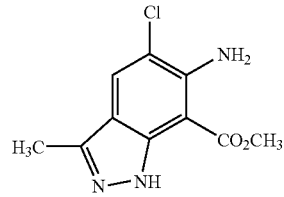 [SMILES: COC(=O)c1c(N)c(Cl)cc2c(C)n[nH]c12]

To a solution of 899 mg (5.91 mmol) of 9-methoxy-9-borabicyclo[3.3.1]nonane in 5 mL of anhydrous tetrahydrofuran is added dropwise 3.71 mL (5.91 mmol) of a solution 1N of methyl lithium in diethylether. After few minutes of stirring, a mixture of 6-amino-3-bromo-5-chloro-1H-indazole-7-carboxylic acid methyl ester, prepared as in step a in example 39, and 104 mg (0.15 mmol) of bis(triphenylphosphine) palladiumI(II) dichloride in 10 mL of anhydrous tetrahydrofuran is added. The reaction mixture is stirred in a microwave oven at 150° C. for 15 minutes. After filtration over Celite and concentration in vacuo, the residue is purified by flash chromatography (SiO₂, hexanes/ethyl acetate 1:1) to afford 470 mg of product (66%) as a pale yellowish solid; LC/MS:240/242 (M+H)⁺.

b) Preparation of 6-amino-5-chloro-3-methyl-1H-indazole-7-carboxylic acid

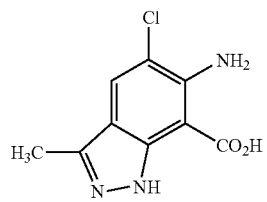

See step b example 1 for the preparation of this compound with 6-amino-5-chloro-3-methyl-1H-indazole-7-carboxylic acid methyl ester as starting material. After 24 h of reaction time at ambient temperature, the solvents are evaporated and water is added to the residue. The product is precipitated at pH 4 by addition of concentrated HCl, filtrated, washed with a minimum of water and dried on high vacuum pump. The crude solid (92%) obtained is used directly in the next step; LC/MS:226/228 (M+H)⁺.

c) Preparation of 5-chloro-7-[2-(3-chloro-pyridin-2-yl)-5-trifluoromethyl-2H-pyrazol-3-yl]-3-methyl-1H-8-oxa-1,2,6-triaza-cyclopenta[a]naphthalen-9-one

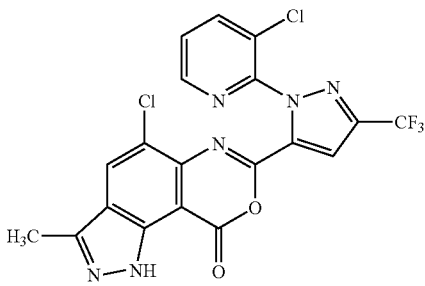 [SMILES: Cc1n[nH]c2c1cc(Cl)c1nc(-c3cc(C(F)(F)F)nn3-c3ncccc3Cl)oc(=O)c12]

To a suspension of 540 mg (2.39 mmol) of 6-amino-5-chloro-3-methyl-1H-indazole-7-carboxylic acid in 22 mL of anhydrous tetrahydrofuran at 10° C., is added 698 mg (2.39 mmol) of 2-(3-chloro-pyridin-2-yl)-5-trifluoromethyl-2H-pyrazole-3-carboxylic acid followed by 963 μL (11.97 mmol) of pyridine. Then the suspension is cooled to 0° C. and 748 μL (9.57 mmol) of methanesulfonyl chloride are added dropwise. The mixture is stirred at ambient temperature for 48 hours. Then the solvent is evaporated and the residue is taken-up with acetone. After filtration, the filtrate is evaporated in vacuo. The residue obtained is purified by flash chromatography (SiO₂, heptane/ethyl acetate 1:2) and affords 810 mg (1.68 mmol, 70%) of the product as a solid; LC/MS:481/483 (M+H)⁺.

d) Preparation of 5-chloro-6-{[2-(3-chloro-pyridin-2-yl)-5-trifluoromethyl-2H-pyrazole-3-carbonyl]-amino}-3-methyl-1H-indazole-7-carboxylic acid isopropylamide

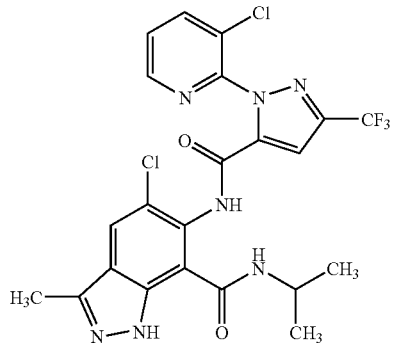 [SMILES: Cc1n[nH]c2c(C(=O)NC(C)C)c(NC(=O)c3cc(C(F)(F)F)nn3-c3ncccc3Cl)c(Cl)cc12]

To a suspension of 148 mg (0.20 mmol) of the above 5-chloro-7-[2-(3-chloro-pyridin-2-yl)-5-trifluoromethyl-2H-pyrazol-3-yl]-3-methyl-1H-8-oxa-1,2,6-triaza-cyclopenta[a]naphthalen-9-one in 5.92 mL of a mixture acetonitrile: H$_2$O 4:1 (v/v) is added 51 µL (0.60 mmol) of isopropylamine. The reaction mixture is stirred for 6 hours at ambient temperature. Brine is then added to the mixture and the product is extracted with ethyl acetate (3 times). The regrouped organic phases are dried on Na$_2$SO$_4$, filtrated and evaporated. The purification of the residue by flash chromatography (SiO$_2$, heptane/ethyl acetate 1:1) affords 30 mg (28%) of a white solid; LC/MS:540/542 (M+H)$^+$, m.p.: 235-236° C.

Example 42

Preparation of 5-chloro-6-{[2-(3-chloro-pyridin-2-yl)-5-trifluoromethyl-2H-pyrazole-3-carbonyl]-amino}-3-methyl-1H-indazole-7-carboxylic acid bicyclopropyl-1-ylamide

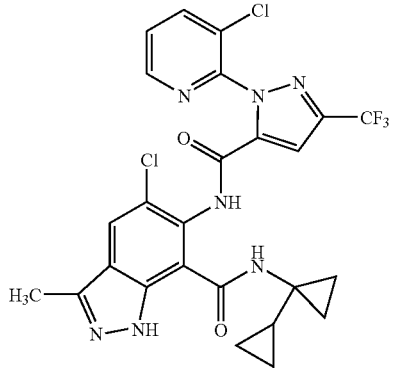 [SMILES: Cc1n[nH]c2c(C(=O)NC3(C4CC4)CC3)c(NC(=O)c3cc(C(F)(F)F)nn3-c3ncccc3Cl)c(Cl)cc12]

To a solution of 150 mg (0.25 mmol) of the above 5-chloro-7-[2-(3-chloro-pyridin-2-yl)-5-trifluoromethyl-2H-pyrazol-3-yl]-3-methyl-1H-8-oxa-1,2,6-triaza-cyclopenta[a]naphthalen-9-one in 3 mL of N,N-dimethylformamide is added 100 mg (0.75 mmol) of bicyclopropyl-1-ylamine hydrochloride and 104 µL (0.75 mmol) of triethylamine. The reaction is stirred at 50° C. for 24 hours and then concentrated in vacuo. The residue is taken-up with acetone and after filtration the filtrate is evaporated. Purification of the residue by flash chromatography (SiO$_2$, hexanes/ethyl acetate 3:2) affords 70 mg (48%) of a solid; LC/MS:578/580 (M+H)$^+$, m.p.: 228-229° C.

Example 43

Preparation of 6-chloro-7-{[2-(3-chloro-pyridin-2-yl)-5-trifluoromethyl-2H-pyrazole-3-carbonyl]-amino}-quinoline-8-carboxylic acid isopropylamide a) Preparation of 7-amino-quinoline-8-carboxylic acid

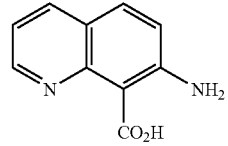

This compound is prepared as described in *Chem. Pharm. Bull.* 1985, 33, 4, 1360 and *J. Med. Chem.*, 2002, 45, 3692; LC/MS:189/190 (M+H)$^+$. The starting material 7-nitro-quinoline is prepared as in U.S. Pat. No. 5,283,336 (1994) and WO03068749.

b) Preparation of 2-[2-(3-chloro-pyridin-2-yl)-5-trifluoromethyl-2H-pyrazol-3-yl]-3-oxa-1,5-diaza-phenanthren-4-one

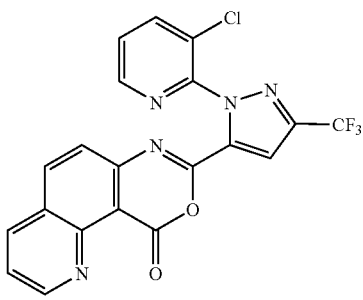 [SMILES: O=c1oc(-c2cc(C(F)(F)F)nn2-c2ncccc2Cl)nc2ccc3cccnc3c12]

To a suspension of 500 mg (2.66 mmol) of 7-amino-quinoline-8-carboxylic acid in 20 mL of anhydrous tetrahydrofuran at 10° C., is added 775 mg (2.66 mmol) of 2-(3-chloro-pyridin-2-yl)-5-trifluoromethyl-2H-pyrazole-3-carboxylic acid followed by 1.07 mL (13.28 mmol) of pyridine. Then the suspension is cooled to 0° C. and 830 µL (10.63 mmol) of methanesulfonyl chloride are added dropwise. The mixture is stirred at ambient temperature for 48 hours. Then the solvent is evaporated and the residue is precipitated with a minimum of water. The filtration gave 180 mg of product after drying on high vacuum pump. The filtrate is evaporated and the residue obtained is purified by flash chromatography to afford 100 mg more of product as a solid. The overall yield is 24%; LC/MS: 444/446 (M+H)$^+$.

c) Preparation of 7-{[2-(3-chloro-pyridin-2-yl)-5-trifluoromethyl-2H-pyrazole-3-carbonyl]-amino}-quinoline-8-carboxylic acid isopropylamide

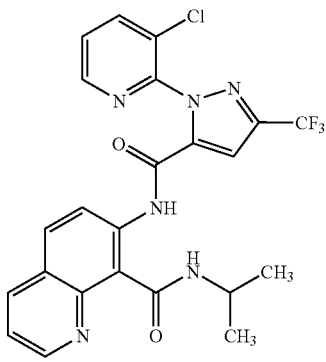 [SMILES: CC(C)NC(=O)c1c(NC(=O)c2cc(C(F)(F)F)nn2-c2ncccc2Cl)ccc2cccnc12]

To a suspension of 140 mg (0.28 mmol) of the above 2-[2-(3-chloro-pyridin-2-yl)-5-trifluoromethyl-2H-pyrazol-3-yl]-3-oxa-1,5-diaza-phenanthren-4-one in 5.60 mL of a mixture acetonitrile: H$_2$O 4:1 (v/v) is added 73 μL (0.85 mmol) of isopropylamine. The reaction mixture is stirred for 6 hours at ambient temperature. Brine is then added to the mixture and the product is extracted with ethyl acetate (3 times). The regrouped organic phases are dried on Na$_2$SO$_4$, filtrated and evaporated. The purification of the residue by flash chromatography (SiO$_2$, heptane and ethyl acetate as eluants) affords 100 mg (70%) of a white solid; LC/MS: 503/505 (M+H)$^+$, m.p.: 225-226° C.

Example 44

Preparation of 7-{[2-(3-chloro-pyridin-2-yl)-5-trifluoromethyl-2H-pyrazole-3-carbonyl]-amino}-quinoline-8-carboxylic acid methylamide

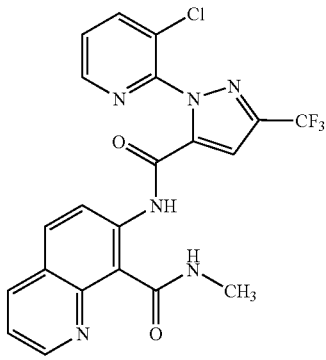 [SMILES: CNC(=O)c1c(NC(=O)c2cc(C(F)(F)F)nn2-c2ncccc2Cl)ccc2cccnc12]

To a suspension of 140 mg (0.28 mmol) of the above 2-[2-(3-chloro-pyridin-2-yl)-5-trifluoromethyl-2H-pyrazol-3-yl]-3-oxa-1,5-diaza-phenanthren-4-one in 5.60 mL of a mixture acetonitrile: H$_2$O 4:1 (v/v) is added 74 μL (0.85 mmol) of methylamine (solution 40% in water). The reaction mixture is stirred for 6 hours at ambient temperature. Brine is then added to the mixture and the product is extracted with ethyl acetate (3 times). The regrouped organic phases are dried on Na$_2$SO$_4$, filtrated and evaporated. The purification of the residue by flash chromatography (SiO$_2$, heptane and ethyl acetate as eluants) affords 84 mg (62%) of a white solid; LC/MS:475/477 (M+H)$^+$, m.p.: 219-220° C.

Example 45

Preparation of 6-{[2-(3-chloro-pyridin-2-yl)-5-trifluoromethyl-2H-pyrazole-3-carbonyl]-amino}-quinoline-5-carboxylic acid isopropylamide a) Preparation of 6-amino-quinoline-5-carboxylic acid amide

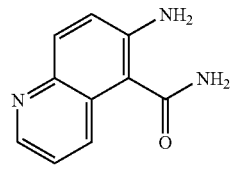 [SMILES: NC(=O)c1c(N)ccc2ncccc12]

This compound is prepared as reported in *J. Chem. Soc.*, 1962, 3645 starting from the 6-nitroquinoline. Under these conditions we didn't get the 6-amino-quinoline-5-carboxylic acid as described, but the corresponding amide; LC/MS:188/189 (M+H)$^+$.

b) Preparation of 6-amino-quinoline-5-carboxylic acid methyl ester

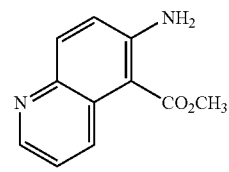 [SMILES: COC(=O)c1c(N)ccc2ncccc12]

To a solution of 2 g (10.68 mmol) of the above 6-amino-quinoline-5-carboxylic acid amide in 10.76 mL of absolute methanol is added 2.34 mL (42.73 mmol) of concentrated sulphuric acid. The reaction is stirred in a microwave during 13 minutes at 140° C. The reaction is repeated 6 times with flask opening after each run because of gas formation. The mixture is then cooled at 0° C. and water is added. The pH of the mixture is increased slowly to 6 with addition of an aqueous 6N NaOH solution. The pH is adjusted to 8 with a saturated aqueous solution of NaHCO$_3$. The product is extracted with ethyl acetate (4 times) and the combined organic layers are dried on Na$_2$SO$_4$, filtrated and evaporated. After flash chromatography purification with heptane and ethyl acetate as eluants, 555 mg (26%) of a yellowish solid are obtained; LC/MS: 203/204 (M+H)$^+$.

c) Preparation of 6-amino-quinoline-5-carboxylic acid

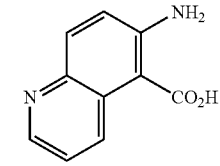

To a solution of 540 mg (2.19 mmol) of the above 6-amino-quinoline-5-carboxylic acid methyl ester in 10.8 mL of dioxane and 0.54 mL of methanol is added 5.48 mL (5.48 mmol) of an aqueous solution of NaOH 1N. The reaction is stirred 24 hours at ambient temperature. Then the solvents are evaporated in vacuo and the residue is suspended in a minimum of d) Preparation of 2-[2-(3-chloro-pyridin-2-yl)-5-trifluoromethyl-2H-pyrazol-3-yl]-3-oxa-1,8-diaza-phenanthren-4-one

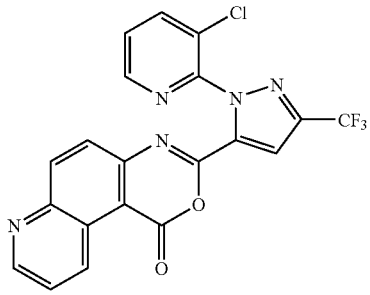 [SMILES: O=c1oc(-c2cc(C(F)(F)F)nn2-c2ncccc2Cl)nc2ccc3ncccc3c12]

To a suspension of 240 mg (1.28 mmol) of 6-amino-quinoline-5-carboxylic acid in 9.60 mL of anhydrous tetrahydrofuran at 10° C., is added 372 mg (1.28 mmol) of 2-(3-chloro-pyridin-2-yl)-5-trifluoromethyl-2H-pyrazole-3-carboxylic acid followed by 5134 (6.38 mmol) of pyridine. Then the suspension is cooled to 0° C. and 398 μL (5.10 mmol) of methanesulfonyl chloride are added dropwise. The mixture is stirred at ambient temperature for 48 hours. Then the solvent is evaporated and the residue is precipitated with a minimum of ethyl acetate and washed with ethyl acetate. After filtration, water is added to the filtrate and the new suspension formed is filtrated again. After drying on high vacuum pump 303 mg (54%) of solid are obtained; LC/MS:444/446 (M+H)$^+$.

e) Preparation of 6-{[2-(3-chloro-pyridin-2-yl)-5-trifluoromethyl-2H-pyrazole-3-carbonyl]-amino}-quinoline-5-carboxylic acid isopropylamide

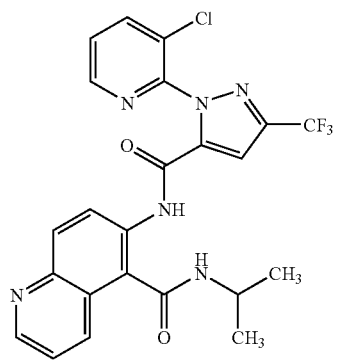 [SMILES: CC(C)NC(=O)c1c(NC(=O)c2cc(C(F)(F)F)nn2-c2ncccc2Cl)ccc2ncccc12]

To a suspension of 150 mg (0.30 mmol) of the above 2-[2-(3-chloro-pyridin-2-yl)-5-trifluoromethyl-2H-pyrazol-3-yl]-3-oxa-1,8-diaza-phenanthren-4-one in 6 mL of a mixture acetonitrile: H$_2$O 4:1 (v/v) is added 78 μL (0.91 mmol) of isopropylamine. The reaction mixture is stirred for 6 hours at ambient temperature. Brine is then added to the mixture and the product is extracted with ethyl acetate (3 times). The regrouped organic phases are dried on Na$_2$SO$_4$, filtrated and evaporated. The purification of the residue by flash chromatography (SiO$_2$, heptane/ethyl acetate 1:1) affords 100 mg (65%) of a white solid; LC/MS:503/505 (M+H)$^+$, m.p.: 182-183° C.

Example 46

Preparation of 6-{[2-(3-chloro-pyridin-2-yl)-5-trifluoromethyl-2H-pyrazole-3-carbonyl]-amino}-quinoline-5-carboxylic acid methylamide

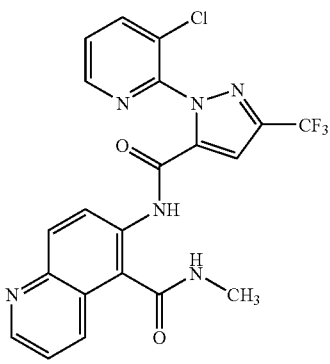 [SMILES: CNC(=O)c1c(NC(=O)c2cc(C(F)(F)F)nn2-c2ncccc2Cl)ccc2ncccc12]

To a suspension of 150 mg (0.30 mmol) of the above 2-[2-(3-chloro-pyridin-2-yl)-5-trifluoromethyl-2H-pyrazol-3-yl]-3-oxa-1,8-diaza-phenanthren-4-one in 6 mL of a mixture acetonitrile: H$_2$O 4:1 (v/v) is added 79 μL (0.91 mmol) of methylamine (solution 40% in water). The reaction mixture is stirred for 6 hours at ambient temperature. Brine is then added to the mixture and the product is extracted with ethyl acetate (3 times). The regrouped organic phases are dried on Na$_2$SO$_4$, filtrated and evaporated. The purification of the residue by flash chromatography (SiO$_2$, heptane/ethyl acetate 1:1) affords 110 mg (76%) of a white solid; LC/MS:475/477 (M+H)$^+$, m.p.: 210-211° C.

Example 47

Preparation of 6-{[2-(3-chloro-pyridin-2-yl)-5-trifluoromethyl-2H-pyrazole-3-carbonyl]-amino}-7-methyl-quinoline-5-carboxylic acid methylamide a) Preparation of 6-amino-7-bromo-quinoline-5-carboxylic acid methyl ester

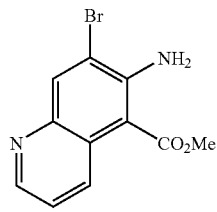 [SMILES: COC(=O)c1c(N)c(Br)cc2ncccc12]

To a mixture of 6.6 g (32.6 mmol) of 6-amino-quinoline-5-carboxylic acid methyl ester, prepared as in step b in example 45, in 50 mL of N,N-dimethylformamide is added 5.80 g (17.78 mmol) of N-bromosuccinimide. The reaction is stirred at ambient temperature for 4 hours. The solvent is then evaporated and the residue is submitted to column chromatography purification on silica gel with ethyl acetate as eluent to afford 1.59 g (17%) of the product as a yellow solid; LC/MS:281/283 (M+H)$^+$.

b) Preparation of 6-amino-7-methyl-quinoline-5-carboxylic acid methyl ester

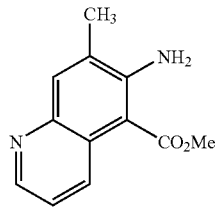 [SMILES: COC(=O)c1c(N)c(C)cc2ncccc12]

To 1.59 g (5.66 mmol) of 6-amino-7-bromo-quinoline-5-carboxylic acid methyl ester in 30 mL of dioxane under an atmosphere of argon is added 2.35 g (17.0 mmol) of $K_2CO_3$, 323 mg (0.28 mmol) of tetrakis(triphenylphsophine)palladium and 710 mg (5.66 mmol) of trimethylboroxine. The reaction mixture is stirred in a microwave oven at 180° C. for 10 minutes. After filtration over Celite and concentration in vacuo, the residue is purified by flash chromatography ($SiO_2$, ethyl acetate) y to afford 550 mg of product (45%) as a yellowish solid; LC/MS:217/218 $(M+H)^+$.

c) Preparation of 6-amino-7-methyl-quinoline-5-carboxylic acid

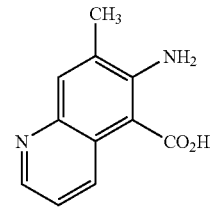

To a solution of 550 mg (2.54 mmol) of 6-amino-7-methyl-quinoline-5-carboxylic acid methyl ester in 11 mL of dioxane and 0.5 mL of methanol, is added 6.4 mL (6.4 mmol) of an aqueous solution of NaOH 1N. The mixture is stirred at ambient temperature for 16 hours. The solvents are evaporated and water is added to the residue. The product is precipitated at pH 6 by addition of concentrated HCl, filtrated, washed with a minimum of water and dried on high vacuum pump. The yellow crude solid (282 mg) obtained is used directly in the next step; LC/MS: 203/204 $(M+H)^+$.

d) Preparation of 2-[2-(3-chloro-pyridin-2-yl)-5-hydroxy-2H-pyrazol-3-yl]-10-methyl-3-oxa-1,8-diaza-phenanthren-4-one

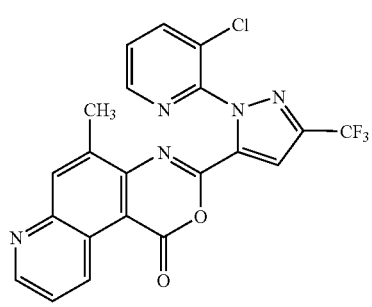 [SMILES: Cc1cc2ncccc2c2c(=O)oc(-c3cc(C(F)(F)F)nn3-c3ncccc3Cl)nc12]

To a suspension of 282 mg (1.39 mmol) of 6-amino-7-methyl-quinoline-5-carboxylic acid in 11 mL of anhydrous THF is added 407 mg (1.39 mmol) of 2-(3-chloro-pyridin-2-yl)-5-trifluoromethyl-2H-pyrazole-3-carboxylic acid followed by 560 μL (7.0 mmol) of pyridine. The mixture is stirred at ambient temperature during 30 minutes. Then the suspension is cooled to 0° C. and 430 μL (5.5 mmol) of methanesulfonyl chloride are added dropwise. The mixture is stirred at ambient temperature for 48 hours. Then the solvent is evaporated and the residue is sequentially triturated and filtrated with ethyl acetate and with a minimum of cold water. Purification of the residue by flash chromatography ($SiO_2$, heptane/ethyl acetate 1:2) affords 286 mg (45%) of the product as a yellowish solid; LC/MS:468/460 $(M+H)^+$.

e) Preparation of 6-{[2-(3-chloro-pyridin-2-yl)-5-trifluoromethyl-2H-pyrazole-3-carbonyl]-amino}-7-methyl-quinoline-5-carboxylic acid methylamide

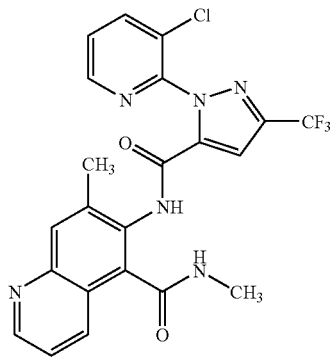 [SMILES: CNC(=O)c1c(NC(=O)c2cc(C(F)(F)F)nn2-c2ncccc2Cl)c(C)cc2ncccc12]

To a suspension of 143 mg (0.31 mmol) of the above 2-[2-(3-chloro-pyridin-2-yl)-5-hydroxy-2H-pyrazol-3-yl]-10-methyl-3-oxa-1,8-diaza-phenanthren-4-one in 5 mL of acetonitrile/water (4:1, v/v), is added 80 μL (0.9 mmol) of 40% aqueous methylamine. The reaction mixture is stirred for 6 hours at ambient temperature and then concentrated in vacuo. The residue is taken-up with brine and ethyl acetate. The phases are separated and the aqueous layer is washed twice with ethyl acetate. The combined organic layers are washed with brine, dried over $MgSO_4$ and concentrated in vacuo. Purification of the residue by flash chromatography ($SiO_2$, ethyl acetate) affords 25 mg (16%) of the product as a yellowish solid; LC/MS: 489/491 $(M+H)^+$, m.p.: 150-152° C. (decomposition).

Example 48

Preparation of 6-{[2-(3-chloro-pyridin-2-yl)-5-trifluoromethyl-2H-pyrazole-3-carbonyl]-amino}-7-methyl-quinoline-5-carboxylic acid isopropylamide

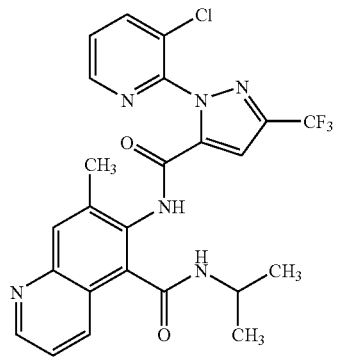 [SMILES: Cc1cc2ncccc2c(C(=O)NC(C)C)c1NC(=O)c1cc(C(F)(F)F)nn1-c1ncccc1Cl]

To a suspension of 143 mg (0.31 mmol) of the above 2-[2-(3-chloro-pyridin-2-yl)-5-hydroxy-2H-pyrazol-3-yl]-10-methyl-3-oxa-1,8-diaza-phenanthren-4-one in 5 mL of acetonitrile/water (4:1, v/v), is added 80 μL (0.9 mmol) of isopropylamine. The reaction mixture is stirred for 6 hours at ambient temperature and then concentrated in vacuo. The residue is taken-up with brine and ethyl acetate. The phases are separated and the aqueous layer is washed twice with ethyl acetate. The combined organic layers are washed with brine, dried over MgSO$_4$ and concentrated in vacuo. Purification of the residue by flash chromatography (SiO$_2$, ethyl acetate) affords 56 mg (35%) of the product as a yellowish solid; LC/MS: 517/519 (M+H)$^+$, m.p.: 162-168° C. (decomposition).

Example 49

Preparation of 6-amino-5-iodo-1H-indazole-7-carboxylic acid methyl ester

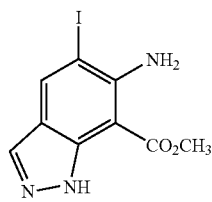 [SMILES: COC(=O)c1c(N)c(I)cc2cn[nH]c12]

To a solution of 500 mg (2.61 mmol) of 6-amino-1H-indazole-7-carboxylic acid methyl ester, prepared as in step a in example 10, in 5 mL of acetonitrile is added 1.29 g (5.73 mmol) of N-iodosuccinimide. The reaction mixture is stirred at ambient temperature for 1 hour and at 50° C. for 6 hours. The solvent is then evaporated and the residue is suspended in water. Filtration affords 750 mg (91%) of the product as a brown solid; LC/MS: 318/319 (M+H)$^+$.

TABLE P

Physical data of compounds of formula I:

| Compound No. | Structures | Melting Point | MS/NMR |
|---|---|---|---|
| P.1 | 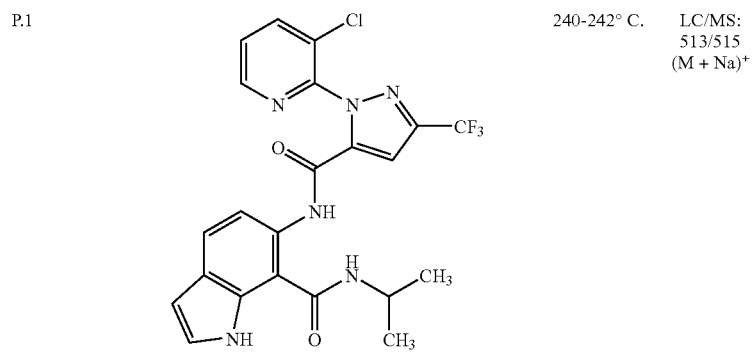<br>example 1 | 240-242° C. | LC/MS: 513/515 (M + Na)$^+$ |

TABLE P-continued
Physical data of compounds of formula I:
| Compound No. | Structures | Melting Point | MS/NMR |
|---|---|---|---|
| P.2 | 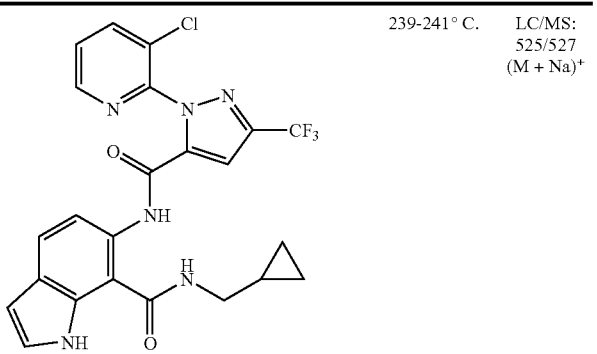 example 2 | 239-241° C. | LC/MS: 525/527 (M + Na)+ |
| P.3 | 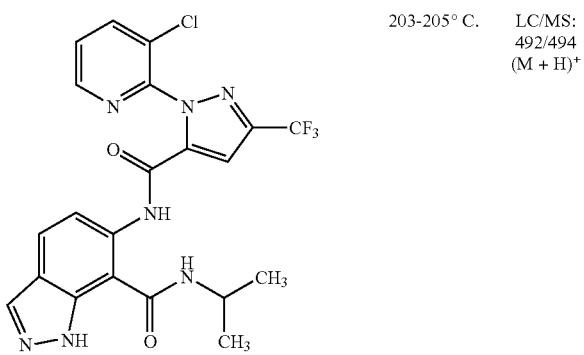 step d example 3 | 203-205° C. | LC/MS: 492/494 (M + H)+ |
| P.4 | 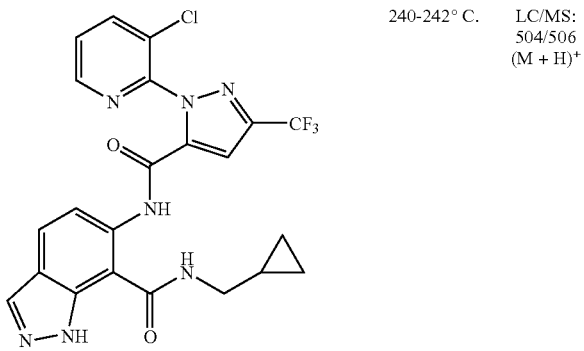 example 4 | 240-242° C. | LC/MS: 504/506 (M + H)+ |
| P.5 | 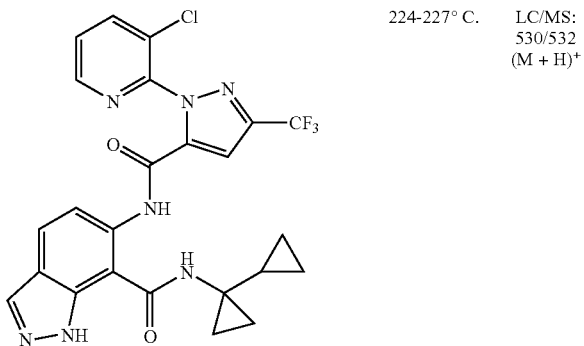 example 5 | 224-227° C. | LC/MS: 530/532 (M + H)+ |

TABLE P-continued
Physical data of compounds of formula I:
| Compound No. | Structures | Melting Point | MS/NMR |
|---|---|---|---|
| P.6 | 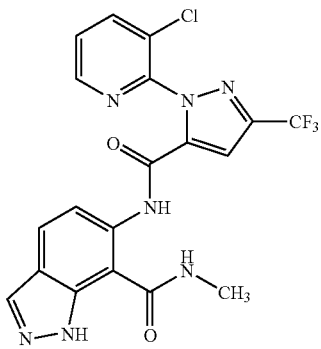<br>example 6 | 190-192° C. | LC/MS: 464/466 (M + H)+ |
| P.7 | 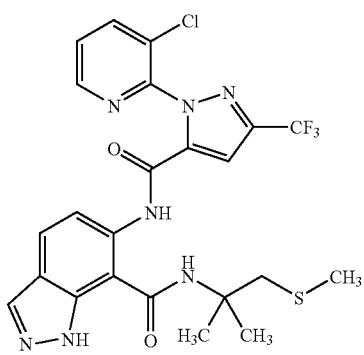<br>example 7 | 100-105° C. | LC/MS: 552/554 (M + H)+ |
| P.8 | 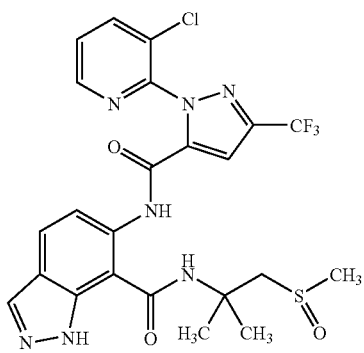<br>example 8 | — | LC/MS: 568/570 (M + H)+ |
| P.9 | 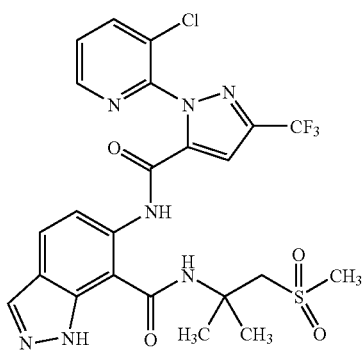<br>example 9 | — | LC/MS: 584/586 (M + H)+ |

TABLE P-continued
Physical data of compounds of formula I:
| Compound No. | Structures | Melting Point | MS/NMR |
|---|---|---|---|
| P.10 | 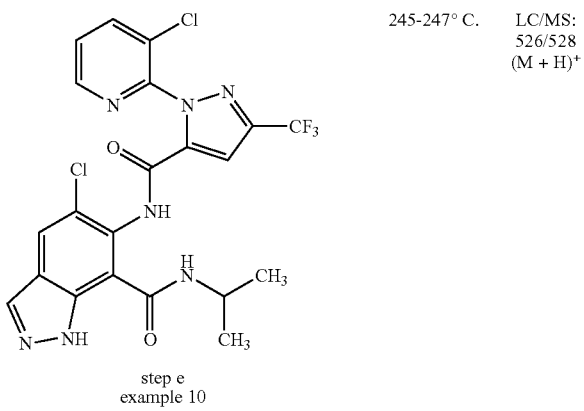 step e example 10 | 245-247° C. | LC/MS: 526/528 (M + H)+ |
| P.11 | 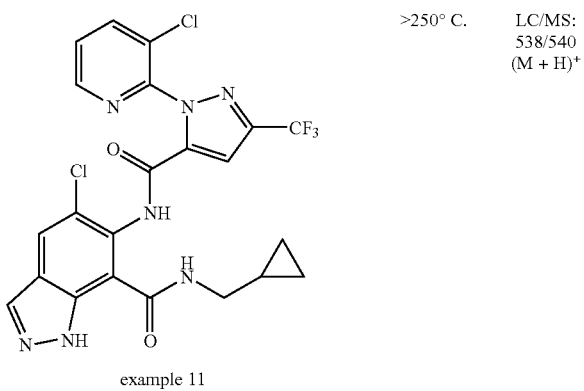 example 11 | >250° C. | LC/MS: 538/540 (M + H)+ |
| P.12 | 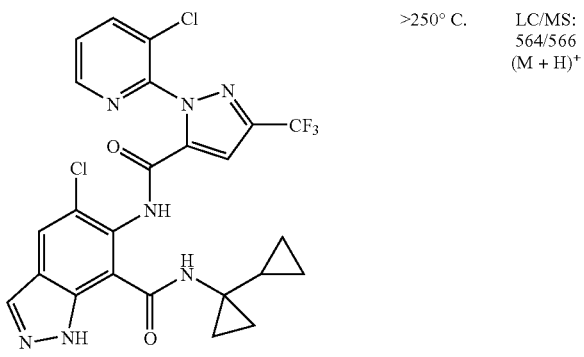 example 12 | >250° C. | LC/MS: 564/566 (M + H)+ |

TABLE P-continued

Physical data of compounds of formula I:

| Compound No. | Structures | Melting Point | MS/NMR |
|---|---|---|---|
| P.13 | example 13 | 100–105° C. | LC/MS: 586/588 (M + H)+ |
| P.14 | example 14 | — | LC/MS: 602/604 (M + H)+; 624/626 (M + Na)+ |
| P.15 | example 15 | 173–176° C. | LC/MS: 640/642 (M + Na)+ |
| P.16 | example 16 | 189–190° C. | LC/MS: 570/572 (M + H)+ |

TABLE P-continued

Physical data of compounds of formula I:

| Compound No. | Structures | Melting Point | MS/NMR |
|---|---|---|---|
| P.17 | example 17 | >255° C. | LC/MS: 564/566 (M + Na)+ |
| P.18 | example 18 | 212-214° C. | LC/MS: 608/610 (M + H)+ |
| P.19 | example 19 | 144-150° C. | LC/MS: 582/584 (M + H)+ |
| P.20 | example 20 | >240° C. | LC/MS: 531/533 (M + H)+ |

TABLE P-continued
Physical data of compounds of formula I:
| Compound No. | Structures | Melting Point | MS/NMR |
|---|---|---|---|
| P.21 | 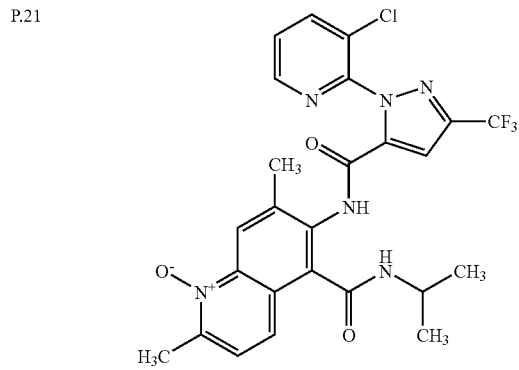 example 21 | >230° C. | LC/MS: 547/549 (M + H)+ |
| P.22 | 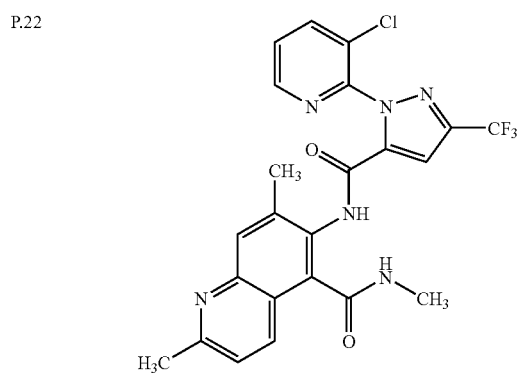 example 22 | >134° C. | — |
| P.23 | 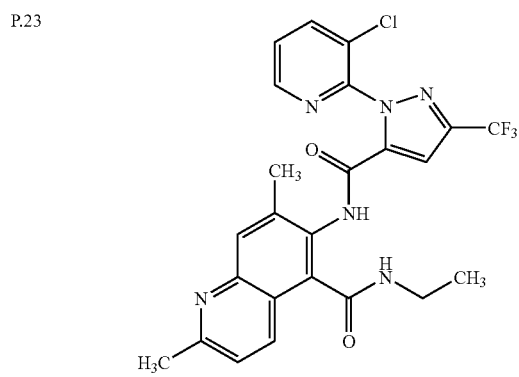 example 23 | >230° C. | LC/MS: 517/519 (M + H)+ |

TABLE P-continued
Physical data of compounds of formula I:
| Compound No. | Structures | Melting Point | MS/NMR |
|---|---|---|---|
| P.24 | 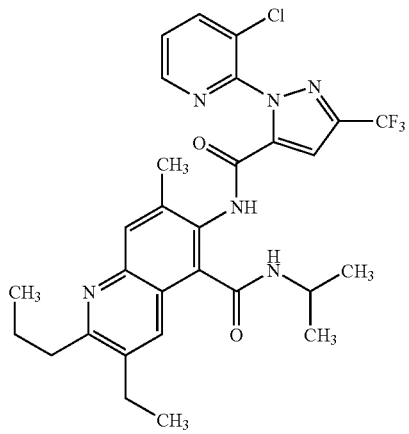 example 24 | 213-220° C. | LC/MS: 587/589 (M + H)+ |
| P.25 | 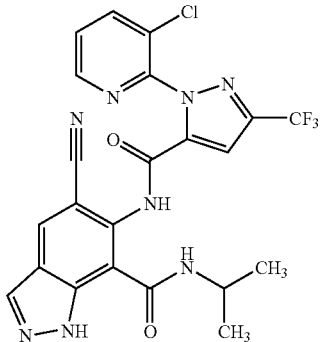 example 25 | — | LC/MS: 519/520 (M + H)+ |
| P.26 | 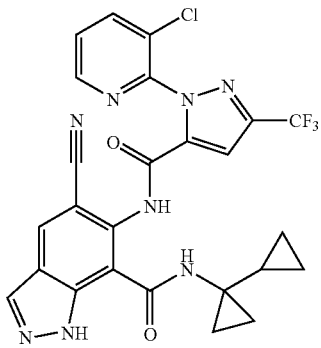 example 26 | — | LC/MS: 555/557 (M + H)+ |

TABLE P-continued
Physical data of compounds of formula I:
| Compound No. | Structures | Melting Point | MS/NMR |
|---|---|---|---|
| P.27 | 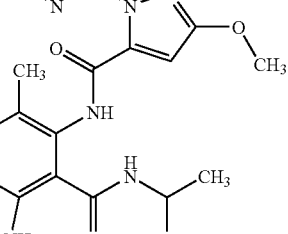 example 27 | 148-151° C. | LC/MS: 468/470 (M + H)+ |
| P.28 | 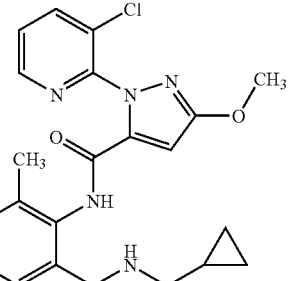 example 28 | 150-154° C. | LC/MS: 506/508 (M + H)+ |
| P.29 | 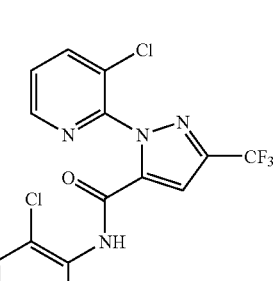 | >255° C. | LC/MS: 498/500 (M + H)+ |
| P.30 | 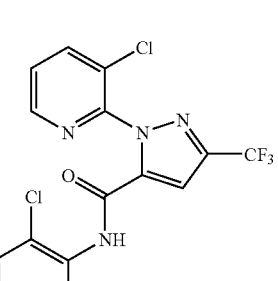 | 243-244° C. | LC/MS: 512/514 (M + H)+ |

TABLE P-continued

Physical data of compounds of formula I:

| Compound No. | Structures | Melting Point | MS/NMR |
|---|---|---|---|
| P.31 | 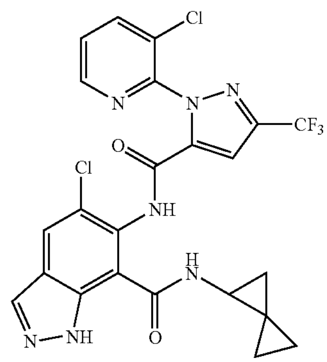 [SMILES: O=C(NC1CC12CC2)c1c(NC(=O)c2cc(C(F)(F)F)nn2-c2ncccc2Cl)c(Cl)cc2cn[nH]c12] | 148-150° C. | LC/MS: 550/552 (M + H)+ |
| P.32 | 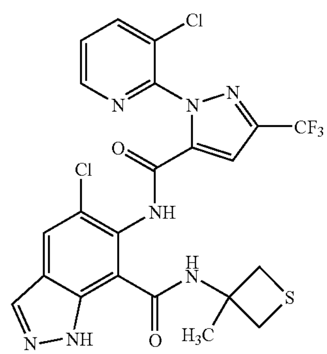 [SMILES: CC1(NC(=O)c2c(NC(=O)c3cc(C(F)(F)F)nn3-c3ncccc3Cl)c(Cl)cc3cn[nH]c23)CSC1] | 159-160° C. decomposition | LC/MS: 570/572 (M + H)+ |
| P.33 | 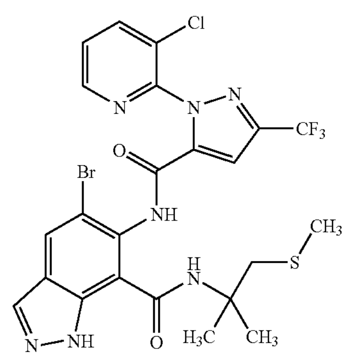 [SMILES: CSCC(C)(C)NC(=O)c1c(NC(=O)c2cc(C(F)(F)F)nn2-c2ncccc2Cl)c(Br)cc2cn[nH]c12] | 135-140° C. decomposition | LC/MS: 632/634 (M + H)+ |
| P.34 | 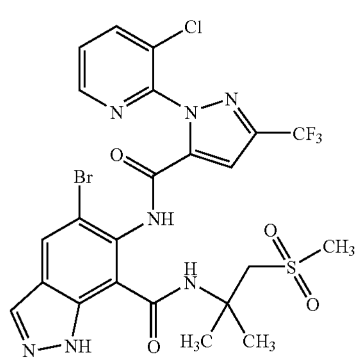 [SMILES: CC(C)(CS(C)(=O)=O)NC(=O)c1c(NC(=O)c2cc(C(F)(F)F)nn2-c2ncccc2Cl)c(Br)cc2cn[nH]c12] | 243-244° C. | LC/MS: 664/666 (M + H)+ |

TABLE P-continued

Physical data of compounds of formula I:

| Compound No. | Structures | Melting Point | MS/NMR |
|---|---|---|---|
| P.35 | 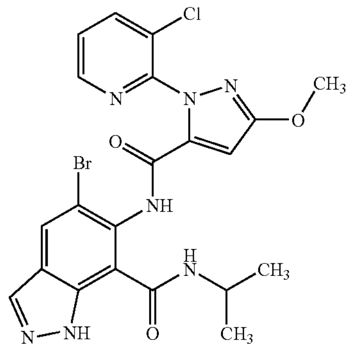 | 141-144° C. | LC/MS: 554/558 (M + Na)+ |
| P.36 | 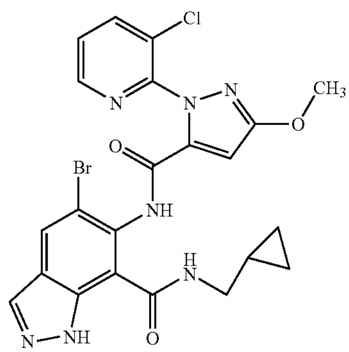 | 144-145° C. decomposition | LC/MS: 568/570 (M + Na)+ |
| P.37 | 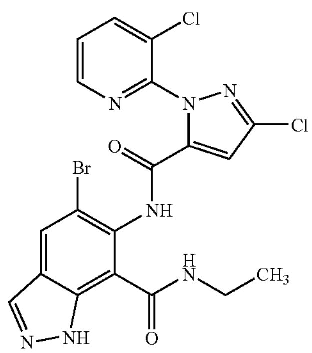 [SMILES: CCNC(=O)c1c(NC(=O)c2cc(Cl)nn2-c2ncccc2Cl)c(Br)cc2cn[nH]c12] | 237-238° C. | LC/MS: 524/526 (M + H)+ |
| P.38 | 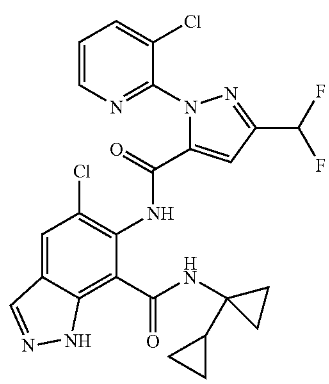 [SMILES: O=C(NC1(C2CC2)CC1)c1c(NC(=O)c2cc(C(F)F)nn2-c2ncccc2Cl)c(Cl)cc2cn[nH]c12] | — | LC/MS: 547/549 (M + H)+ |

TABLE P-continued

Physical data of compounds of formula I:

| Compound No. | Structures | Melting Point | MS/NMR |
|---|---|---|---|
| P.39 | 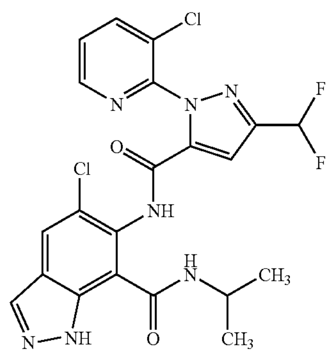 [SMILES: CC(C)NC(=O)c1c(NC(=O)c2cc(C(F)F)nn2-c2ncccc2Cl)c(Cl)cc2cn[nH]c12] | — | LC/MS: 509/511 (M + H)+ |
| P.40 | 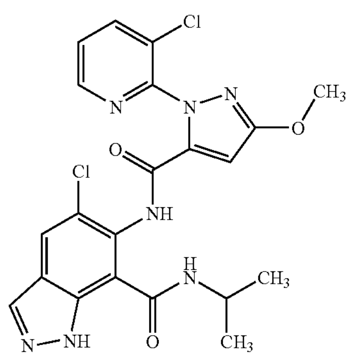 [SMILES: COc1cc(C(=O)Nc2c(Cl)cc3cn[nH]c3c2C(=O)NC(C)C)n(-c2ncccc2Cl)n1] | 186-187° C. | LC/MS: 510/512 (M + Na)+ |
| P.41 | 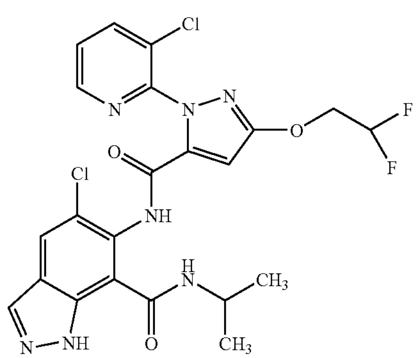 | 237-238° C. | LC/MS: 578/580 (M + Na)+ |
| P.42 | 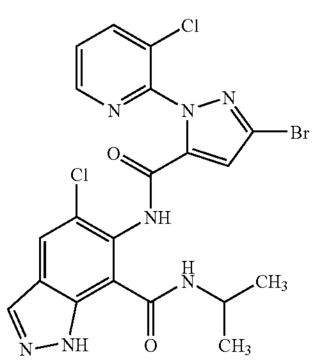 | 217-218° C. | LC/MS: 560/562 (M + Na)+ |

TABLE P-continued
Physical data of compounds of formula I:
| Compound No. | Structures | Melting Point | MS/NMR |
|---|---|---|---|
| P.43 | 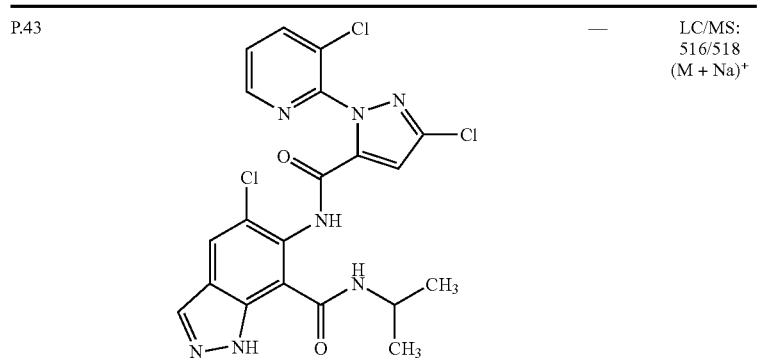 example 36 | — | LC/MS: 516/518 (M + Na)+ |
| P.44 | 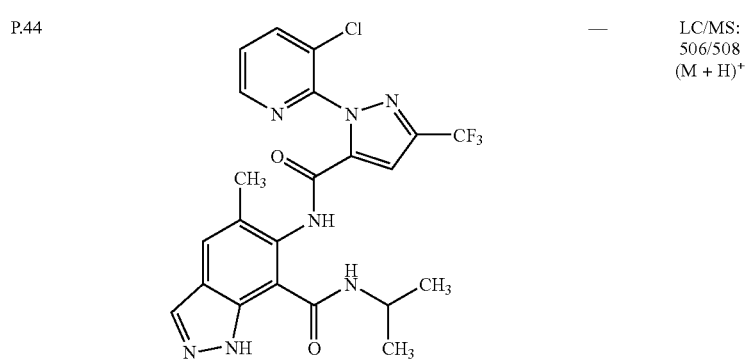 | — | LC/MS: 506/508 (M + H)+ |
| P.45 | 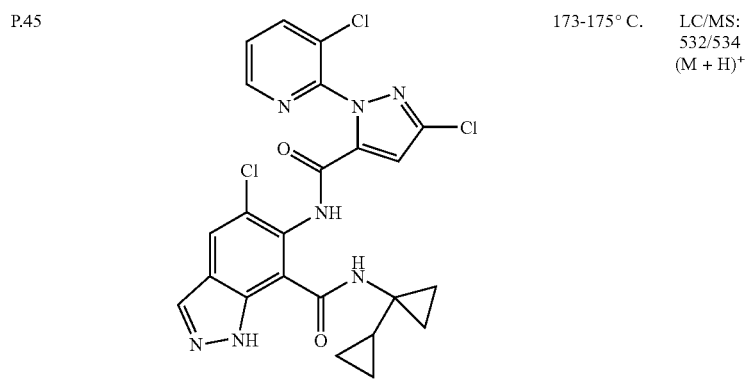 example 37 | 173-175° C. | LC/MS: 532/534 (M + H)+ |
| P.46 | 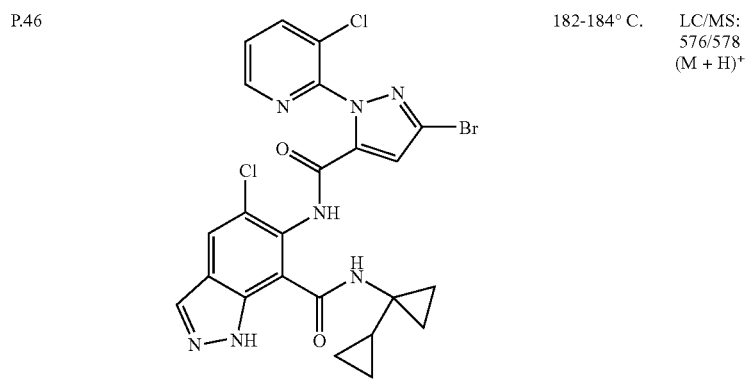 | 182-184° C. | LC/MS: 576/578 (M + H)+ |

TABLE P-continued

Physical data of compounds of formula I:

| Compound No. | Structures | Melting Point | MS/NMR |
|---|---|---|---|
| P.47 | 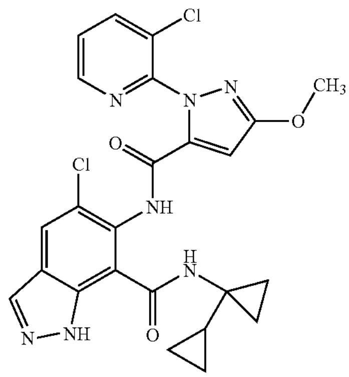 [SMILES: COc1cc(C(=O)Nc2c(Cl)cc3cn[nH]c3c2C(=O)NC2(C3CC3)CC2)n(-c2ncccc2Cl)n1] | 155-157° C. | LC/MS: 526/528 (M + H)+ |
| P.48 | 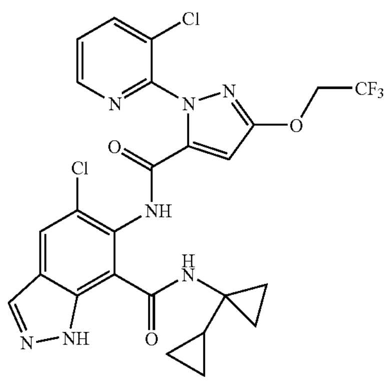 [SMILES: O=C(NC1(C2CC2)CC1)c1c(NC(=O)c2cc(OCC(F)(F)F)nn2-c2ncccc2Cl)c(Cl)cc2cn[nH]c12] | 240-241° C. | LC/MS: 594/596 (M + H)+ |
| P.49 | 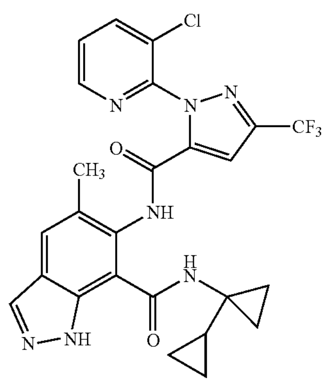 [SMILES: Cc1cc2cn[nH]c2c(C(=O)NC2(C3CC3)CC2)c1NC(=O)c1cc(C(F)(F)F)nn1-c1ncccc1Cl] | 159-162° C. | LC/MS: 544/546 (M + H)+ |
| P.50 | 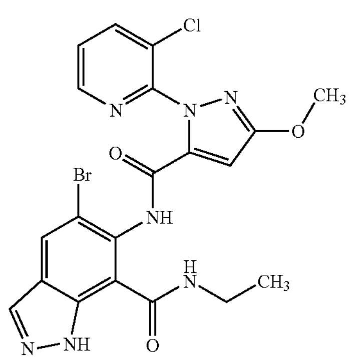 [SMILES: CCNC(=O)c1c(NC(=O)c2cc(OC)nn2-c2ncccc2Cl)c(Br)cc2cn[nH]c12] | 149-152° C. | LC/MS: 520/522 (M + H)+ |

TABLE P-continued
Physical data of compounds of formula I:
| Compound No. | Structures | Melting Point | MS/NMR |
|---|---|---|---|
| P.51 | 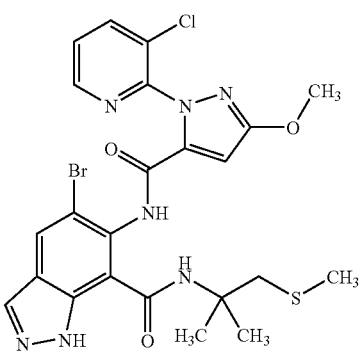 | 151-154° C. | LC/MS: 594/596 (M + H)+ |
| P.52 | 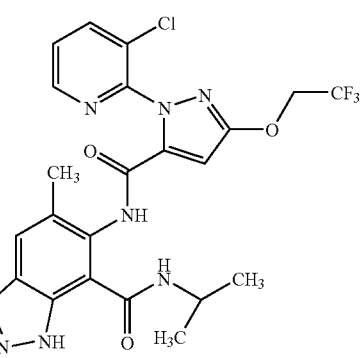 example 29 | 247-250° C. | LC/MS: 536/538 (M + H)+ |
| P.53 | 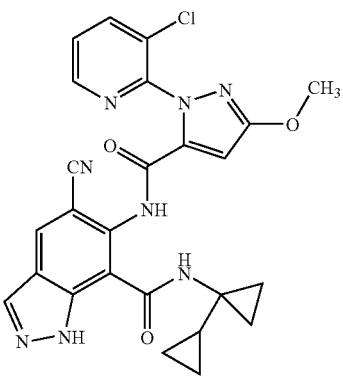 [SMILES: COc1cc(C(=O)Nc2c(C#N)cc3cn[nH]c3c2C(=O)NC2(C3CC3)CC2)n(-c2ncccc2Cl)n1] | 154-156° C. | LC/MS: 517/519 (M + H)+ |
| P.54 | 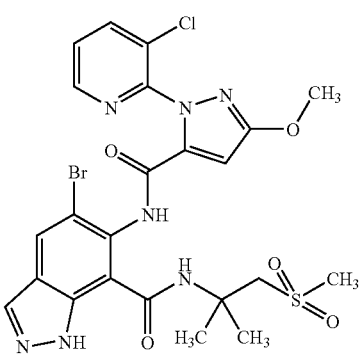 [SMILES: COc1cc(C(=O)Nc2c(Br)cc3cn[nH]c3c2C(=O)NC(C)(C)CS(C)(=O)=O)n(-c2ncccc2Cl)n1] | 275-277° C. | LC/MS: 626/628 (M + H)+ |

TABLE P-continued

Physical data of compounds of formula I:

| Compound No. | Structures | Melting Point | MS/NMR |
|---|---|---|---|
| P.55 | 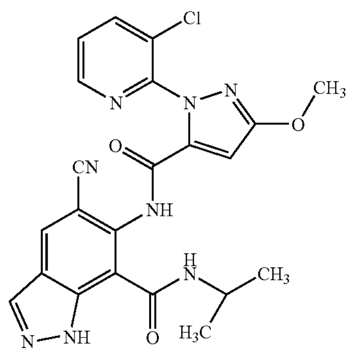 [SMILES: COc1cc(C(=O)Nc2c(C#N)cc3cn[nH]c3c2C(=O)NC(C)C)n(-c2ncccc2Cl)n1] | 224-227° C. | LC/MS: 479/481 (M + H)+ |
| P.56 | 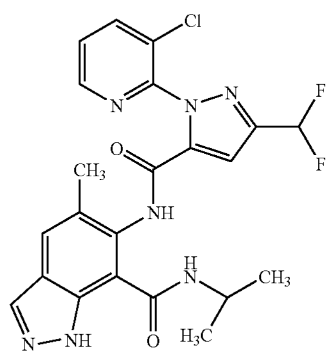 [SMILES: Cc1cc2cn[nH]c2c(C(=O)NC(C)C)c1NC(=O)c1cc(C(F)F)nn1-c1ncccc1Cl] | 250-253° C. | LC/MS: 488/490 (M + H)+ |
| P.57 | 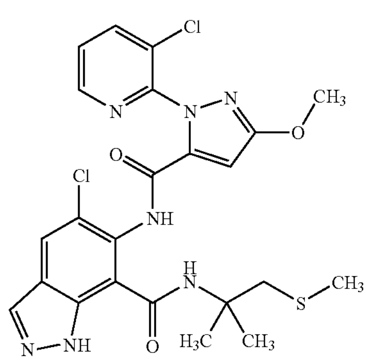 [SMILES: COc1cc(C(=O)Nc2c(Cl)cc3cn[nH]c3c2C(=O)NC(C)(C)CSC)n(-c2ncccc2Cl)n1] | 159-161° C. | LC/MS: 548/550 (M + H)+ |
| P.58 | 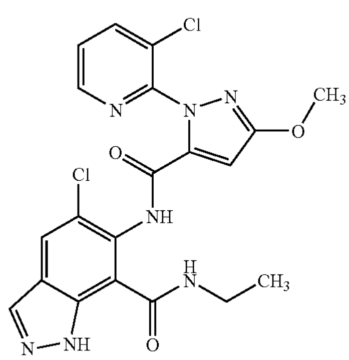 [SMILES: CCNC(=O)c1c(NC(=O)c2cc(OC)nn2-c2ncccc2Cl)c(Cl)cc2cn[nH]c12] | 215-216° C. | LC/MS: 474/476 (M + H)+ |

TABLE P-continued

Physical data of compounds of formula I:

| Compound No. | Structures | Melting Point | MS/NMR |
|---|---|---|---|
| P.59 | example 38 | 162-165° C. | LC/MS: 532/534 (M + H)+ |
| P.60 | 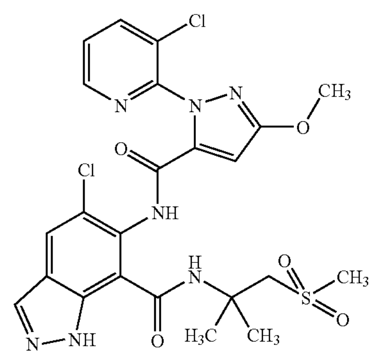 | >250° C. | LC/MS: 580/582 (M + H)+ |
| P.61 | 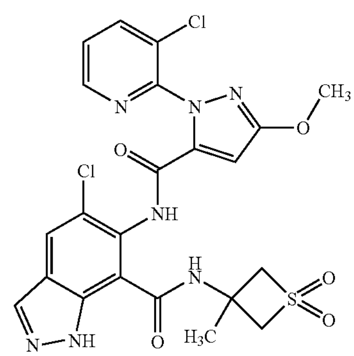 [SMILES: COc1cc(C(=O)Nc2c(Cl)cc3cn[nH]c3c2C(=O)NC2(C)CS(=O)(=O)C2)n(-c2ncccc2Cl)n1] | 167-170° C. | LC/MS: 654/566 (M + H)+ |
| P.62 | example 33 | 224-227° C. | LC/MS: 526/528 (M + H)+ |

TABLE P-continued
Physical data of compounds of formula I:
| Compound No. | Structures | Melting Point | MS/NMR |
|---|---|---|---|
| P.63 | example 39 | 217-218° C. | LC/MS: 568/570 (M + H)+ |
| P.64 | example 40 | 190-194° C. | LC/MS: 606/608 (M + H)+ |
| P.65 | example 31 | 163-166° C. | LC/MS: 518/520 (M + H)+ |
| P.66 | example 34 | 226-229° C. | LC/MS: 516/518 (M + H)+ |
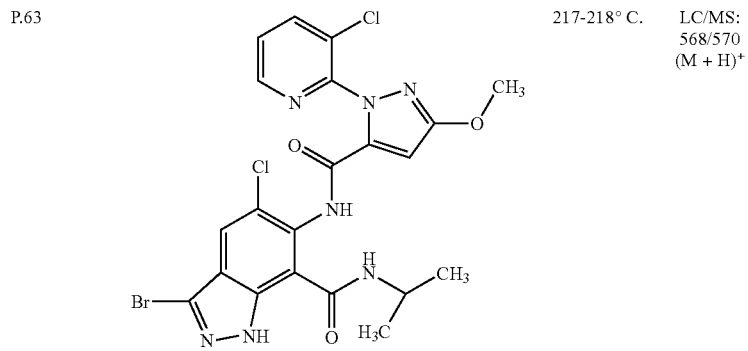

TABLE P-continued

Physical data of compounds of formula I:

| Compound No. | Structures | Melting Point | MS/NMR |
|---|---|---|---|
| P.67 | (3-chloropyridin-2-yl)-pyrazole-CF₃ carboxamide linked to 3-bromo-5-chloro-1H-indazole-7-carboxamide N-isopropyl | 248-250° C. | LC/MS: 606/608 (M + H)⁺ |
| P.68 | (3-chloropyridin-2-yl)-pyrazole-CF₃ carboxamide linked to 3-bromo-5-chloro-1H-indazole-7-carboxamide N-(1-cyclopropylcyclopropyl) | 228-229° C. | LC/MS: 644/646 (M + H)⁺ |
| P.69 | (3-chloropyridin-2-yl)-pyrazole-CF₃ carboxamide linked to 5-chloro-3-methyl-1H-indazole-7-carboxamide N-isopropyl (example 41) | 235-236° C. | LC/MS: 540/542 (M + H)⁺ |
| P.70 | (3-chloropyridin-2-yl)-pyrazole-OCH₂CF₃ carboxamide linked to 5-methyl-1H-indazole-7-carboxamide N-(1-cyclopropylcyclopropyl) (example 30) | 240-242° C. | LC/MS: 574/576 (M + H)⁺ |

TABLE P-continued

Physical data of compounds of formula I:

| Compound No. | Structures | Melting Point | MS/NMR |
|---|---|---|---|
| P.71 | example 32 | 170-173° C. | LC/MS: 556/558 (M + H)+ |
| P.72 | 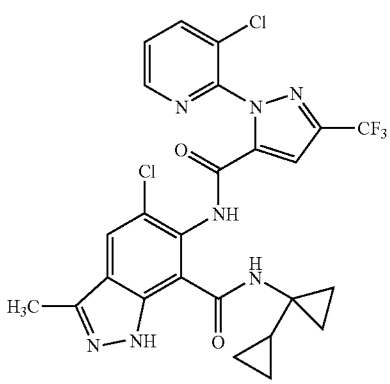 [SMILES: Cc1n[nH]c2c(C(=O)NC3(C4CC4)CC3)c(NC(=O)c3cc(C(F)(F)F)nn3-c3ncccc3Cl)c(Cl)cc12] | 228-229° C. | LC/MS: 578/580 (M + H)+ |
| P.73 | 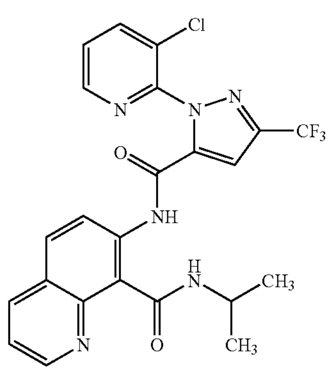 [SMILES: CC(C)NC(=O)c1c(NC(=O)c2cc(C(F)(F)F)nn2-c2ncccc2Cl)ccc2cccnc12] | 225-226° C. | LC/MS: 503/505 (M + H)+ |
| P.74 | 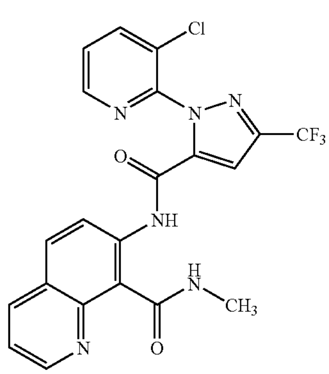 [SMILES: CNC(=O)c1c(NC(=O)c2cc(C(F)(F)F)nn2-c2ncccc2Cl)ccc2cccnc12] | 219-220° C. | LC/MS: 475/477 (M + H)+ |

TABLE P-continued

Physical data of compounds of formula I:

| Compound No. | Structures | Melting Point | MS/NMR |
|---|---|---|---|
| P.75 | 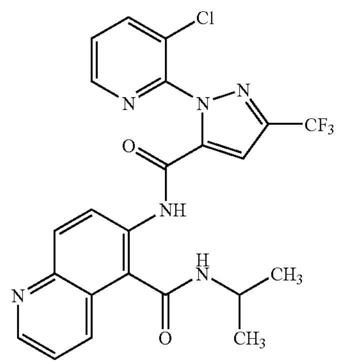 [SMILES: CC(C)NC(=O)c1c(NC(=O)c2cc(C(F)(F)F)nn2-c2ncccc2Cl)ccc2ncccc12] | 182-183° C. | LC/MS: 503/505 (M + H)⁺ |
| P.76 | 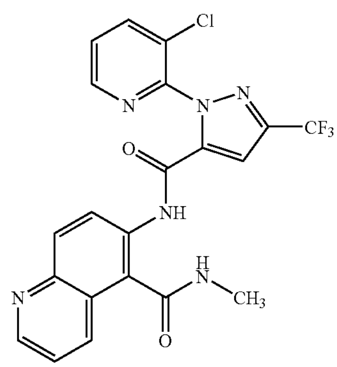 [SMILES: CNC(=O)c1c(NC(=O)c2cc(C(F)(F)F)nn2-c2ncccc2Cl)ccc2ncccc12] | 210-211° C. | LC/MS: 475/477 (M + H)⁺ |
| P.77 | 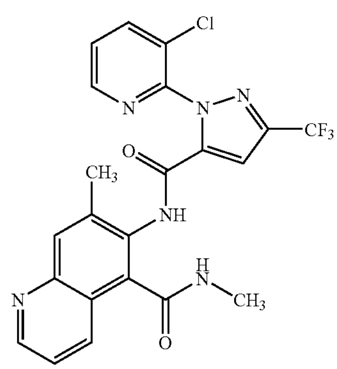 [SMILES: CNC(=O)c1c(NC(=O)c2cc(C(F)(F)F)nn2-c2ncccc2Cl)c(C)cc2ncccc12] | m.p.: 150-152° C. decomposition | LC/MS: 489/491 (M + H)⁺ |
| P.78 | 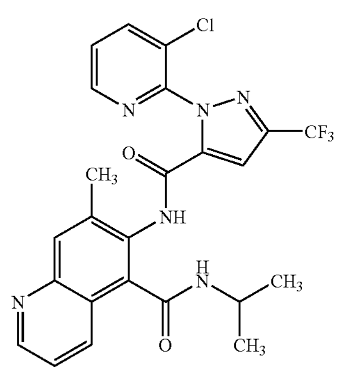 [SMILES: Cc1cc2ncccc2c(C(=O)NC(C)C)c1NC(=O)c1cc(C(F)(F)F)nn1-c1ncccc1Cl] | m.p.: 162-168° C. decomposition | LC/MS: 517/519 (M + H)⁺ |

TABLE P-continued
Physical data of compounds of formula I:
| Compound No. | Structures | Melting Point | MS/NMR |
|---|---|---|---|
| P.79 | 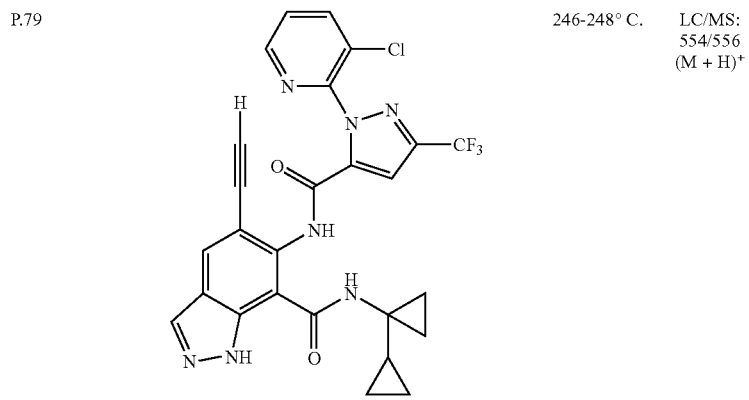 | 246-248° C. | LC/MS: 554/556 (M + H)+ |
| P.80 | 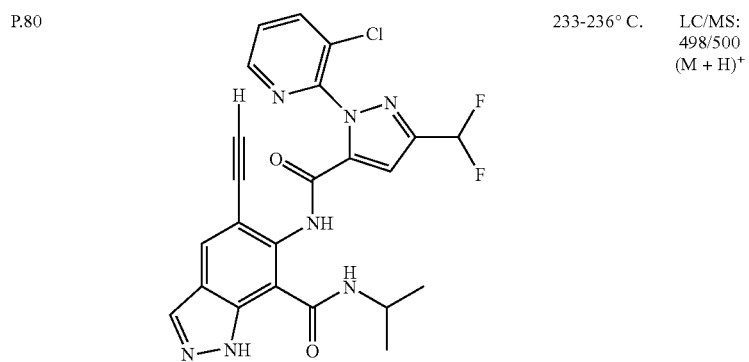 | 233-236° C. | LC/MS: 498/500 (M + H)+ |
| P.81 | 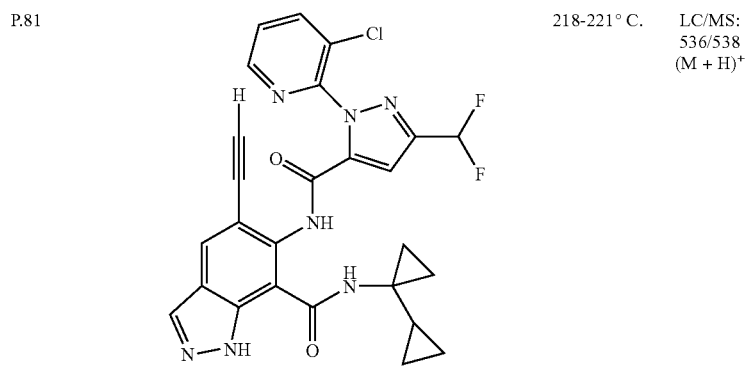 | 218-221° C. | LC/MS: 536/538 (M + H)+ |

The compounds according to the following tables can be prepared analogously. The examples which follow are intended to illustrate the invention and show preferred compounds of formula I.

TABLE A

Compounds of formula Ib:

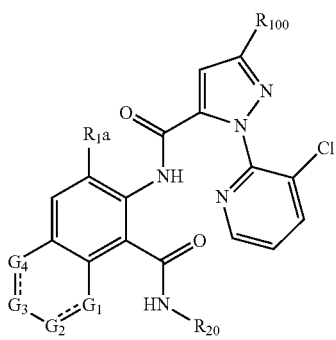

(Ib)

| Line | $R_1a$ | $R_{100}$ | $R_{20}$ |
|---|---|---|---|
| A.1.1 | $CH_3$ | $CF_3$ | H |
| A.1.2 | $CH_3$ | $CF_3$ | $CH_3$ |
| A.1.3 | $CH_3$ | $CF_3$ | $CH_2CH_3$ |
| A.1.4 | $CH_3$ | $CF_3$ | $CH(CH_3)CH_3$ |
| A.1.5 | $CH_3$ | $CF_3$ | $C(CH_3)(CH_3)CH_3$ |
| A.1.6 | $CH_3$ | $CF_3$ | 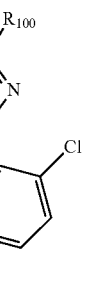 |
| A.1.7 | $CH_3$ | $CF_3$ | |
| A.1.8 | $CH_3$ | $CF_3$ | |
| A.1.9 | $CH_3$ | $CF_3$ | |
| A.1.10 | $CH_3$ | $CF_3$ | $CH(CH_3)_2CH_2SCH_3$ |
| A.1.11 | $CH_3$ | $CF_3$ | $CH(CH_3)_2S(O)CH_3$ |
| A.1.12 | $CH_3$ | $CF_3$ | $CH(CH_3)_2S(O)_2CH_3$ |
| A.1.13 | $CH_3$ | $OCH_2CF_3$ | H |
| A.1.14 | $CH_3$ | $OCH_2CF_3$ | $CH_3$ |
| A.1.15 | $CH_3$ | $OCH_2CF_3$ | $CH_2CH_3$ |
| A.1.16 | $CH_3$ | $OCH_2CF_3$ | $CH(CH_3)CH_3$ |
| A.1.17 | $CH_3$ | $OCH_2CF_3$ | $C(CH_3)(CH_3)CH_3$ |
| A.1.18 | $CH_3$ | $OCH_2CF_3$ | |
| A.1.19 | $CH_3$ | $OCH_2CF_3$ | |

TABLE A-continued

Compounds of formula Ib:

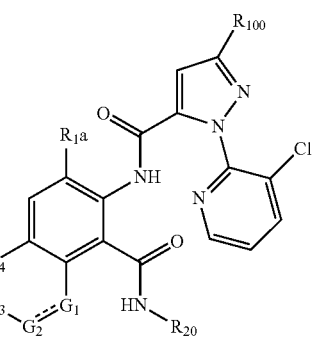

(Ib)

| Line | $R_1a$ | $R_{100}$ | $R_{20}$ |
|---|---|---|---|
| A.1.20 | $CH_3$ | $OCH_2CF_3$ | |
| A.1.21 | $CH_3$ | $OCH_2CF_3$ | |
| A.1.22 | $CH_3$ | $OCH_2CF_3$ | $CH(CH_3)_2CH_2SCH_3$ |
| A.1.23 | $CH_3$ | $OCH_2CF_3$ | $CH(CH_3)_2S(O)CH_3$ |
| A.1.24 | $CH_3$ | $OCH_2CF_3$ | $CH(CH_3)_2S(O)_2CH_3$ |
| A.1.25 | $CH_3$ | Br | H |
| A.1.26 | $CH_3$ | Br | $CH_3$ |
| A.1.27 | $CH_3$ | Br | $CH_2CH_3$ |
| A.1.28 | $CH_3$ | Br | $CH(CH_3)CH_3$ |
| A.1.29 | $CH_3$ | Br | $C(CH_3)(CH_3)CH_3$ |
| A.1.30 | $CH_3$ | Br | 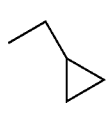 |
| A.1.31 | $CH_3$ | Br | |
| A.1.32 | $CH_3$ | Br | 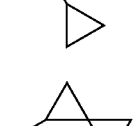 |
| A.1.33 | $CH_3$ | Br | 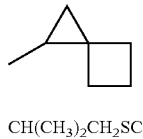 |
| A.1.34 | $CH_3$ | Br | $CH(CH_3)_2CH_2SCH_3$ |
| A.1.35 | $CH_3$ | Br | $CH(CH_3)_2S(O)CH_3$ |
| A.1.36 | $CH_3$ | Br | $CH(CH_3)_2S(O)_2CH_3$ |
| A.1.37 | $CH_3$ | Cl | H |
| A.1.38 | $CH_3$ | Cl | $CH_3$ |
| A.1.39 | $CH_3$ | Cl | $CH_2CH_3$ |
| A.1.40 | $CH_3$ | Cl | $CH(CH_3)CH_3$ |
| A.1.41 | $CH_3$ | Cl | $C(CH_3)(CH_3)CH_3$ |
| A.1.42 | $CH_3$ | Cl | 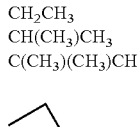 |

TABLE A-continued

Compounds of formula Ib:

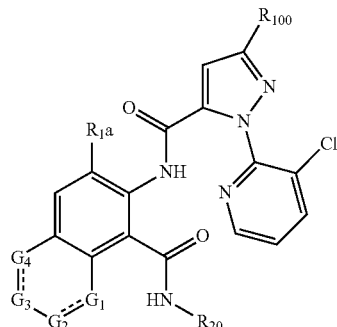
(Ib)

| Line | R₁a | R₁₀₀ | R₂₀ |
|---|---|---|---|
| A.1.43 | CH₃ | Cl | 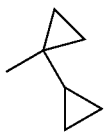 |
| A.1.44 | CH₃ | Cl | 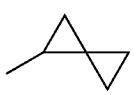 |
| A.1.45 | CH₃ | Cl | 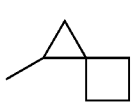 |
| A.1.46 | CH₃ | Cl | CH(CH₃)₂CH₂SCH₃ |
| A.1.47 | CH₃ | Cl | CH(CH₃)₂CH₂S(O)CH₃ |
| A.1.48 | CH₃ | Cl | CH(CH₃)₂CH₂S(O)₂CH₃ |
| A.1.49 | CH₃ | CF₂H | H |
| A.1.50 | CH₃ | CF₂H | CH₃ |
| A.1.51 | CH₃ | CF₂H | CH₂CH₃ |
| A.1.52 | CH₃ | CF₂H | CH(CH₃)CH₃ |
| A.1.53 | CH₃ | CF₂H | C(CH₃)(CH₃)CH₃ |
| A.1.54 | CH₃ | CF₂H | 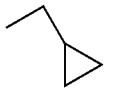 |
| A.1.55 | CH₃ | CF₂H | 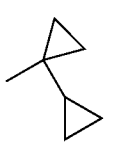 |
| A.1.56 | CH₃ | CF₂H | 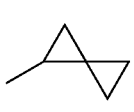 |
| A.1.57 | CH₃ | CF₂H | 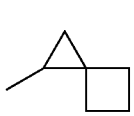 |
| A.1.58 | CH₃ | CF₂H | CH(CH₃)₂CH₂SCH₃ |
| A.1.59 | CH₃ | CF₂H | CH(CH₃)₂CH₂S(O)CH₃ |
| A.1.60 | CH₃ | CF₂H | CH(CH₃)₂CH₂S(O)₂CH₃ |
| A.1.61 | CH₃ | OCF₃ | H |
| A.1.62 | CH₃ | OCF₃ | CH₃ |
| A.1.63 | CH₃ | OCF₃ | CH₂CH₃ |
| A.1.64 | CH₃ | OCF₃ | CH(CH₃)CH₃ |
| A.1.65 | CH₃ | OCF₃ | C(CH₃)(CH₃)CH₃ |

TABLE A-continued

Compounds of formula Ib:

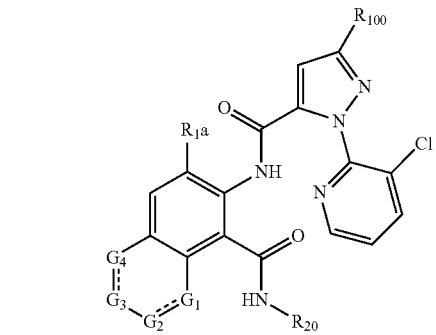
(Ib)

| Line | R₁a | R₁₀₀ | R₂₀ |
|---|---|---|---|
| A.1.66 | CH₃ | OCF₃ |  |
| A.1.67 | CH₃ | OCF₃ |  |
| A.1.68 | CH₃ | OCF₃ | 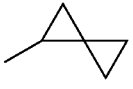 |
| A.1.69 | CH₃ | OCF₃ |  |
| A.1.70 | CH₃ | OCF₃ | CH(CH₃)₂CH₂SCH₃ |
| A.1.71 | CH₃ | OCF₃ | CH(CH₃)₂CH₂S(O)CH₃ |
| A.1.72 | CH₃ | OCF₃ | CH(CH₃)₂CH₂S(O)₂CH₃ |
| A.1.73 | Cl | CF₃ | H |
| A.1.74 | Cl | CF₃ | CH₃ |
| A.1.75 | Cl | CF₃ | CH₂CH₃ |
| A.1.76 | Cl | CF₃ | CH(CH₃)CH₃ |
| A.1.77 | Cl | CF₃ | C(CH₃)(CH₃)CH₃ |
| A.1.78 | Cl | CF₃ | 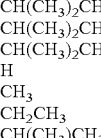 |
| A.1.79 | Cl | CF₃ | 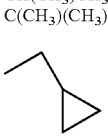 |
| A.1.80 | Cl | CF₃ | 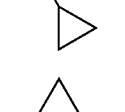 |
| A.1.81 | Cl | CF₃ |  |
| A.1.82 | Cl | CF₃ | CH(CH₃)₂CH₂SCH₃ |
| A.1.83 | Cl | CF₃ | CH(CH₃)₂CH₂S(O)CH₃ |
| A.1.84 | Cl | CF₃ | CH(CH₃)₂CH₂S(O)₂CH₃ |
| A.1.85 | Cl | OCH₂CF₃ | H |
| A.1.86 | Cl | OCH₂CF₃ | CH₃ |
| A.1.87 | Cl | OCH₂CF₃ | CH₂CH₃ |

TABLE A-continued

Compounds of formula Ib:

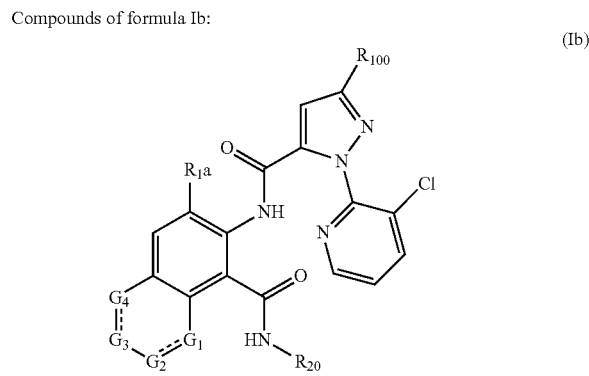
(Ib)

| Line | $R_1a$ | $R_{100}$ | $R_{20}$ |
|---|---|---|---|
| A.1.88 | Cl | $OCH_2CF_3$ | $CH(CH_3)CH_3$ |
| A.1.89 | Cl | $OCH_2CF_3$ | $C(CH_3)(CH_3)CH_3$ |
| A.1.90 | Cl | $OCH_2CF_3$ | |
| A.1.91 | Cl | $OCH_2CF_3$ | |
| A.1.92 | Cl | $OCH_2CF_3$ | |
| A.1.93 | Cl | $OCH_2CF_3$ | |
| A.1.94 | Cl | $OCH_2CF_3$ | $CH(CH_3)_2CH_2SCH_3$ |
| A.1.95 | Cl | $OCH_2CF_3$ | $CH(CH_3)_2CH_2S(O)CH_3$ |
| A.1.96 | Cl | $OCH_2CF_3$ | $CH(CH_3)_2CH_2S(O)_2CH_3$ |
| A.1.97 | Cl | Br | H |
| A.1.98 | Cl | Br | $CH_3$ |
| A.1.99 | Cl | Br | $CH_2CH_3$ |
| A.1.100 | Cl | Br | $CH(CH_3)CH_3$ |
| A.1.101 | Cl | Br | $C(CH_3)(CH_3)CH_3$ |
| A.1.102 | Cl | Br | |
| A.1.103 | Cl | Br | |
| A.1.104 | Cl | Br | |
| A.1.105 | Cl | Br | |
| A.1.106 | Cl | Br | $CH(CH_3)_2CH_2SCH_3$ |
| A.1.107 | Cl | Br | $CH(CH_3)_2CH_2S(O)CH_3$ |

TABLE A-continued

Compounds of formula Ib:

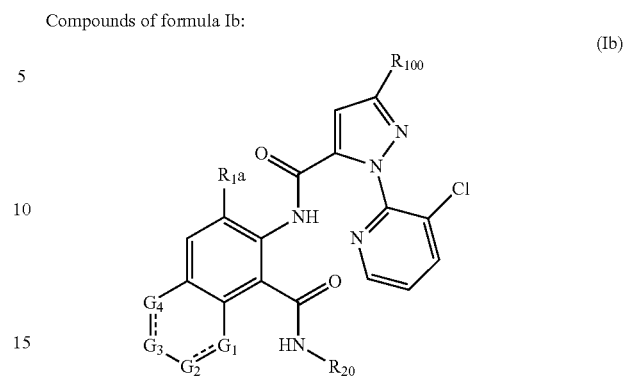
(Ib)

| Line | $R_1a$ | $R_{100}$ | $R_{20}$ |
|---|---|---|---|
| A.1.108 | Cl | Br | $CH(CH_3)_2CH_2S(O)_2CH_3$ |
| A.1.109 | Cl | Cl | H |
| A.1.110 | Cl | Cl | $CH_3$ |
| A.1.111 | Cl | Cl | $CH_2CH_3$ |
| A.1.112 | Cl | Cl | $CH(CH_3)CH_3$ |
| A.1.113 | Cl | Cl | $C(CH_3)(CH_3)CH_3$ |
| A.1.114 | Cl | Cl | |
| A.1.115 | Cl | Cl | |
| A.1.116 | Cl | Cl | |
| A.1.117 | Cl | Cl | |
| A.1.118 | Cl | Cl | $CH(CH_3)_2CH_2SCH_3$ |
| A.1.119 | Cl | Cl | $CH(CH_3)_2CH_2S(O)CH_3$ |
| A.1.120 | Cl | Cl | $CH(CH_3)_2CH_2S(O)_2CH_3$ |
| A.1.121 | Cl | $CF_2H$ | H |
| A.1.122 | Cl | $CF_2H$ | $CH_3$ |
| A.1.123 | Cl | $CF_2H$ | $CH_2CH_3$ |
| A.1.124 | Cl | $CF_2H$ | $CH(CH_3)CH_3$ |
| A.1.125 | Cl | $CF_2H$ | $C(CH_3)(CH_3)CH_3$ |
| A.1.126 | Cl | $CF_2H$ | |
| A.1.127 | Cl | $CF_2H$ | |
| A.1.128 | Cl | $CF_2H$ | |

TABLE A-continued

Compounds of formula Ib:

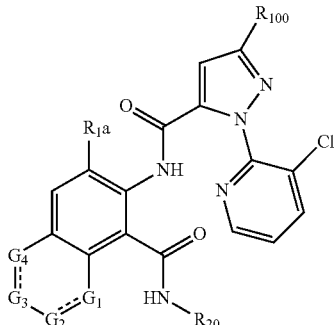

(Ib)

| Line | R₁a | R₁₀₀ | R₂₀ |
|---|---|---|---|
| A.1.129 | Cl | CF₂H | |
| A.1.130 | Cl | CF₂H | CH(CH₃)₂CH₂SCH₃ |
| A.1.131 | Cl | CF₂H | CH(CH₃)₂CH₂S(O)CH₃ |
| A.1.132 | Cl | CF₂H | CH(CH₃)₂CH₂S(O)₂CH₃ |
| A.1.133 | Cl | OCF₃ | H |
| A.1.134 | Cl | OCF₃ | CH₃ |
| A.1.135 | Cl | OCF₃ | CH₂CH₃ |
| A.1.136 | Cl | OCF₃ | CH(CH₃)CH₃ |
| A.1.137 | Cl | OCF₃ | C(CH₃)(CH₃)CH₃ |
| A.1.138 | Cl | OCF₃ | |
| A.1.139 | Cl | OCF₃ | |
| A.1.140 | Cl | OCF₃ | |
| A.1.141 | Cl | OCF₃ | |
| A.1.142 | Cl | OCF₃ | CH(CH₃)₂CH₂SCH₃ |
| A.1.143 | Cl | OCF₃ | CH(CH₃)₂CH₂S(O)CH₃ |
| A.1.144 | Cl | OCF₃ | CH(CH₃)₂CH₂S(O)₂CH₃ |
| A.1.145 | Br | CF₃ | H |
| A.1.146 | Br | CF₃ | CH₃ |
| A.1.147 | Br | CF₃ | CH₂CH₃ |
| A.1.148 | Br | CF₃ | CH(CH₃)CH₃ |
| A.1.149 | Br | CF₃ | C(CH₃)(CH₃)CH₃ |
| A.1.150 | Br | CF₃ | |
| A.1.151 | Br | CF₃ | |

TABLE A-continued

Compounds of formula Ib:

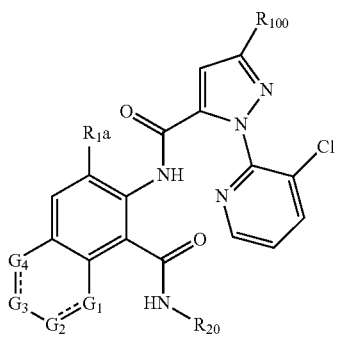

(Ib)

| Line | R₁a | R₁₀₀ | R₂₀ |
|---|---|---|---|
| A.1.152 | Br | CF₃ | |
| A.1.153 | Br | CF₃ | |
| A.1.154 | Br | CF₃ | CH(CH₃)₂CH₂SCH₃ |
| A.1.155 | Br | CF₃ | CH(CH₃)₂CH₂S(O)CH₃ |
| A.1.156 | Br | CF₃ | CH(CH₃)₂CH₂S(O)₂CH₃ |
| A.1.157 | Br | OCH₂CF₃ | H |
| A.1.158 | Br | OCH₂CF₃ | CH₃ |
| A.1.159 | Br | OCH₂CF₃ | CH₂CH₃ |
| A.1.160 | Br | OCH₂CF₃ | CH(CH₃)CH₃ |
| A.1.161 | Br | OCH₂CF₃ | C(CH₃)(CH₃)CH₃ |
| A.1.162 | Br | OCH₂CF₃ | |
| A.1.163 | Br | OCH₂CF₃ | |
| A.1.164 | Br | OCH₂CF₃ | |
| A.1.165 | Br | OCH₂CF₃ | |
| A.1.166 | Br | OCH₂CF₃ | CH(CH₃)₂CH₂SCH₃ |
| A.1.167 | Br | OCH₂CF₃ | CH(CH₃)₂CH₂S(O)CH₃ |
| A.1.168 | Br | OCH₂CF₃ | CH(CH₃)₂CH₂S(O)₂CH₃ |
| A.1.169 | Br | Br | H |
| A.1.170 | Br | Br | CH₃ |
| A.1.171 | Br | Br | CH₂CH₃ |
| A.1.172 | Br | Br | CH(CH₃)CH₃ |
| A.1.173 | Br | Br | C(CH₃)(CH₃)CH₃ |
| A.1.174 | Br | Br | |

TABLE A-continued

Compounds of formula Ib:

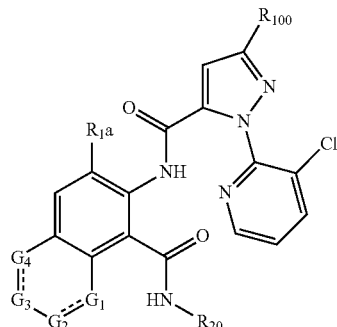

(Ib)

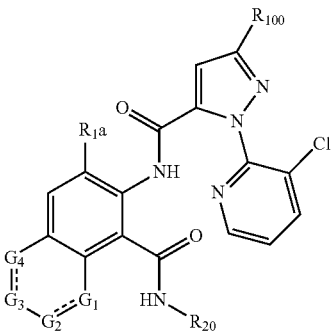

(Ib)

| Line | R₁a | R₁₀₀ | R₂₀ |
|---|---|---|---|
| A.1.175 | Br | Br | 1-methylcyclopropyl-cyclopropyl |
| A.1.176 | Br | Br | methylenebis(cyclopropyl) |
| A.1.177 | Br | Br | cyclopropyl-cyclobutyl |
| A.1.178 | Br | Br | CH(CH₃)₂CH₂SCH₃ |
| A.1.179 | Br | Br | CH(CH₃)₂CH₂S(O)CH₃ |
| A.1.180 | Br | Br | CH(CH₃)₂CH₂S(O)₂CH₃ |
| A.1.181 | Br | Cl | H |
| A.1.182 | Br | Cl | CH₃ |
| A.1.183 | Br | Cl | CH₂CH₃ |
| A.1.184 | Br | Cl | CH(CH₃)CH₃ |
| A.1.185 | Br | Cl | C(CH₃)(CH₃)CH₃ |
| A.1.186 | Br | Cl | cyclopropylmethyl |
| A.1.187 | Br | Cl | 1-methylcyclopropyl-cyclopropyl |
| A.1.188 | Br | Cl | methylenebis(cyclopropyl) |
| A.1.189 | Br | Cl | cyclopropyl-cyclobutyl |
| A.1.190 | Br | Cl | CH(CH₃)₂CH₂SCH₃ |
| A.1.191 | Br | Cl | CH(CH₃)₂CH₂S(O)CH₃ |
| A.1.192 | Br | Cl | CH(CH₃)₂CH₂S(O)₂CH₃ |
| A.1.193 | Br | CF₂H | H |
| A.1.194 | Br | CF₂H | CH₃ |
| A.1.195 | Br | CF₂H | CH₂CH₃ |
| A.1.196 | Br | CF₂H | CH(CH₃)CH₃ |
| A.1.197 | Br | CF₂H | C(CH₃)(CH₃)CH₃ |
| A.1.198 | Br | CF₂H | cyclopropylmethyl |
| A.1.199 | Br | CF₂H | 1-methylcyclopropyl-cyclopropyl |
| A.1.200 | Br | CF₂H | methylenebis(cyclopropyl) |
| A.1.201 | Br | CF₂H | cyclopropyl-cyclobutyl |
| A.1.202 | Br | CF₂H | CH(CH₃)₂CH₂SCH₃ |
| A.1.203 | Br | CF₂H | CH(CH₃)₂CH₂S(O)CH₃ |
| A.1.204 | Br | CF₂H | CH(CH₃)₂CH₂S(O)₂CH₃ |
| A.1.205 | Br | OCF₃ | H |
| A.1.206 | Br | OCF₃ | CH₃ |
| A.1.207 | Br | OCF₃ | CH₂CH₃ |
| A.1.208 | Br | OCF₃ | CH(CH₃)CH₃ |
| A.1.209 | Br | OCF₃ | C(CH₃)(CH₃)CH₃ |
| A.1.210 | Br | OCF₃ | cyclopropylmethyl |
| A.1.211 | Br | OCF₃ | 1-methylcyclopropyl-cyclopropyl |
| A.1.212 | Br | OCF₃ | methylenebis(cyclopropyl) |
| A.1.213 | Br | OCF₃ | cyclopropyl-cyclobutyl |
| A.1.214 | Br | OCF₃ | CH(CH₃)₂CH₂SCH₃ |
| A.1.215 | Br | OCF₃ | CH(CH₃)₂CH₂S(O)CH₃ |
| A.1.216 | Br | OCF₃ | CH(CH₃)₂CH₂S(O)₂CH₃ |
| A.1.217 | CN | CF₃ | H |
| A.1.218 | CN | CF₃ | CH₃ |

TABLE A-continued

Compounds of formula Ib:

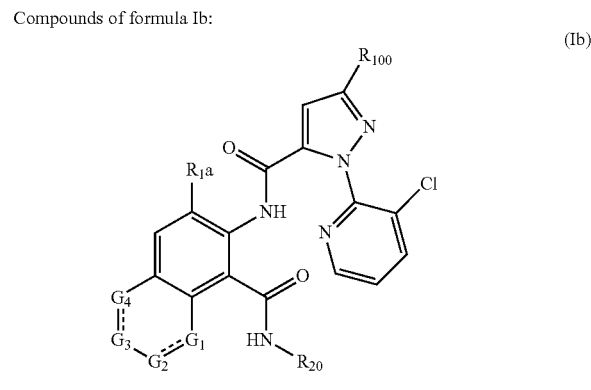
(Ib)

| Line | R₁a | R₁₀₀ | R₂₀ |
|---|---|---|---|
| A.1.219 | CN | CF₃ | CH₂CH₃ |
| A.1.220 | CN | CF₃ | CH(CH₃)CH₃ |
| A.1.221 | CN | CF₃ | C(CH₃)(CH₃)CH₃ |
| A.1.222 | CN | CF₃ | 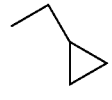 |
| A.1.223 | CN | CF₃ |  |
| A.1.224 | CN | CF₃ |  |
| A.1.225 | CN | CF₃ |  |
| A.1.226 | CN | CF₃ | CH(CH₃)₂CH₂SCH₃ |
| A.1.227 | CN | CF₃ | CH(CH₃)₂CH₂S(O)CH₃ |
| A.1.228 | CN | CF₃ | CH(CH₃)₂CH₂S(O)₂CH₃ |
| A.1.229 | CN | OCH₂CF₃ | H |
| A.1.230 | CN | OCH₂CF₃ | CH₃ |
| A.1.231 | CN | OCH₂CF₃ | CH₂CH₃ |
| A.1.232 | CN | OCH₂CF₃ | CH(CH₃)CH₃ |
| A.1.233 | CN | OCH₂CF₃ | C(CH₃)(CH₃)CH₃ |
| A.1.234 | CN | OCH₂CF₃ | 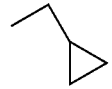 |
| A.1.235 | CN | OCH₂CF₃ |  |
| A.1.236 | CN | OCH₂CF₃ |  |
| A.1.237 | CN | OCH₂CF₃ |  |
| A.1.238 | CN | OCH₂CF₃ | CH(CH₃)₂CH₂SCH₃ |

TABLE A-continued

Compounds of formula Ib:

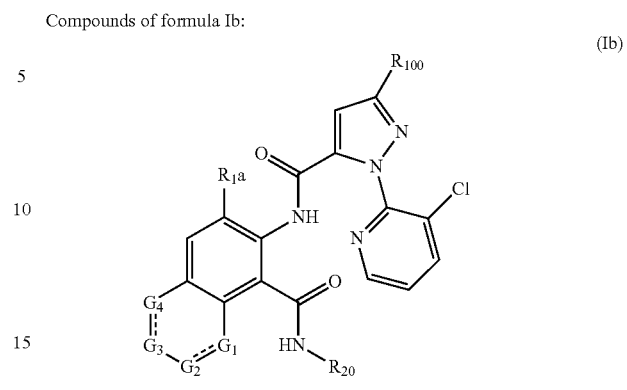
(Ib)

| Line | R₁a | R₁₀₀ | R₂₀ |
|---|---|---|---|
| A.1.239 | CN | OCH₂CF₃ | CH(CH₃)₂CH₂S(O)CH₃ |
| A.1.240 | CN | OCH₂CF₃ | CH(CH₃)₂CH₂S(O)₂CH₃ |
| A.1.241 | CN | Br | H |
| A.1.242 | CN | Br | CH₃ |
| A.1.243 | CN | Br | CH₂CH₃ |
| A.1.244 | CN | Br | CH(CH₃)CH₃ |
| A.1.245 | CN | Br | C(CH₃)(CH₃)CH₃ |
| A.1.246 | CN | Br |  |
| A.1.247 | CN | Br |  |
| A.1.248 | CN | Br | 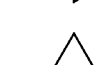 |
| A.1.249 | CN | Br |  |
| A.1.250 | CN | Br | CH(CH₃)₂CH₂SCH₃ |
| A.1.251 | CN | Br | CH(CH₃)₂CH₂S(O)CH₃ |
| A.1.252 | CN | Br | CH(CH₃)₂CH₂S(O)₂CH₃ |
| A.1.253 | CN | Cl | H |
| A.1.254 | CN | Cl | CH₃ |
| A.1.255 | CN | Cl | CH₂CH₃ |
| A.1.256 | CN | Cl | CH(CH₃)CH₃ |
| A.1.257 | CN | Cl | C(CH₃)(CH₃)CH₃ |
| A.1.258 | CN | Cl |  |
| A.1.259 | CN | Cl |  |
| A.1.260 | CN | Cl |  |

TABLE A-continued

Compounds of formula Ib:

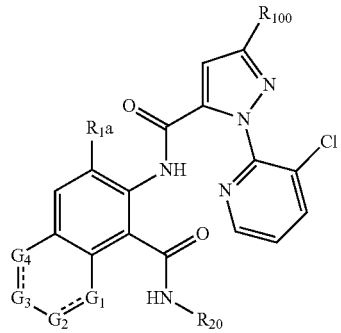

(Ib)

| Line | R₁a | R₁₀₀ | R₂₀ |
|---|---|---|---|
| A.1.261 | CN | Cl |  |
| A.1.262 | CN | Cl | CH(CH₃)₂CH₂SCH₃ |
| A.1.263 | CN | Cl | CH(CH₃)₂CH₂S(O)CH₃ |
| A.1.264 | CN | Cl | CH(CH₃)₂CH₂S(O)₂CH₃ |
| A.1.265 | CN | CF₂H | H |
| A.1.266 | CN | CF₂H | CH₃ |
| A.1.267 | CN | CF₂H | CH₂CH₃ |
| A.1.268 | CN | CF₂H | CH(CH₃)CH₃ |
| A.1.269 | CN | CF₂H | C(CH₃)(CH₃)CH₃ |
| A.1.270 | CN | CF₂H | 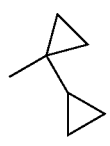 |
| A.1.271 | CN | CF₂H | |
| A.1.272 | CN | CF₂H |  |
| A.1.273 | CN | CF₂H | 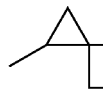 |
| A.1.274 | CN | CF₂H | CH(CH₃)₂CH₂SCH₃ |
| A.1.275 | CN | CF₂H | CH(CH₃)₂CH₂S(O)CH₃ |
| A.1.276 | CN | CF₂H | CH(CH₃)₂CH₂S(O)₂CH₃ |
| A.1.277 | CN | OCF₃ | H |
| A.1.278 | CN | OCF₃ | CH₃ |
| A.1.279 | CN | OCF₃ | CH₂CH₃ |
| A.1.280 | CN | OCF₃ | CH(CH₃)CH₃ |
| A.1.281 | CN | OCF₃ | C(CH₃)(CH₃)CH₃ |
| A.1.282 | CN | OCF₃ | |
| A.1.283 | CN | OCF₃ | 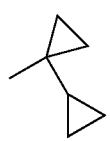 |

TABLE A-continued

Compounds of formula Ib:

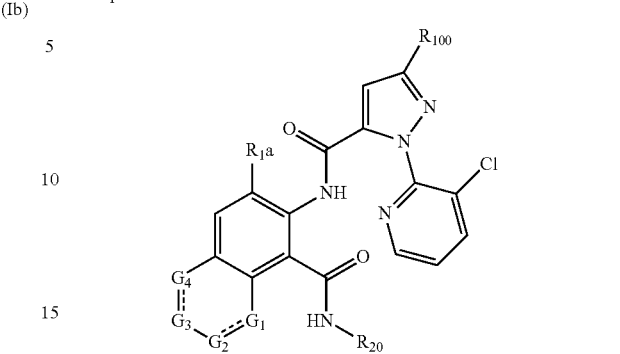

(Ib)

| Line | R₁a | R₁₀₀ | R₂₀ |
|---|---|---|---|
| A.1.284 | CN | OCF₃ | |
| A.1.285 | CN | OCF₃ | |
| A.1.286 | CN | OCF₃ | CH(CH₃)₂CH₂SCH₃ |
| A.1.287 | CN | OCF₃ | CH(CH₃)₂CH₂S(O)CH₃ |
| A.1.288 | CN | OCF₃ | CH(CH₃)₂CH₂S(O)₂CH₃ |
| A.1.289 | I | CF₃ | H |
| A.1.290 | I | CF₃ | CH₃ |
| A.1.291 | I | CF₃ | CH₂CH₃ |
| A.1.292 | I | CF₃ | CH(CH₃)CH₃ |
| A.1.293 | I | CF₃ | C(CH₃)(CH₃)CH₃ |
| A.1.294 | I | CF₃ | |
| A.1.295 | I | CF₃ | |
| A.1.296 | I | CF₃ | |
| A.1.297 | I | CF₃ | |
| A.1.298 | I | CF₃ | CH(CH₃)₂CH₂SCH₃ |
| A.1.299 | I | CF₃ | CH(CH₃)₂CH₂S(O)CH₃ |
| A.1.300 | I | CF₃ | CH(CH₃)₂CH₂S(O)₂CH₃ |
| A.1.301 | I | OCH₂CF₃ | H |
| A.1.302 | I | OCH₂CF₃ | CH₃ |
| A.1.303 | I | OCH₂CF₃ | CH₂CH₃ |
| A.1.304 | I | OCH₂CF₃ | CH(CH₃)CH₃ |
| A.1.305 | I | OCH₂CF₃ | C(CH₃)(CH₃)CH₃ |
| A.1.306 | I | OCH₂CF₃ | |

TABLE A-continued

Compounds of formula Ib:

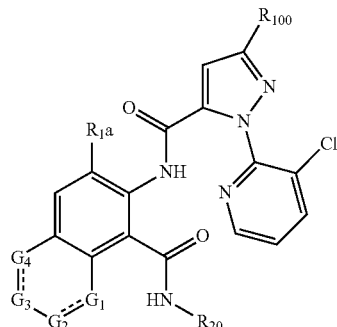
(Ib)

| Line | R₁a | R₁₀₀ | R₂₀ |
|---|---|---|---|
| A.1.307 | I | OCH₂CF₃ | |
| A.1.308 | I | OCH₂CF₃ | |
| A.1.309 | I | OCH₂CF₃ | |
| A.1.310 | I | OCH₂CF₃ | CH(CH₃)₂CH₂SCH₃ |
| A.1.311 | I | OCH₂CF₃ | CH(CH₃)₂CH₂S(O)CH₃ |
| A.1.312 | I | OCH₂CF₃ | CH(CH₃)₂CH₂S(O)₂CH₃ |
| A.1.313 | I | Br | H |
| A.1.314 | I | Br | CH₃ |
| A.1.315 | I | Br | CH₂CH₃ |
| A.1.316 | I | Br | CH(CH₃)CH₃ |
| A.1.317 | I | Br | C(CH₃)(CH₃)CH₃ |
| A.1.318 | I | Br | |
| A.1.319 | I | Br | |
| A.1.320 | I | Br | |
| A.1.321 | I | Br | |
| A.1.322 | I | Br | CH(CH₃)₂CH₂SCH₃ |
| A.1.323 | I | Br | CH(CH₃)₂CH₂S(O)CH₃ |
| A.1.324 | I | Br | CH(CH₃)₂CH₂S(O)₂CH₃ |
| A.1.325 | I | Cl | H |
| A.1.326 | I | Cl | CH₃ |
| A.1.327 | I | Cl | CH₂CH₃ |
| A.1.328 | I | Cl | CH(CH₃)CH₃ |
| A.1.329 | I | Cl | C(CH₃)(CH₃)CH₃ |

TABLE A-continued

Compounds of formula Ib:

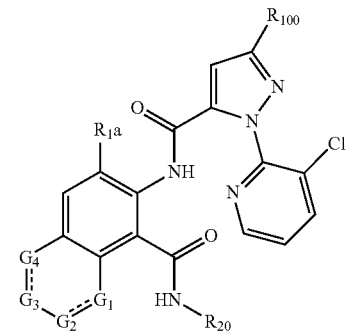
(Ib)

| Line | R₁a | R₁₀₀ | R₂₀ |
|---|---|---|---|
| A.1.330 | I | Cl | |
| A.1.331 | I | Cl | |
| A.1.332 | I | Cl | |
| A.1.333 | I | Cl | |
| A.1.334 | I | Cl | CH(CH₃)₂CH₂SCH₃ |
| A.1.335 | I | Cl | CH(CH₃)₂CH₂S(O)CH₃ |
| A.1.336 | I | Cl | CH(CH₃)₂CH₂S(O)₂CH₃ |
| A.1.337 | I | CF₂H | H |
| A.1.338 | I | CF₂H | CH₃ |
| A.1.339 | I | CF₂H | CH₂CH₃ |
| A.1.340 | I | CF₂H | CH(CH₃)CH₃ |
| A.1.341 | I | CF₂H | C(CH₃)(CH₃)CH₃ |
| A.1.342 | I | CF₂H | |
| A.1.343 | I | CF₂H | |
| A.1.344 | I | CF₂H | |
| A.1.345 | I | CF₂H | |
| A.1.346 | I | CF₂H | CH(CH₃)₂CH₂SCH₃ |
| A.1.347 | I | CF₂H | CH(CH₃)₂CH₂S(O)CH₃ |
| A.1.348 | I | CF₂H | CH(CH₃)₂CH₂S(O)₂CH₃ |
| A.1.349 | I | OCF₃ | H |
| A.1.350 | I | OCF₃ | CH₃ |
| A.1.351 | I | OCF₃ | CH₂CH₃ |

TABLE A-continued

Compounds of formula Ib:

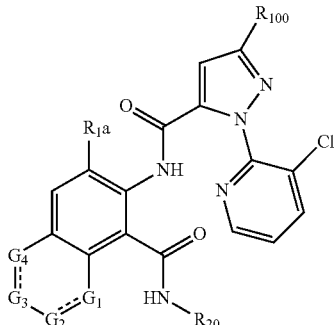
(Ib)

| Line | R$_1$a | R$_{100}$ | R$_{20}$ |
|---|---|---|---|
| A.1.352 | I | OCF$_3$ | CH(CH$_3$)CH$_3$ |
| A.1.353 | I | OCF$_3$ | C(CH$_3$)(CH$_3$)CH$_3$ |
| A.1.354 | I | OCF$_3$ |  |
| A.1.355 | I | OCF$_3$ |  |
| A.1.356 | I | OCF$_3$ |  |
| A.1.357 | I | OCF$_3$ |  |
| A.1.358 | I | OCF$_3$ | CH(CH$_3$)$_2$CH$_2$SCH$_3$ |
| A.1.359 | I | OCF$_3$ | CH(CH$_3$)$_2$CH$_2$S(O)CH$_3$ |
| A.1.360 | I | OCF$_3$ | CH(CH$_3$)$_2$CH$_2$S(O)$_2$CH$_3$ |
| A.1.361 | C≡CH | CF$_3$ | H |
| A.1.362 | C≡CH | CF$_3$ | CH$_3$ |
| A.1.363 | C≡CH | CF$_3$ | CH$_2$CH$_3$ |
| A.1.364 | C≡CH | CF$_3$ | CH(CH$_3$)CH$_3$ |
| A.1.365 | C≡CH | CF$_3$ | C(CH$_3$)(CH$_3$)CH$_3$ |
| A.1.366 | C≡CH | CF$_3$ |  |
| A.1.367 | C≡CH | CF$_3$ |  |
| A.1.368 | C≡CH | CF$_3$ |  |
| A.1.369 | C≡CH | CF$_3$ |  |
| A.1.370 | C≡CH | CF$_3$ | CH(CH$_3$)$_2$CH$_2$SCH$_3$ |
| A.1.371 | C≡CH | CF$_3$ | CH(CH$_3$)$_2$CH$_2$S(O)CH$_3$ |
| A.1.372 | C≡CH | CF$_3$ | CH(CH$_3$)$_2$CH$_2$S(O)$_2$CH$_3$ |
| A.1.373 | C≡CH | OCH$_2$CF$_3$ | H |
| A.1.374 | C≡CH | OCH$_2$CF$_3$ | CH$_3$ |
| A.1.375 | C≡CH | OCH$_2$CF$_3$ | CH$_2$CH$_3$ |
| A.1.376 | C≡CH | OCH$_2$CF$_3$ | CH(CH$_3$)CH$_3$ |
| A.1.377 | C≡CH | OCH$_2$CF$_3$ | C(CH$_3$)(CH$_3$)CH$_3$ |
| A.1.378 | C≡CH | OCH$_2$CF$_3$ |  |
| A.1.379 | C≡CH | OCH$_2$CF$_3$ |  |
| A.1.380 | C≡CH | OCH$_2$CF$_3$ |  |
| A.1.381 | C≡CH | OCH$_2$CF$_3$ | 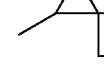 |
| A.1.382 | C≡CH | OCH$_2$CF$_3$ | CH(CH$_3$)$_2$CH$_2$SCH$_3$ |
| A.1.383 | C≡CH | OCH$_2$CF$_3$ | CH(CH$_3$)$_2$CH$_2$S(O)CH$_3$ |
| A.1.384 | C≡CH | OCH$_2$CF$_3$ | CH(CH$_3$)$_2$CH$_2$S(O)$_2$CH$_3$ |
| A.1.385 | C≡CH | Br | H |
| A.1.386 | C≡CH | Br | CH$_3$ |
| A.1.387 | C≡CH | Br | CH$_2$CH$_3$ |
| A.1.388 | C≡CH | Br | CH(CH$_3$)CH$_3$ |
| A.1.389 | C≡CH | Br | C(CH$_3$)(CH$_3$)CH$_3$ |
| A.1.390 | C≡CH | Br |  |
| A.1.391 | C≡CH | Br | 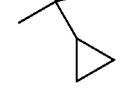 |
| A.1.392 | C≡CH | Br |  |

TABLE A-continued

Compounds of formula Ib:

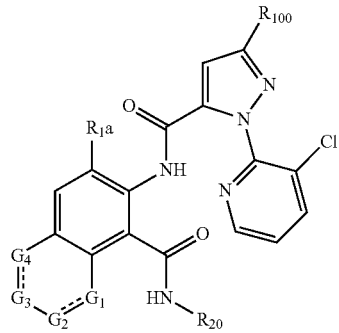
(Ib)

| Line | $R_1a$ | $R_{100}$ | $R_{20}$ |
|---|---|---|---|
| A.1.393 | C≡CH | Br | (spiro bicyclic) |
| A.1.394 | C≡CH | Br | $CH(CH_3)_2CH_2SCH_3$ |
| A.1.395 | C≡CH | Br | $CH(CH_3)_2CH_2S(O)CH_3$ |
| A.1.396 | C≡CH | Br | $CH(CH_3)_2CH_2S(O)_2CH_3$ |
| A.1.397 | C≡CH | Cl | H |
| A.1.398 | C≡CH | Cl | $CH_3$ |
| A.1.399 | C≡CH | Cl | $CH_2CH_3$ |
| A.1.400 | C≡CH | Cl | $CH(CH_3)CH_3$ |
| A.1.401 | C≡CH | Cl | $C(CH_3)(CH_3)CH_3$ |
| A.1.402 | C≡CH | Cl | (cyclopropylmethyl) |
| A.1.403 | C≡CH | Cl | (bicyclopropyl) |
| A.1.404 | C≡CH | Cl | (spiro bicyclic) |
| A.1.405 | C≡CH | Cl | (spiro bicyclic) |
| A.1.406 | C≡CH | Cl | $CH(CH_3)_2CH_2SCH_3$ |
| A.1.407 | C≡CH | Cl | $CH(CH_3)_2CH_2S(O)CH_3$ |
| A.1.408 | C≡CH | Cl | $CH(CH_3)_2CH_2S(O)_2CH_3$ |
| A.1.409 | C≡CH | $CF_2H$ | H |
| A.1.410 | C≡CH | $CF_2H$ | $CH_3$ |
| A.1.411 | C≡CH | $CF_2H$ | $CH_2CH_3$ |
| A.1.412 | C≡CH | $CF_2H$ | $CH(CH_3)CH_3$ |
| A.1.413 | C≡CH | $CF_2H$ | $C(CH_3)(CH_3)CH_3$ |
| A.1.414 | C≡CH | $CF_2H$ | (cyclopropylmethyl) |
| A.1.415 | C≡CH | $CF_2H$ | (bicyclopropyl) |
| A.1.416 | C≡CH | $CF_2H$ | (spiro bicyclic) |
| A.1.417 | C≡CH | $CF_2H$ | (spiro bicyclic) |
| A.1.418 | C≡CH | $CF_2H$ | $CH(CH_3)_2CH_2SCH_3$ |
| A.1.419 | C≡CH | $CF_2H$ | $CH(CH_3)_2CH_2S(O)CH_3$ |
| A.1.420 | C≡CH | $CF_2H$ | $CH(CH_3)_2CH_2S(O)_2CH_3$ |
| A.1.421 | C≡CH | $OCF_3$ | H |
| A.1.422 | C≡CH | $OCF_3$ | $CH_3$ |
| A.1.423 | C≡CH | $OCF_3$ | $CH_2CH_3$ |
| A.1.424 | C≡CH | $OCF_3$ | $CH(CH_3)CH_3$ |
| A.1.425 | C≡CH | $OCF_3$ | $C(CH_3)(CH_3)CH_3$ |
| A.1.426 | C≡CH | $OCF_3$ | (cyclopropylmethyl) |
| A.1.427 | C≡CH | $OCF_3$ | (bicyclopropyl) |
| A.1.428 | C≡CH | $OCF_3$ | (spiro bicyclic) |
| A.1.429 | C≡CH | $OCF_3$ | (spiro bicyclic) |
| A.1.430 | C≡CH | $OCF_3$ | $CH(CH_3)_2CH_2SCH_3$ |
| A.1.431 | C≡CH | $OCF_3$ | $CH(CH_3)_2CH_2S(O)CH_3$ |
| A.1.432 | C≡CH | $OCF_3$ | $CH(CH_3)_2CH_2S(O)_2CH_3$ |
| A.1.433 | H | $CF_3$ | H |
| A.1.434 | H | $CF_3$ | $CH_3$ |
| A.1.435 | H | $CF_3$ | $CH_2CH_3$ |
| A.1.436 | H | $CF_3$ | $CH(CH_3)CH_3$ |
| A.1.437 | H | $CF_3$ | $C(CH_3)(CH_3)CH_3$ |
| A.1.438 | H | $CF_3$ | (bicyclopropyl) |

TABLE A-continued

Compounds of formula Ib:

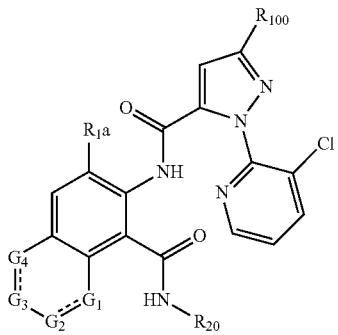

(Ib)

| Line | R₁a | R₁₀₀ | R₂₀ |
|---|---|---|---|
| A.1.439 | H | CF₃ | |
| A.1.440 | H | CF₃ | |
| A.1.441 | H | CF₃ | |
| A.1.442 | H | CF₃ | CH(CH₃)₂CH₂SCH₃ |
| A.1.443 | H | CF₃ | CH(CH₃)₂CH₂S(O)CH₃ |
| A.1.444 | H | CF₃ | CH(CH₃)₂CH₂S(O)₂CH₃ |
| A.1.445 | H | OCH₂CF₃ | H |
| A.1.446 | H | OCH₂CF₃ | CH₃ |
| A.1.447 | H | OCH₂CF₃ | CH₂CH₃ |
| A.1.448 | H | OCH₂CF₃ | CH(CH₃)CH₃ |
| A.1.449 | H | OCH₂CF₃ | C(CH₃)(CH₃)CH₃ |
| A.1.450 | H | OCH₂CF₃ | |
| A.1.451 | H | OCH₂CF₃ | |
| A.1.452 | H | OCH₂CF₃ | |
| A.1.453 | H | OCH₂CF₃ | |
| A.1.454 | H | OCH₂CF₃ | CH(CH₃)₂CH₂SCH₃ |
| A.1.455 | H | OCH₂CF₃ | CH(CH₃)₂CH₂S(O)CH₃ |
| A.1.456 | H | OCH₂CF₃ | CH(CH₃)₂CH₂S(O)₂CH₃ |
| A.1.457 | H | Br | H |
| A.1.458 | H | Br | CH₃ |
| A.1.459 | H | Br | CH₂CH₃ |
| A.1.460 | H | Br | CH(CH₃)CH₃ |
| A.1.461 | H | Br | C(CH₃)(CH₃)CH₃ |

TABLE A-continued

Compounds of formula Ib:

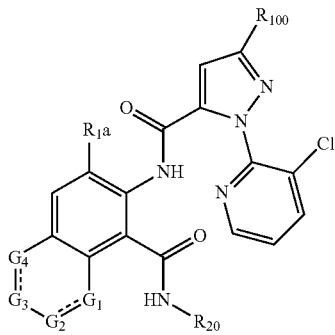

(Ib)

| Line | R₁a | R₁₀₀ | R₂₀ |
|---|---|---|---|
| A.1.462 | H | Br | |
| A.1.463 | H | Br | 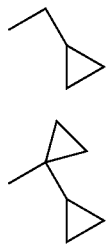 |
| A.1.464 | H | Br | |
| A.1.465 | H | Br | 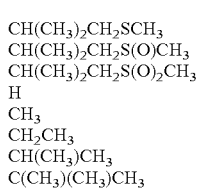 |
| A.1.466 | H | Br | CH(CH₃)₂CH₂SCH₃ |
| A.1.467 | H | Br | CH(CH₃)₂CH₂S(O)CH₃ |
| A.1.468 | H | Br | CH(CH₃)₂CH₂S(O)₂CH₃ |
| A.1.469 | H | Cl | H |
| A.1.470 | H | Cl | CH₃ |
| A.1.471 | H | Cl | CH₂CH₃ |
| A.1.472 | H | Cl | CH(CH₃)CH₃ |
| A.1.473 | H | Cl | C(CH₃)(CH₃)CH₃ |
| A.1.474 | H | Cl | |
| A.1.475 | H | Cl | 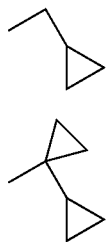 |
| A.1.476 | H | Cl | 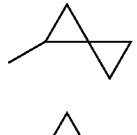 |
| A.1.477 | H | Cl | 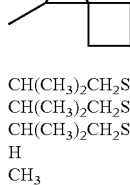 |
| A.1.478 | H | Cl | CH(CH₃)₂CH₂SCH₃ |
| A.1.479 | H | Cl | CH(CH₃)₂CH₂S(O)CH₃ |
| A.1.480 | H | Cl | CH(CH₃)₂CH₂S(O)₂CH₃ |
| A.1.481 | H | CF₂H | H |
| A.1.482 | H | CF₂H | CH₃ |

TABLE A-continued

Compounds of formula Ib:

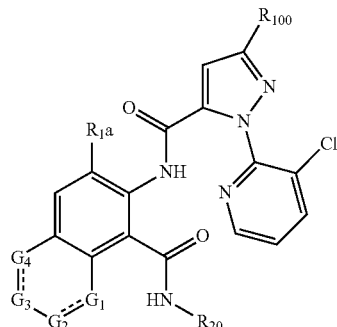

(Ib)

| Line | R₁a | R₁₀₀ | R₂₀ |
|---|---|---|---|
| A.1.483 | H | CF₂H | CH₂CH₃ |
| A.1.484 | H | CF₂H | CH(CH₃)CH₃ |
| A.1.485 | H | CF₂H | C(CH₃)(CH₃)CH₃ |
| A.1.486 | H | CF₂H |  |
| A.1.487 | H | CF₂H |  |
| A.1.488 | H | CF₂H |  |
| A.1.489 | H | CF₂H |  |
| A.1.490 | H | CF₂H | CH(CH₃)₂CH₂SCH₃ |
| A.1.491 | H | CF₂H | CH(CH₃)₂CH₂S(O)CH₃ |
| A.1.492 | H | CF₂H | CH(CH₃)₂CH₂S(O)₂CH₃ |
| A.1.493 | H | OCF₃ | H |
| A.1.494 | H | OCF₃ | CH₃ |
| A.1.495 | H | OCF₃ | CH₂CH₃ |
| A.1.496 | H | OCF₃ | CH(CH₃)CH₃ |
| A.1.497 | H | OCF₃ | C(CH₃)(CH₃)CH₃ |
| A.1.498 | H | OCF₃ | 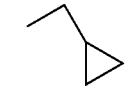 |
| A.1.499 | H | OCF₃ |  |
| A.1.500 | H | OCF₃ |  |
| A.1.501 | H | OCF₃ |  |
| A.1.502 | H | OCF₃ | CH(CH₃)₂CH₂SCH₃ |

TABLE A-continued

Compounds of formula Ib:

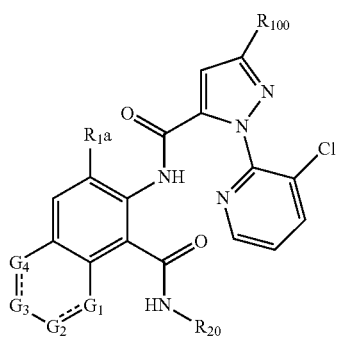

(Ib)

| Line | R₁a | R₁₀₀ | R₂₀ |
|---|---|---|---|
| A.1.503 | H | OCF₃ | CH(CH₃)₂CH₂S(O)CH₃ |
| A.1.504 | H | OCF₃ | CH(CH₃)₂CH₂S(O)₂CH₃ |
| A.1.505 | Cl | OCH₃ | H |
| A.1.506 | Cl | OCH₃ | CH₃ |
| A.1.507 | Cl | OCH₃ | CH₂CH₃ |
| A.1.508 | Cl | OCH₃ | CH(CH₃)CH₃ |
| A.1.509 | Cl | OCH₃ | C(CH₃)(CH₃)CH₃ |
| A.1.510 | Cl | OCH₃ |  |
| A.1.511 | Cl | OCH₃ |  |
| A.1.512 | Cl | OCH₃ | 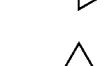 |
| A.1.513 | Cl | |  |
| A.1.514 | Cl | OCH₃ | CH(CH₃)₂CH₂SCH₃ |
| A.1.515 | Cl | OCH₃ | CH(CH₃)₂CH₂S(O)CH₃ |
| A.1.516 | Cl | OCH₃ | CH(CH₃)₂CH₂S(O)₂CH₃ |
| A.1.517 | Br | OCH₃ | H |
| A.1.518 | Br | OCH₃ | CH₃ |
| A.1.519 | Br | OCH₃ | CH₂CH₃ |
| A.1.520 | Br | OCH₃ | CH(CH₃)CH₃ |
| A.1.521 | Br | OCH₃ | C(CH₃)(CH₃)CH₃ |
| A.1.522 | Br | OCH₃ | 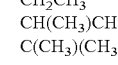 |
| A.1.523 | Br | OCH₃ |  |
| A.1.524 | Br | OCH₃ |  |

TABLE A-continued

Compounds of formula Ib:

(Ib)

| Line | R₁a | R₁₀₀ | R₂₀ |
|---|---|---|---|
| A.1.525 | Br | | (cyclopropyl-spirocyclobutyl-methyl) |
| A.1.526 | Br | OCH₃ | CH(CH₃)₂CH₂SCH₃ |
| A.1.527 | Br | OCH₃ | CH(CH₃)₂CH₂S(O)CH₃ |
| A.1.528 | Br | OCH₃ | CH(CH₃)₂CH₂S(O)₂CH₃ |
| A.1.529 | CH₃ | OCH₃ | H |
| A.1.530 | CH₃ | OCH₃ | CH₃ |
| A.1.531 | CH₃ | OCH₃ | CH₂CH₃ |
| A.1.532 | CH₃ | OCH₃ | CH(CH₃)CH₃ |
| A.1.533 | CH₃ | OCH₃ | C(CH₃)(CH₃)CH₃ |
| A.1.534 | CH₃ | OCH₃ | (methylcyclopropyl) |
| A.1.535 | CH₃ | OCH₃ | (bicyclopropyl-methyl) |
| A.1.536 | CH₃ | OCH₃ | (cyclopropyl-cyclopropyl-methyl) |
| A.1.537 | CH₃ | | (cyclopropyl-spirocyclobutyl-methyl) |
| A.1.538 | CH₃ | OCH₃ | CH(CH₃)₂CH₂SCH₃ |
| A.1.539 | CH₃ | OCH₃ | CH(CH₃)₂CH₂S(O)CH₃ |
| A.1.540 | CH₃ | OCH₃ | CH(CH₃)₂CH₂S(O)₂CH₃ |
| A.1.541 | H | OCH₃ | H |
| A.1.542 | H | OCH₃ | CH₃ |
| A.1.543 | H | OCH₃ | CH₂CH₃ |
| A.1.544 | H | OCH₃ | CH(CH₃)CH₃ |
| A.1.545 | H | OCH₃ | C(CH₃)(CH₃)CH₃ |
| A.1.546 | H | OCH₃ | (methylcyclopropyl) |
| A.1.547 | H | OCH₃ | (bicyclopropyl-methyl) |
| A.1.548 | H | OCH₃ | (methylbicyclopropyl) |
| A.1.549 | H | OCH₃ | (cyclopropyl-spirocyclobutyl-methyl) |
| A.1.550 | H | OCH₃ | CH(CH₃)₂CH₂SCH₃ |
| A.1.551 | H | OCH₃ | CH(CH₃)₂CH₂S(O)CH₃ |
| A.1.552 | H | OCH₃ | CH(CH₃)₂CH₂S(O)₂CH₃ |
| A.1.553 | C≡CH | OCH₃ | H |
| A.1.554 | C≡CH | OCH₃ | CH₃ |
| A.1.555 | C≡CH | OCH₃ | CH₂CH₃ |
| A.1.556 | C≡CH | OCH₃ | CH(CH₃)CH₃ |
| A.1.557 | C≡CH | OCH₃ | C(CH₃)(CH₃)CH₃ |
| A.1.558 | C≡CH | OCH₃ | (methylcyclopropyl) |
| A.1.559 | C≡CH | OCH₃ | (bicyclopropyl-methyl) |
| A.1.560 | C≡CH | OCH₃ | (cyclopropyl-cyclopropyl-methyl) |
| A.1.561 | C≡CH | OCH₃ | (cyclopropyl-spirocyclobutyl-methyl) |
| A.1.562 | C≡CH | OCH₃ | CH(CH₃)₂CH₂SCH₃ |
| A.1.563 | C≡CH | OCH₃ | CH(CH₃)₂CH₂S(O)CH₃ |
| A.1.564 | C≡CH | OCH₃ | CH(CH₃)₂CH₂S(O)₂CH₃ |

TABLE 1

This table discloses the 564 compounds T1.1.1 to T1.1.564 of the formula

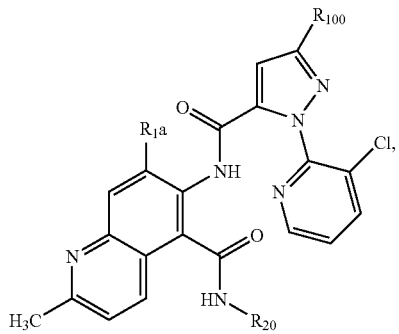

(T1)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A. For example, the specific compound T1.1.23 is the compound of the formula T1, in which each of the variables $R_{1a}$, $R_{20}$ and $R_{100}$ has the specific meaning given in the line A.1.23 of the Table A. According to the same system, also all of the other 564 specific compounds disclosed in the Table 1 as well as all of the specific compounds disclosed in the Tables 2 to 103 are specified analogously.

TABLE 2

This table discloses the 564 compounds T2.1.1 to T2.1.564 of the formula

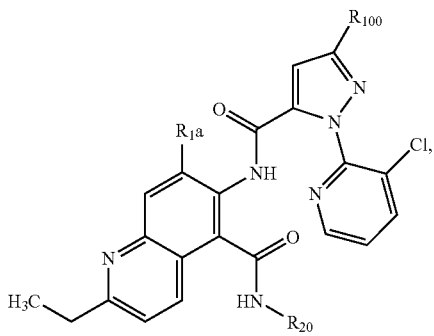

(T2)

in which, for each of these 564 specific compounds, each of the variables $R_{1a}$, $R_{20}$ and $R_{100}$ has the specific meaning given in the corresponding line, appropriately selected from the 564 lines A.1.1 to A.1.564 of the Table A.

TABLE 3

This table discloses the 564 compounds T3.1.1 to T3.1.564 of the formula

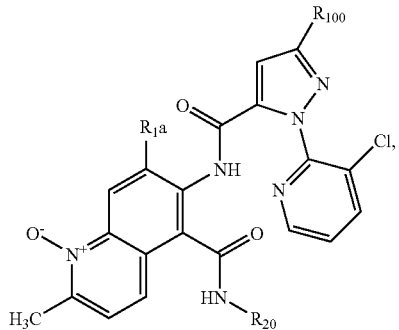

(T3)

in which, for each of these 564 specific compounds, each of the of the variables, $R_{1a}$, $R_{20}$ and $R_{100}$ has the specific meaning given in the corresponding line, appropriately selected from the 564 lines A.1.1 to A.1.564 of the Table A.

TABLE 4

This table discloses the 564 compounds T4.1.1 to T4.1.564 of the formula

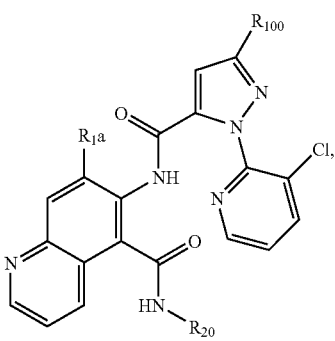

(T4)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 5

This table discloses the 564 compounds T5.1.1 to T5.1.564 of the formula

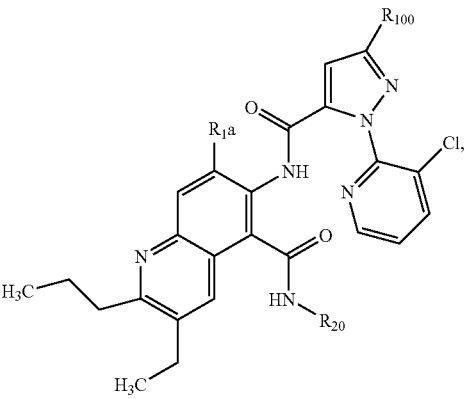

(T5)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 6

This table discloses the 564 compounds T6.1.1 to T6.1.564 of the formula

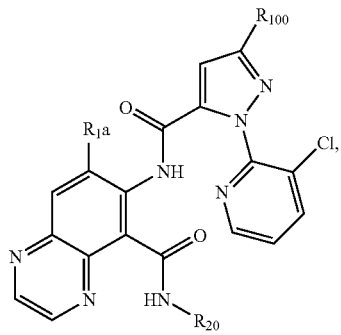

(T6)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 7

This table discloses the 564 compounds T7.1.1 to T7.1.564 of the formula

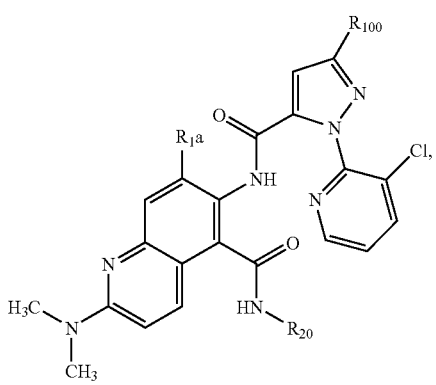

(T7)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 8

This table discloses the 564 compounds T8.1.1 to T8.1.564 of the formula

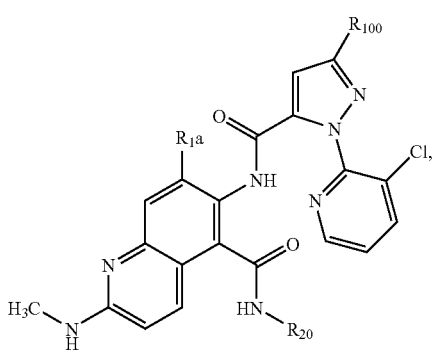

(T8)

in which, for each of these 564 specific compounds, each of the of the variables $R_{1a}$, $R_{20}$ and $R_{100}$ has the specific meaning given in the

TABLE 8-continued corresponding line, appropriately selected from the 564 lines A.1.1 to A.1.564 of the Table A.

TABLE 9

This table discloses the 564 compounds T9.1.1 to T9.1.564 of the formula

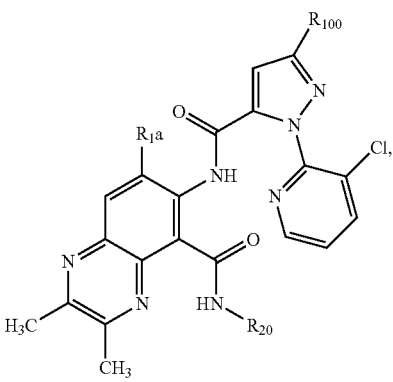

(T9)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 10

This table discloses the 564 compounds T10.1.1 to T10.1.564 of the formula

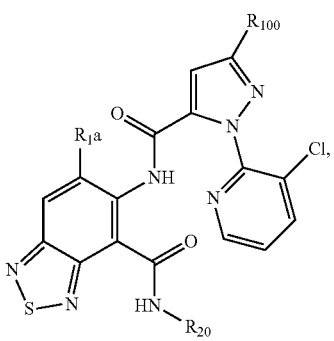

(T10)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 11

This table discloses the 564 compounds T11.1.1 to T11.1.564 of the formula

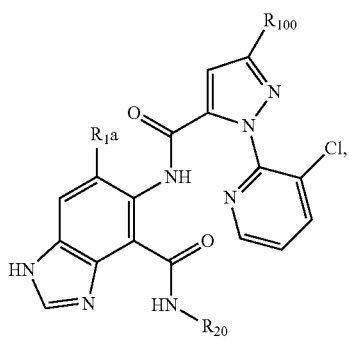

(T11)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 12

This table discloses the 564 compounds T12.1.1 to T12.1.564 of the formula

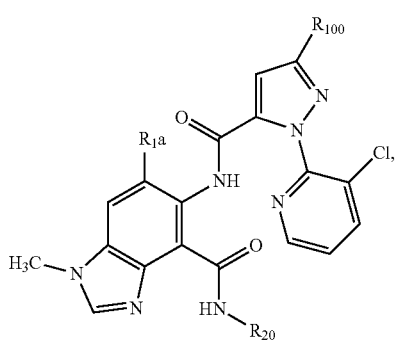

(T12)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 13

This table discloses the 564 compounds T13.1.1 to T13.1.564 of the formula

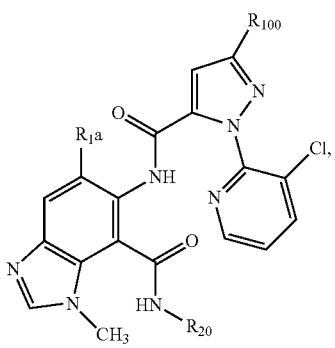

(T13)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 14

This table discloses the 564 compounds T14.1.1 to T14.1.564 of the formula

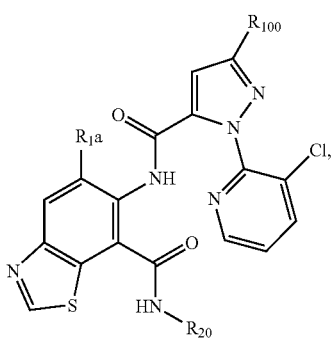

(T14)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 15

This table discloses the 564 compounds T15.1.1 to T15.1.564 of the formula

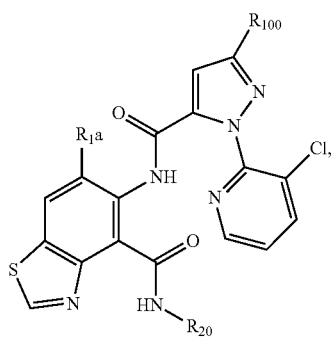
(T15)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 16

This table discloses the 564 compounds T16.1.1 to T16.1.564 of the formula

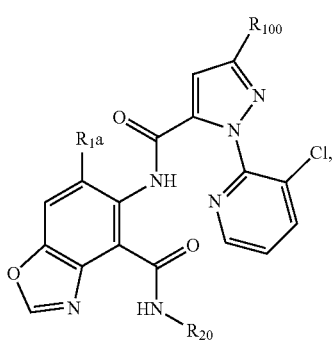
(T16)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 17

This table discloses the 564 compounds T17.1.1 to T17.1.564 of the formula

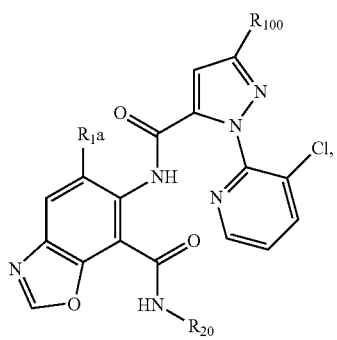
(T17)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 18

This table discloses the 564 compounds T18.1.1 to T18.1.564 of the formula

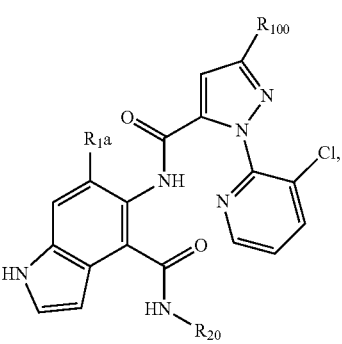
(T18)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 19

This table discloses the 564 compounds
T19.1.1 to T19.1.564 of the formula

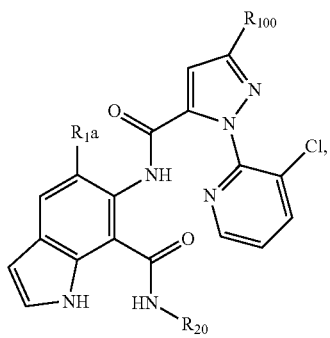

(T19)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 20

This table discloses the 564 compounds
T20.1.1 to T20.1.564 of the formula

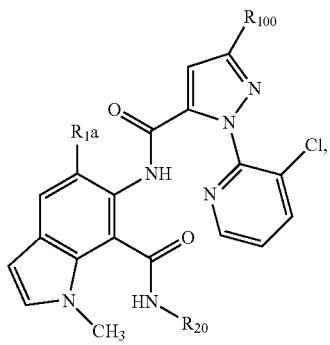

(T20)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 21

This table discloses the 564 compounds
T21.1.1 to T21.1.564 of the formula

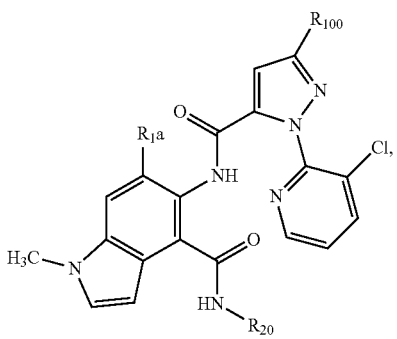

(T21)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 22

This table discloses the 564 compounds
T22.1.1 to T22.1.564 of the formula

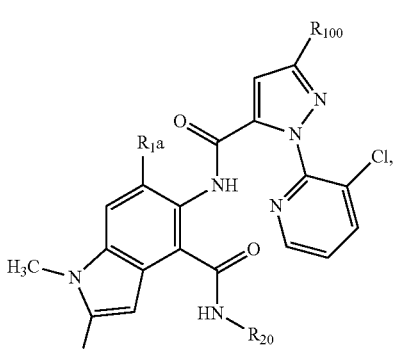

(T22)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 23

This table discloses the 564 compounds T23.1.1 to T23.1.564 of the formula

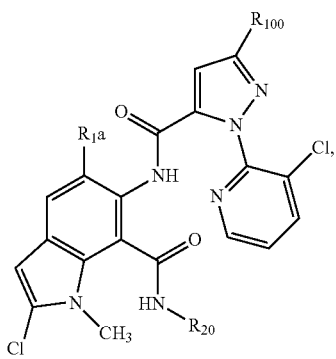

(T23)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 24

This table discloses the 564 compounds T24.1.1 to T24.1.564 of the formula

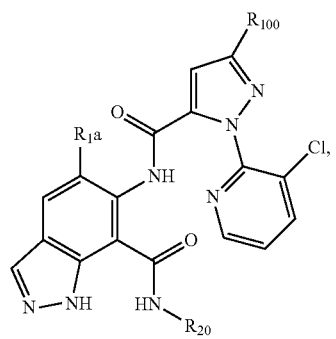

(T24)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 25

This table discloses the 564 compounds T25.1.1 to T25.1.564 of the formula

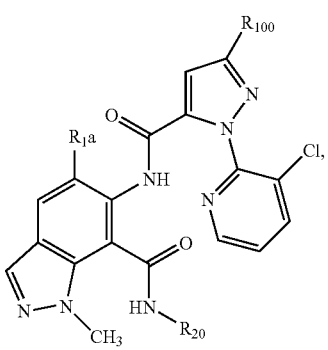

(T25)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 26

This table discloses the 564 compounds T26.1.1 to T26.1.564 of the formula

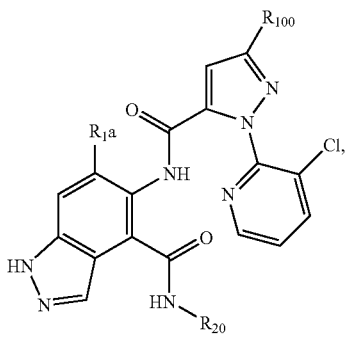

(T26)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 27

This table discloses the 564 compounds T27.1.1 to T27.1.564 of the formula

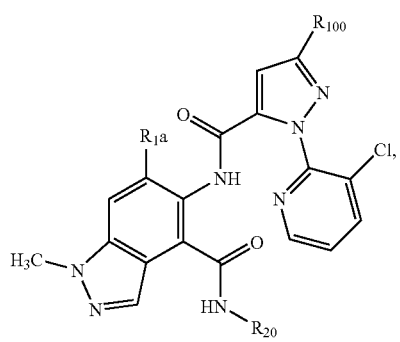

(T27)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 28

This table discloses the 564 compounds T28.1.1 to T28.1.564 of the formula

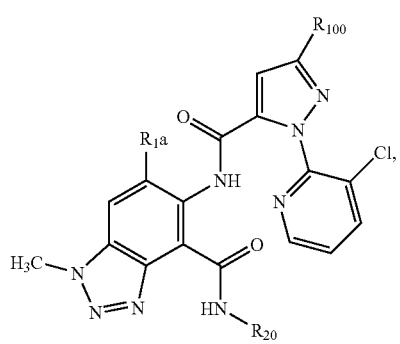

(T28)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 29

This table discloses the 564 compounds T29.1.1 to T29.1.564 of the formula

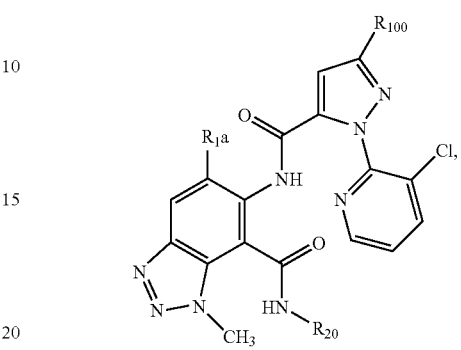

(T29)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 30

This table discloses the 564 compounds T30.1.1 to T30.1.564 of the formula

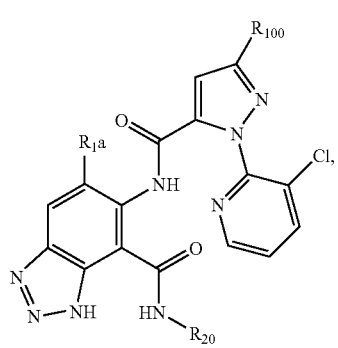

(T30)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 31

This table discloses the 564 compounds T31.1.1 to T31.1.564 of the formula

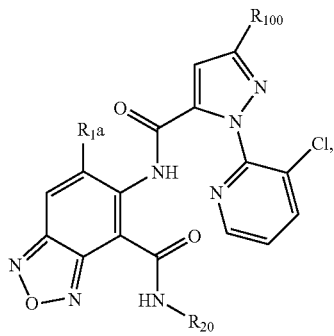

(T31)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 32

This table discloses the 564 compounds T32.1.1 to T32.1.564 of the formula

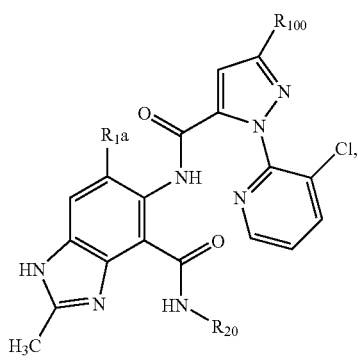

(T32)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 33

This table discloses the 564 compounds T33.1.1 to T33.1.564 of the formula

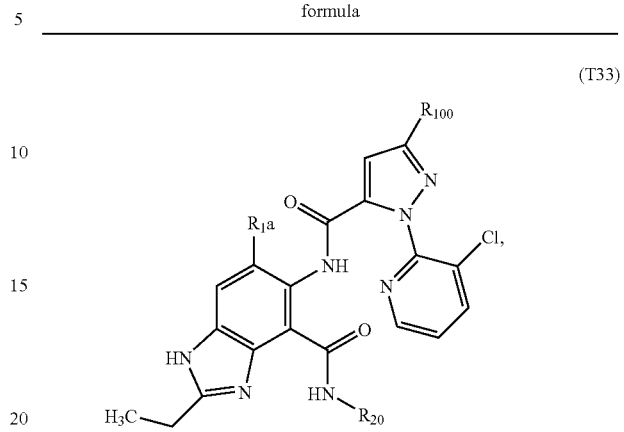

(T33)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 34

This table discloses the 564 compounds T34.1.1 to T34.1.564 of the formula

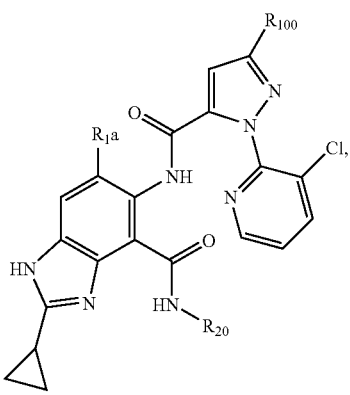

(T34)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 35

This table discloses the 564 compounds T35.1.1 to T35.1.564 of the formula

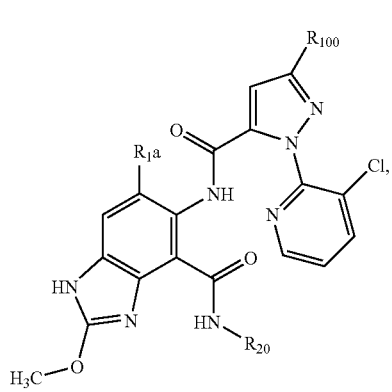

(T35)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 36

This table discloses the 564 compounds T36.1.1 to T36.1.525 of the formula

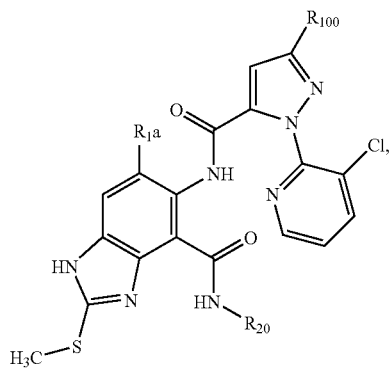

(T36)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 37

This table discloses the 564 compounds T37.1.1 to T37.1.564 of the formula

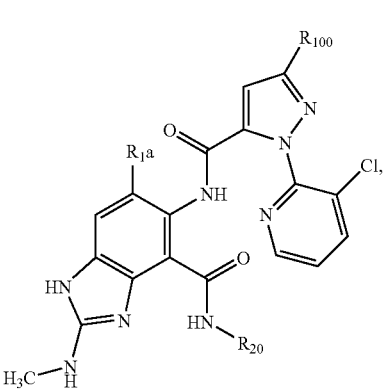

(T37)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 38

This table discloses the 564 compounds T38.1.1 to T38.1.564 of the formula

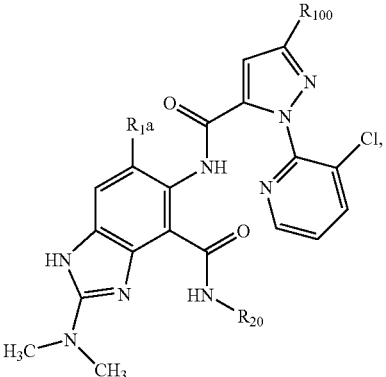

(T38)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 39

This table discloses the 564 compounds T39.1.1 to T39.1.564 of the formula

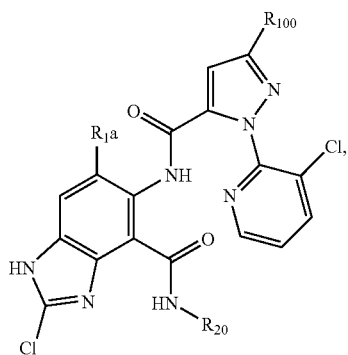

(T39)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 40

This table discloses the 564 compounds T40.1.1 to T40.1.564 of the formula

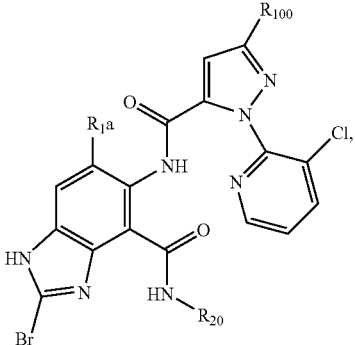

(T40)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 41

This table discloses the 564 compounds T41.1.1 to T41.1.564 of the formula

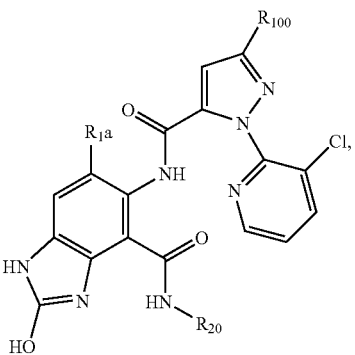

(T41)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 42

This table discloses the 564 compounds T42.1.1 to T42.1.564 of the formula

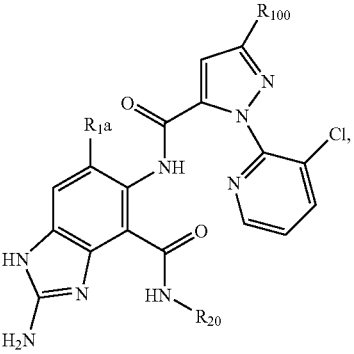

(T42)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 43

This table discloses the 564 compounds T43.1.1 to T43.1.564 of the formula

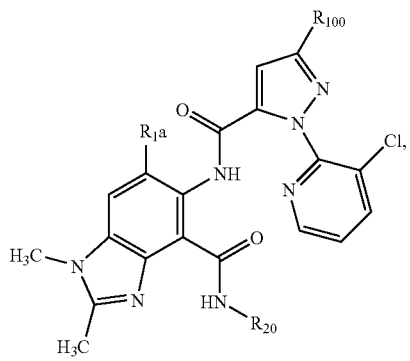

(T43)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 44

This table discloses the 564 compounds T44.1.1 to T44.1.564 of the formula

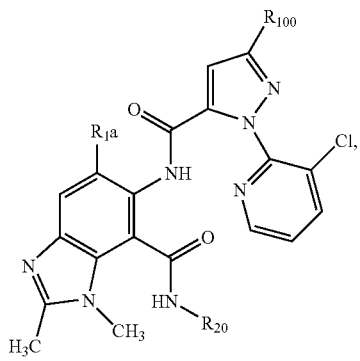

(T44)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 45

This table discloses the 564 compounds T45.1.1 to T45.1.564 of the formula

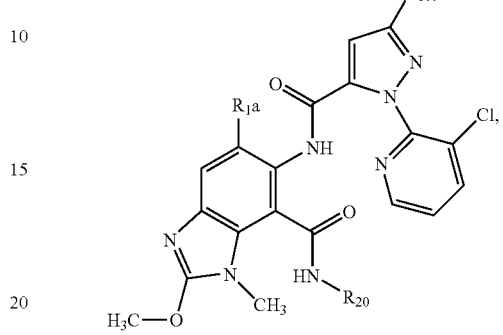

(T45)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 46

This table discloses the 564 compounds T46.1.1 to T46.1.564 of the formula

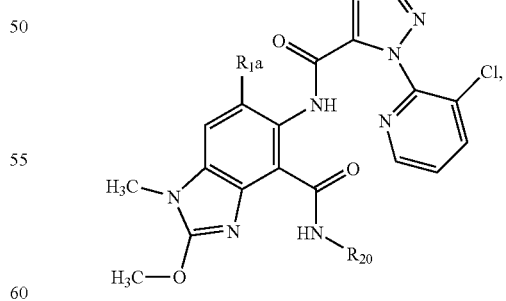

(T46)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 47

This table discloses the 564 compounds T47.1.1 to T47.1.564 of the formula

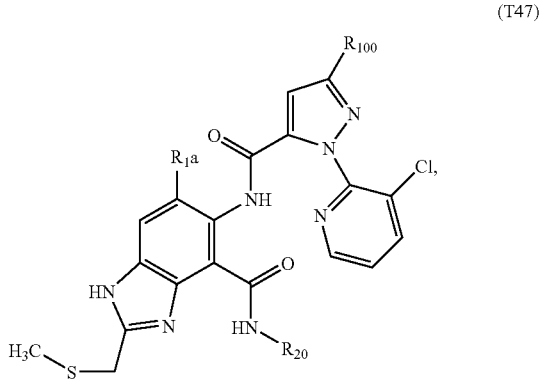

(T47)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 48

This table discloses the 564 compounds T48.1.1 to T48.1.564 of the formula

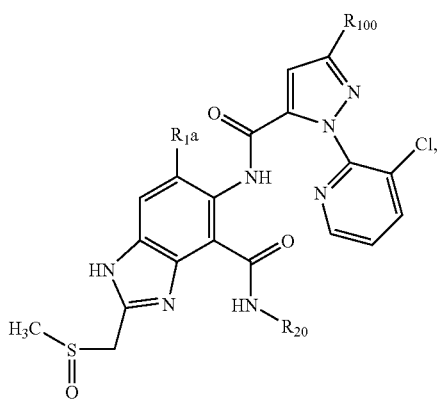

(T48)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 49

This table discloses the 564 compounds T49.1.1 to T49.1.564 of the formula

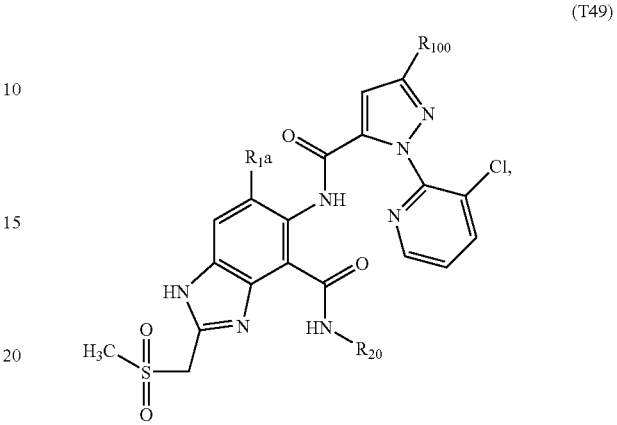

(T49)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 50

This table discloses the 564 compounds T50.1.1 to T50.1.564 of the formula

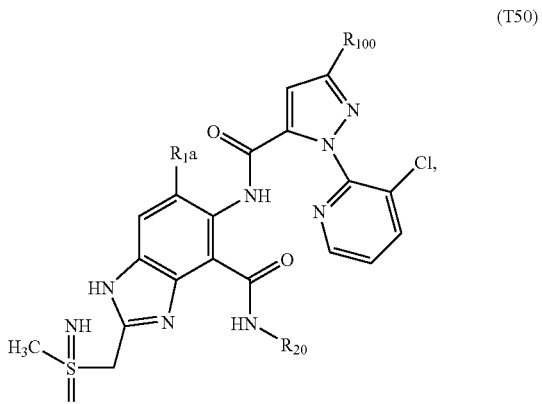

(T50)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 51

This table discloses the 564 compounds T51.1.1 to T51.1.564 of the formula (T51)

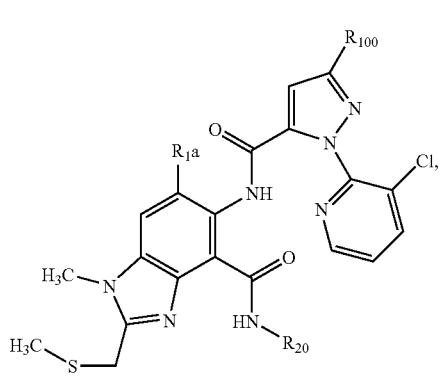

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 52

This table discloses the 564 compounds T52.1.1 to T52.1.564 of the formula (T52)

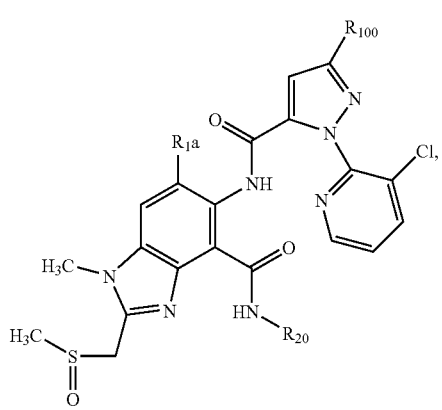

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 53

This table discloses the 564 compounds T53.1.1 to T53.1.564 of the formula (T53)

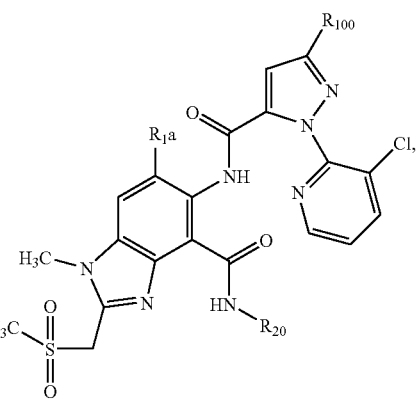

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 54

This table discloses the 564 compounds T54.1.1 to T54.1.564 of the formula (T54)

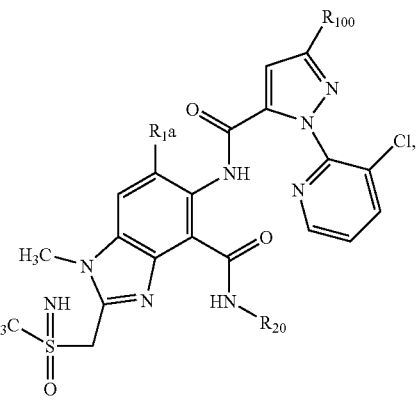

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 55

This table discloses the 564 compounds T55.1.1 to T55.1.564 of the formula

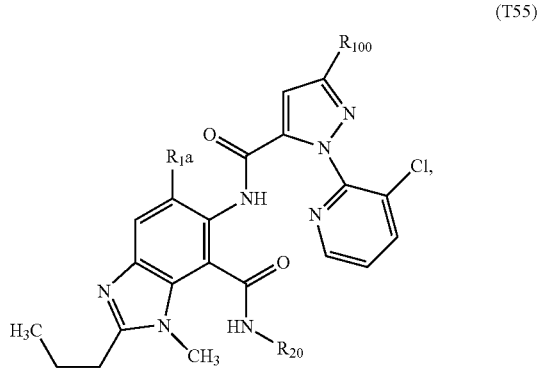

(T55)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 56

This table discloses the 564 compounds T56.1.1 to T56.1.564 of the formula

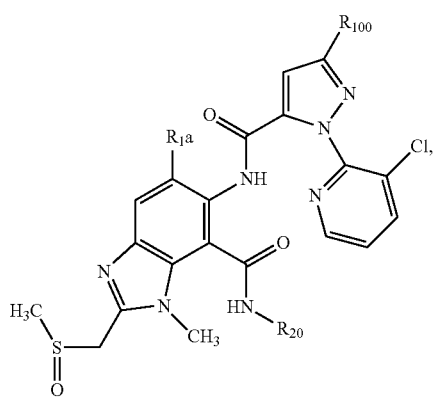

(T56)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 57

This table discloses the 564 compounds T57.1.1 to T57.1.564 of the formula

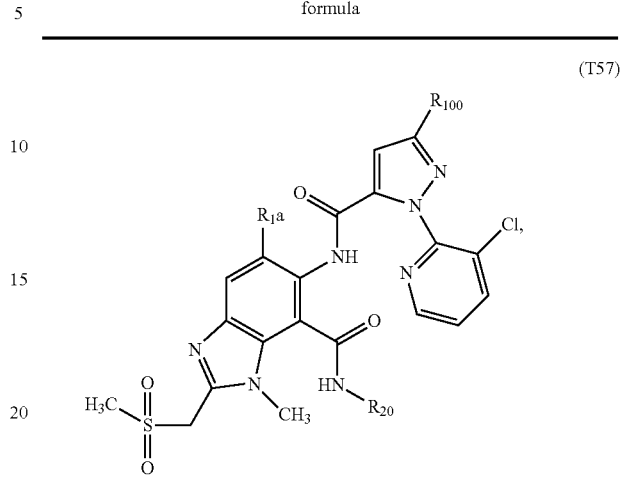

(T57)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 58

This table discloses the 564 compounds T58.1.1 to T58.1.564 of the formula

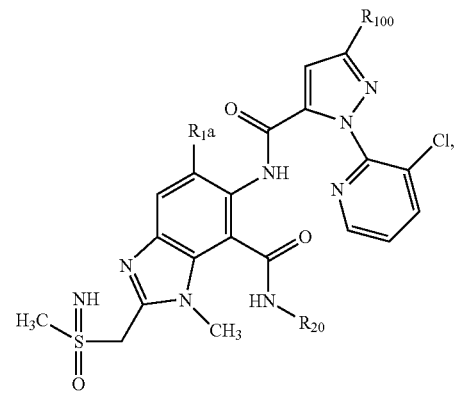

(T58)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 59

This table discloses the 564 compounds T59.1.1 to T59.1.564 of the formula

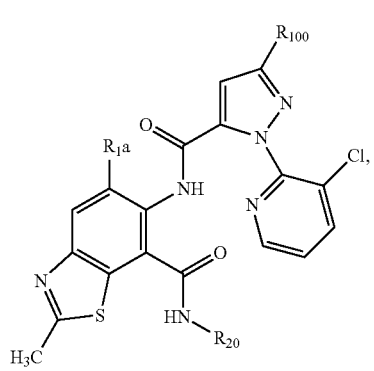

(T59)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 60

This table discloses the 564 compounds T60.1.1 to T60.1.564 of the formula

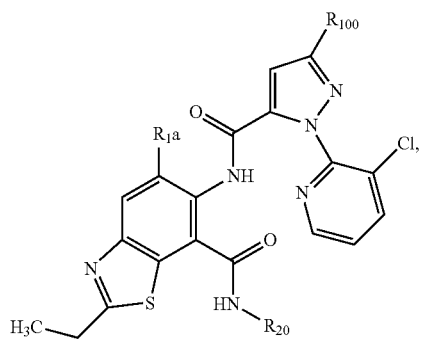

(T60)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 61

This table discloses the 564 compounds T61.1.1 to T61.1.564 of the formula

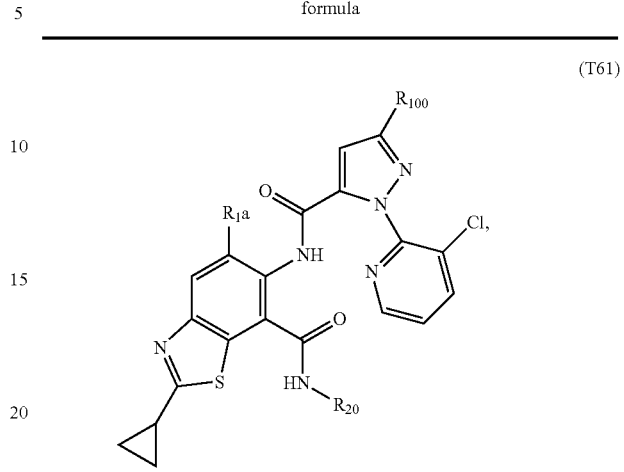

(T61)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 62

This table discloses the 564 compounds T62.1.1 to T62.1.564 of the formula

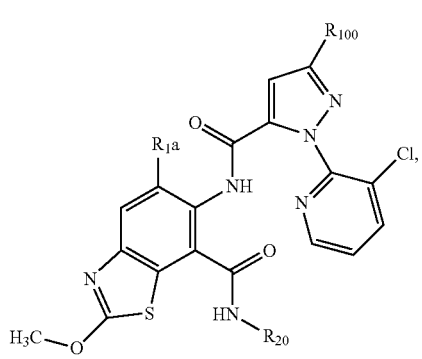

(T62)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 63

This table discloses the 564 compounds T63.1.1 to T63.1.564 of the formula

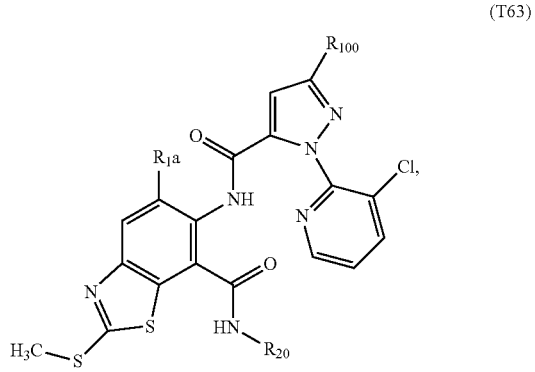

(T63)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 64

This table discloses the 564 compounds T64.1.1 to T64.1.564 of the formula

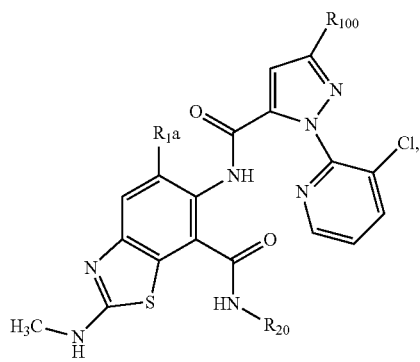

(T64)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 65

This table discloses the 564 compounds T65.1.1 to T65.1.564 of the formula

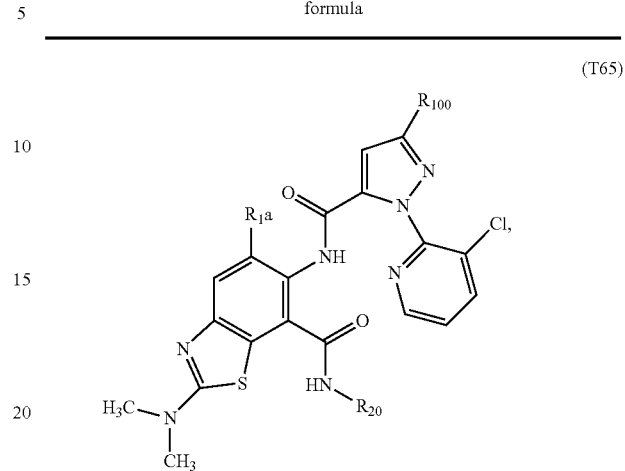

(T65)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 66

This table discloses the 564 compounds T66.1.1 to T66.1.564 of the formula

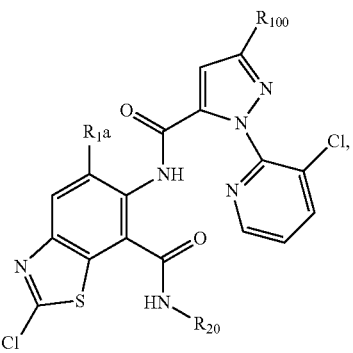

(T66)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 67

This table discloses the 564 compounds T67.1.1 to T67.1.564 of the formula

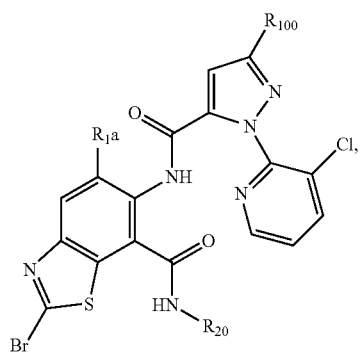

(T67)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 68

This table discloses the 564 compounds T68.1.1 to T68.1.564 of the formula

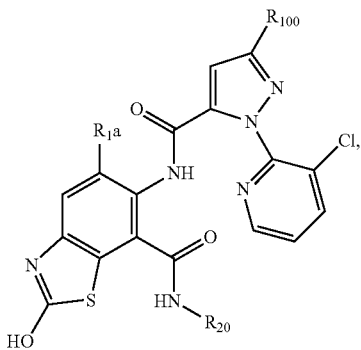

(T68)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 69

This table discloses the 564 compounds T69.1.1 to T69.1.564 of the formula

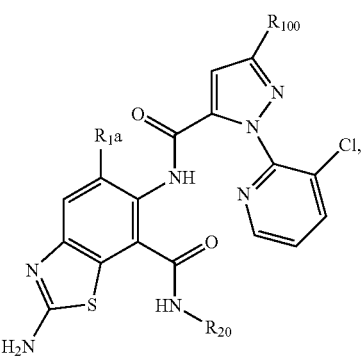

(T69)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 70

This table discloses the 564 compounds T70.1.1 to T70.1.564 of the formula

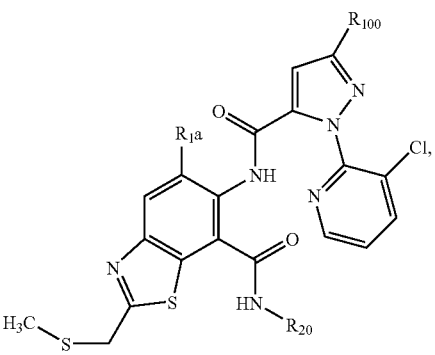

(T70)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 71

This table discloses the 564 compounds T71.1.1 to T71.1.564 of the formula

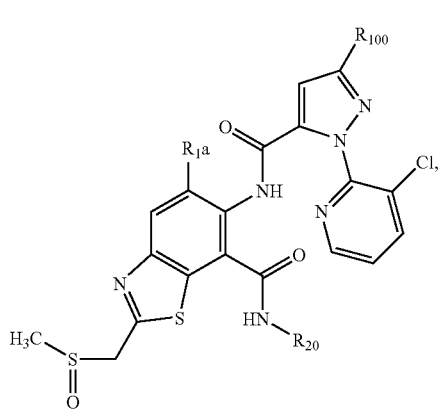

(T71)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 72

This table discloses the 564 compounds T72.1.1 to T72.1.564 of the formula

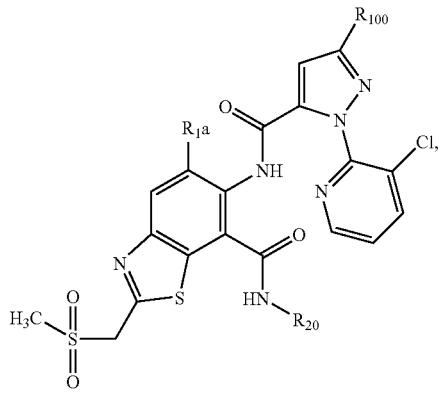

(T72)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 73

This table discloses the 564 compounds T73.1.1 to T73.1.564 of the formula

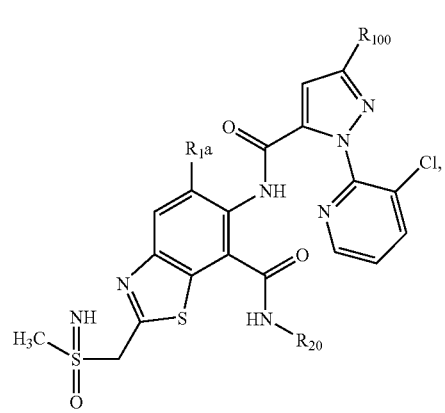

(T73)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 74

This table discloses the 564 compounds T74.1.1 to T74.1.564 of the formula

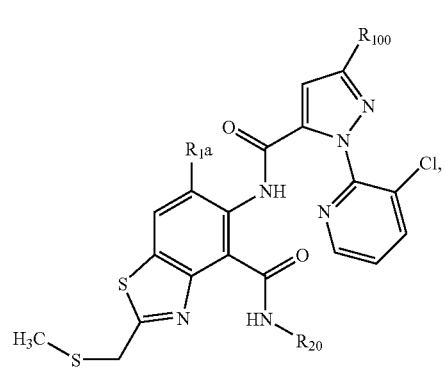

(T74)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 75

This table discloses the 564 compounds T75.1.1 to T75.1.564 of the formula

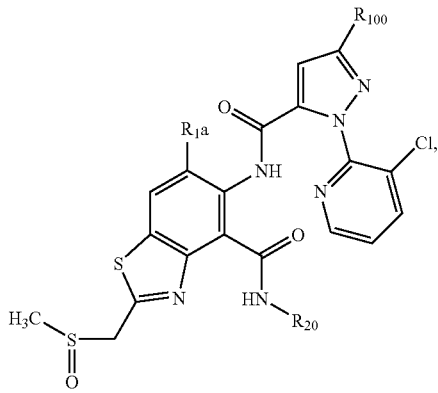

(T75)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 76

This table discloses the 564 compounds T76.1.1 to T76.1.564 of the formula

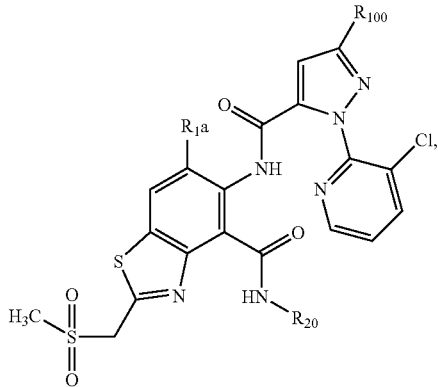

(T76)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 77

This table discloses the 564 compounds T77.1.1 to T77.1.564 of the formula

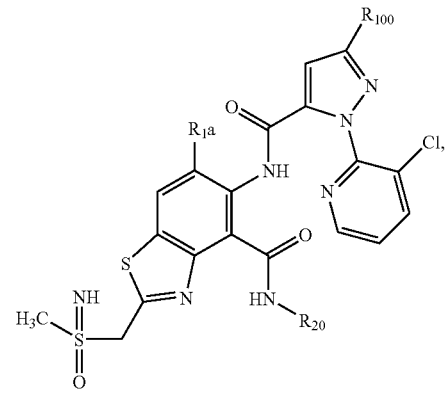

(T77)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 78

This table discloses the 564 compounds T78.1.1 to T78.1.564 of the formula

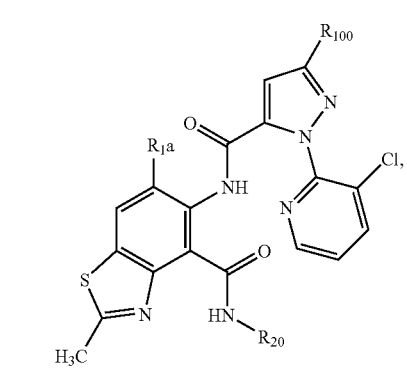

(T78)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 79

This table discloses the 564 compounds T79.1.1 to T79.1.564 of the formula

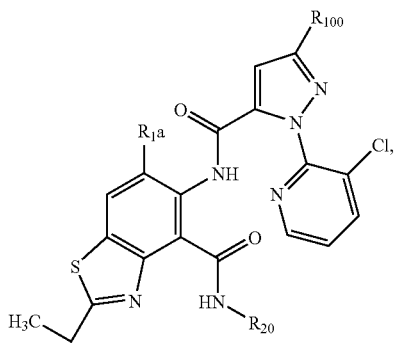

(T79)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 80

This table discloses the 564 compounds T80.1.1 to T80.1.564 of the formula

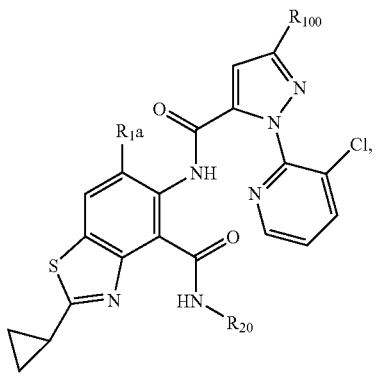

(T80)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the table A.

TABLE 81

This table discloses the 564 compounds T81.1.1 to T81.1.564 of the formula

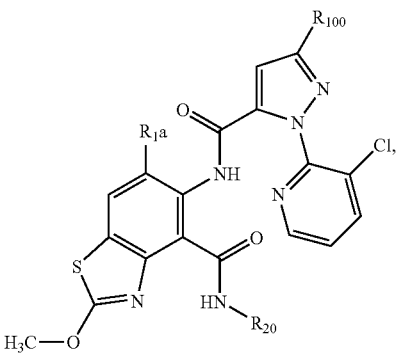

(T81)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 82

This table discloses the 564 compounds T82.1.1 to T82.1.564 of the formula

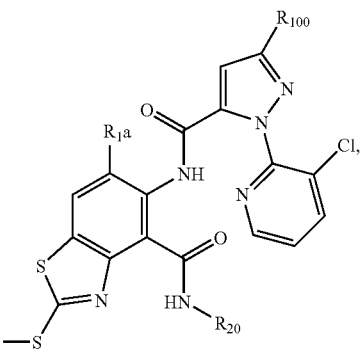

(T82)

in which, for each of these 564 specific compounds, each of the of the variables $R_{1a}$, $R_{20}$ and $R_{100}$ has the specific meaning given in the corresponding lines, appropriately selected from the 564 lines A.1.1 to A.1.564 of the Table A.

TABLE 83

This table discloses the 564 compounds T83.1.1 to T83.1.564 of the formula

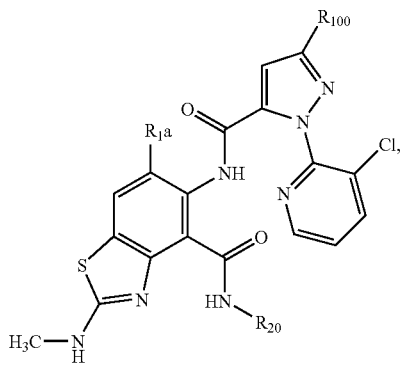

(T83)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 84

This table discloses the 564 compounds T84.1.1 to T84.1.564 of the formula

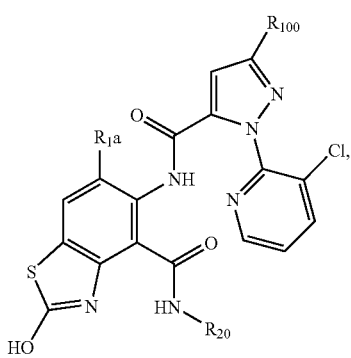

(T84)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 85

This table discloses the 564 compounds T85.1.1 to T85.1.564 of the formula

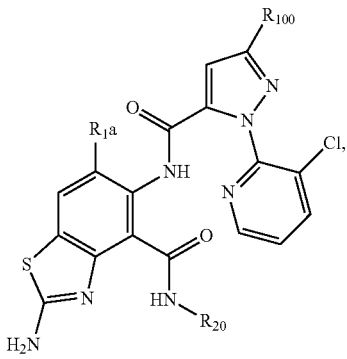

(T85)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 86

This table discloses the 564 compounds T86.1.1 to T86.1.564 of the formula

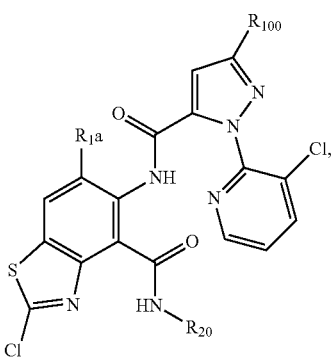

(T86)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 87

This table discloses the 564 compounds
T87.1.1 to T87.1.564 of the formula

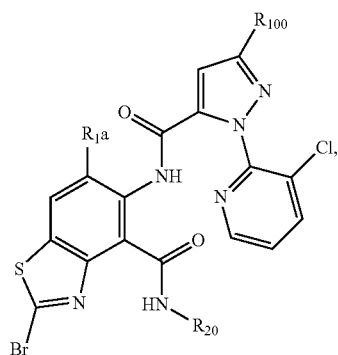
(T87)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 88

This table discloses the 564 compounds
T88.1.1 to T88.1.564 of the formula

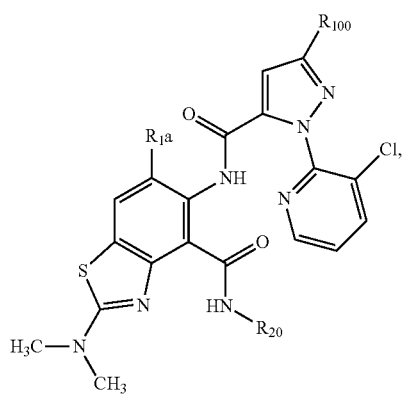
(T88)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 89

This table discloses the 564 compounds
T89.1.1 to T89.1.564 of the formula

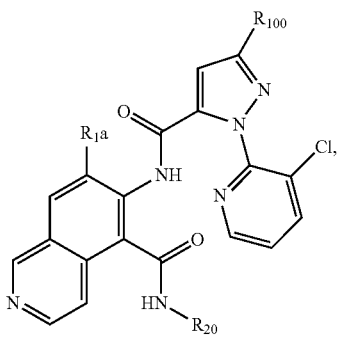
(T89)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 90

This table discloses the 564 compounds
T90.1.1 to T90.1.564 of the formula

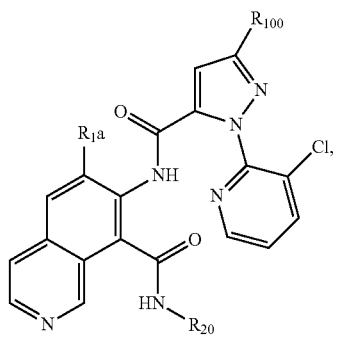
(T90)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 91

This table discloses the 564 compounds T91.1.1 to T91.1.564 of the formula

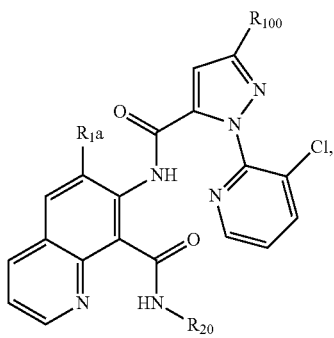

(T91)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 92

This table discloses the 564 compounds T92.1.1 to T92.1.564 of the formula

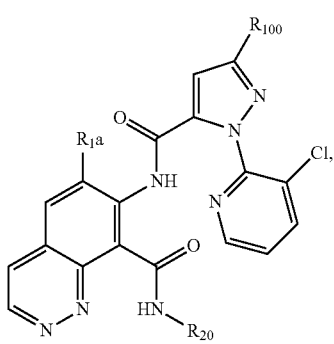

(T92)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 93

This table discloses the 564 compounds T93.1.1 to T93.1.564 of the formula

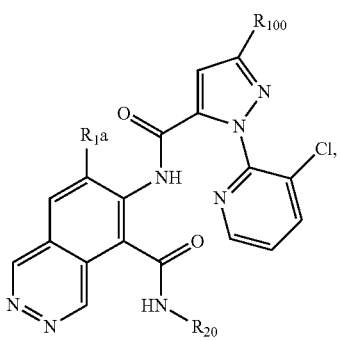

(T93)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 94

This table discloses the 564 compounds T94.1.1 to T94.1.564 of the formula

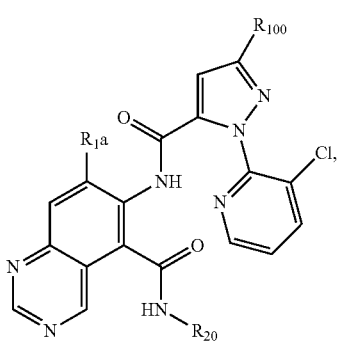

(T94)

in which, for each of these 564 specific compounds, each of the of the variables $R_{1a}$, $R_{20}$ and $R_{100}$ has the specific meaning given in the corresponding line, appropriately selected from the 564 lines A.1.1 to A.1.564 of the Table A.

TABLE 95

This table discloses the 564 compounds
T95.1.1 to T95.1.564 of the formula

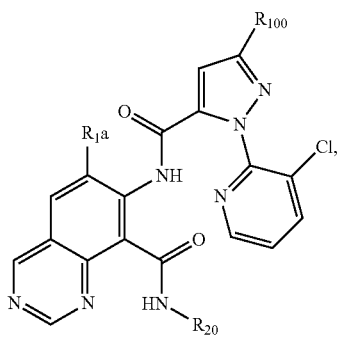

(T95)

in which, for each of these 564 specific compounds,
each of the of the variables $R_{1a}$, $R_{20}$ and
$R_{100}$ has the specific meaning given in the
corresponding line, appropriatety selected from
the 564 lines A.1.1 to A.1.564 of the Table A.

TABLE 96

This table discloses the 564 compounds
T96.1.1 to T96.1.564 of the formula

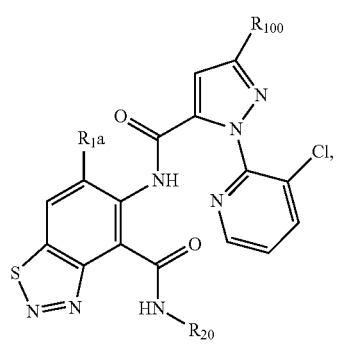

(T96)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 97

This table discloses the 564 compounds
T97.1.1 to T97.1.564 of the formula

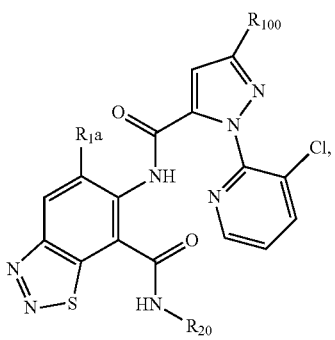

(T97)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 98

This table discloses the 564 compounds
T98.1.1 to T98.1.564 of the formula

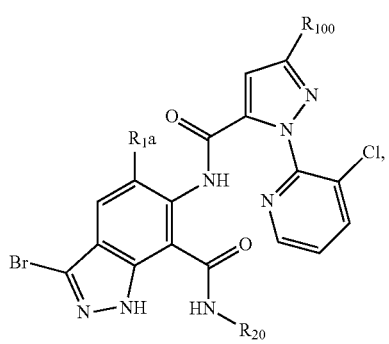

(T98)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

TABLE 99

This table discloses the 564 compounds
T99.1.1 to T99.1.564 of the formula

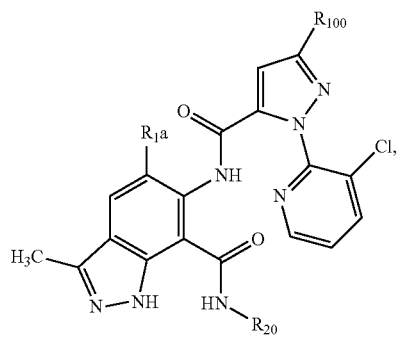

(T99)

in which, for each of these 564 specific compounds,
each of the of the variables $R_{1a}$, $R_{20}$ and
$R_{100}$ has the specific meaning given in the
corresponding line, appropriately selected from
the 564 lines A.1.1 to A.1.564 of the Table A.

Formulation examples (%=percent by weight)

Example F1: Emulsion concentrates

|  | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2: Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3: Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4: Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5: Wettable powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

Suspension Concentrate

| | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds of formulae T1 to T99 described in tables 1 to 97 of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chiorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-Smethylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfuram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfuram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and Yl-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluoron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-S-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexylure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl (prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/

Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, betacypermethrin (203)+TX, bifenthrin (76)+TX, bioallethrin (78)+TX, bioallethrin Scyclopentenyl isomer (alternative name) (79)+TX, bioethanomethrin [CCN]+TX, biopermethrin (908)+TX, bioresmethrin (80)+TX, bis(2-chloroethyl)ether (IUPAC name) (909)+TX, bistrifluoron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchforphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluoron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphosmethyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuronsodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, tefluben-zuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-

5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, an insecticide selected from the group consisting of the compound of formula A-1

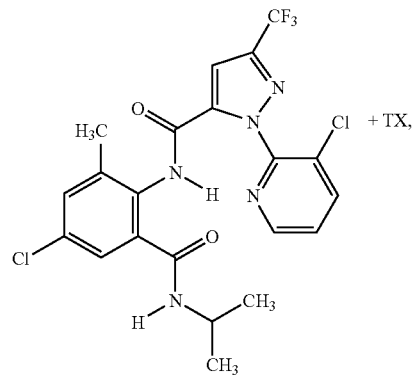

the formula A-2

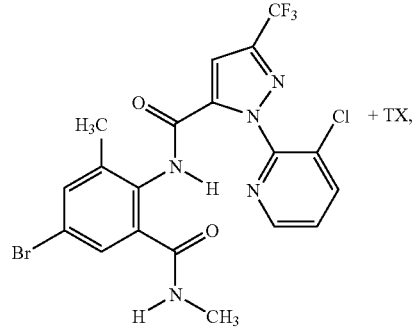

the formula A-3
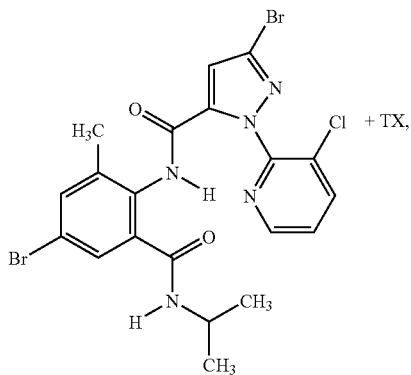
(A-3)
the formula A-7
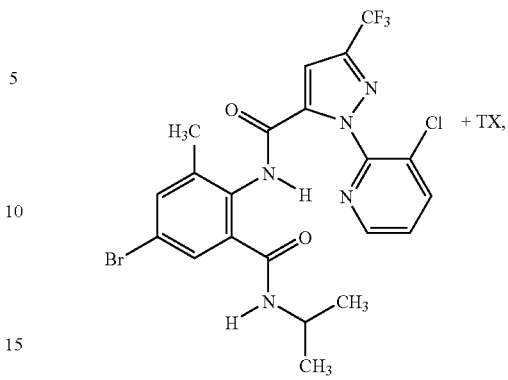
(A-7)
the formula A-4
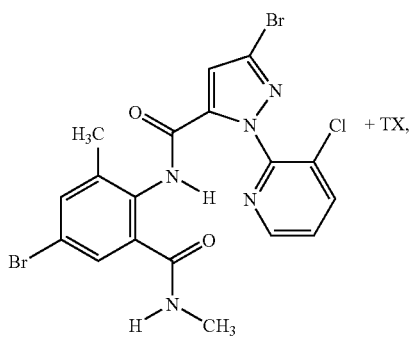
(A-4)
the formula A-8
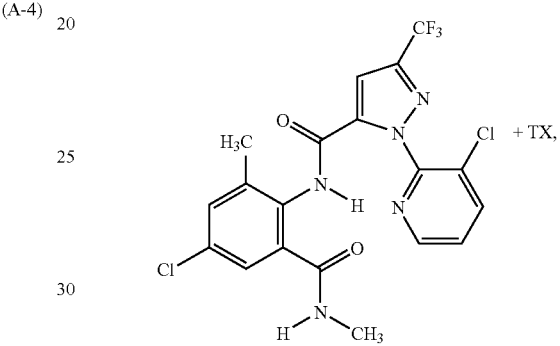
(A-8)
the formula A-5
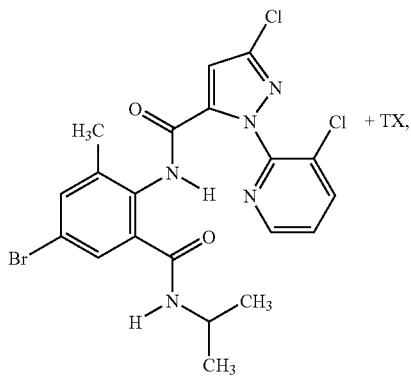
(A-5)
the formula A-9
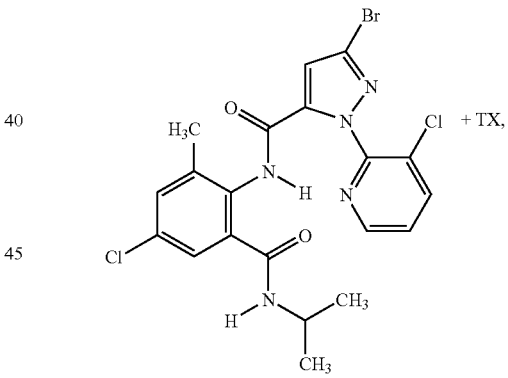
(A-9)
the formula A-6
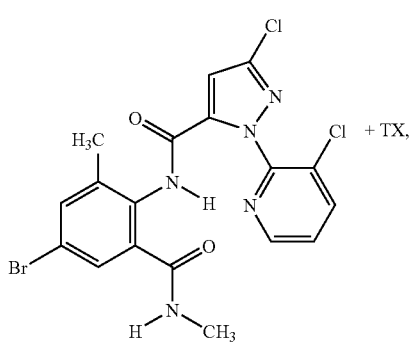
(A-6)
the formula A-10
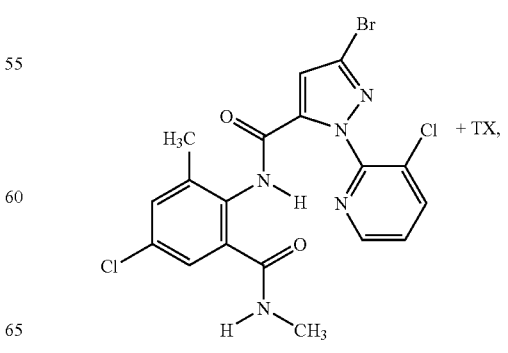
(A-10)

the formula A-11
(A-11)
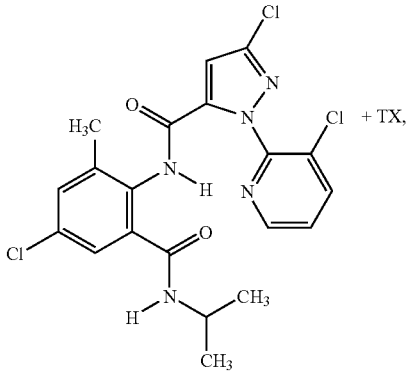 + TX,
the formula A-12
(A-12)
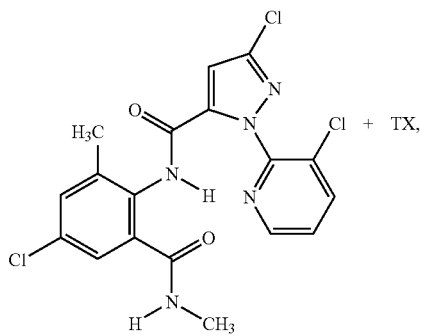 + TX,
the formula A-13
(A-13)
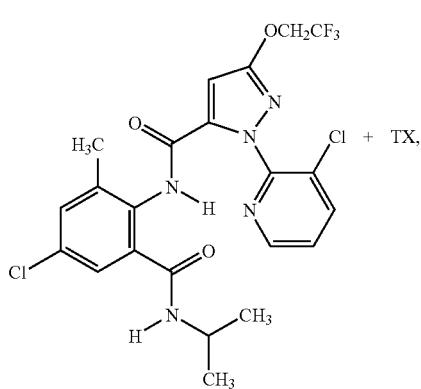 + TX,
the formula A-14
(A-14)
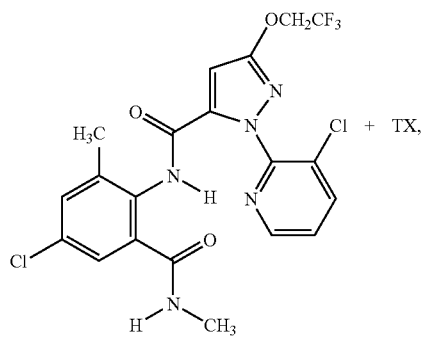 + TX,
the formula A-15
(A-15)
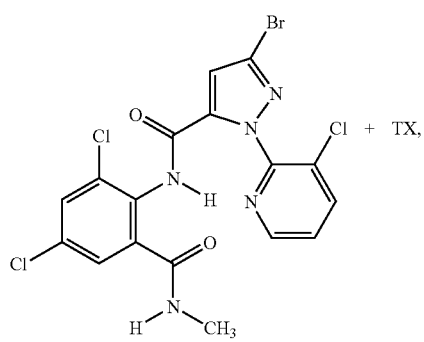 + TX,
the formula A-16
(A-16)
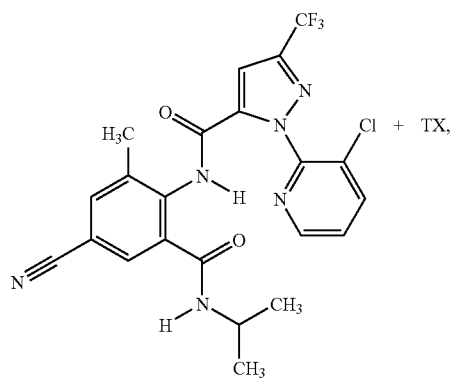 + TX,
the formula A-17
(A-17)
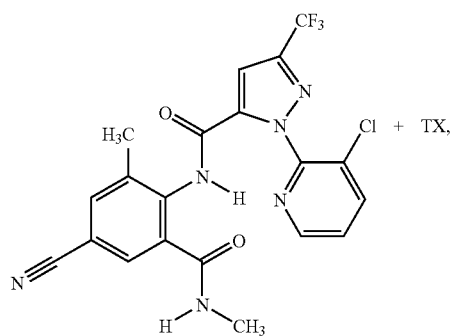 + TX, the formula A-18
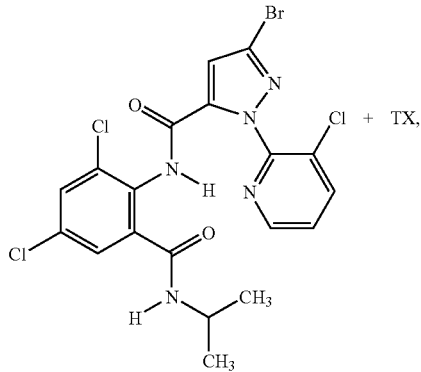
(A-18)
the formula A-19
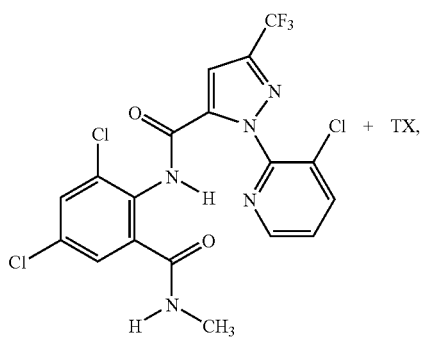
(A-19)
the formula A-20
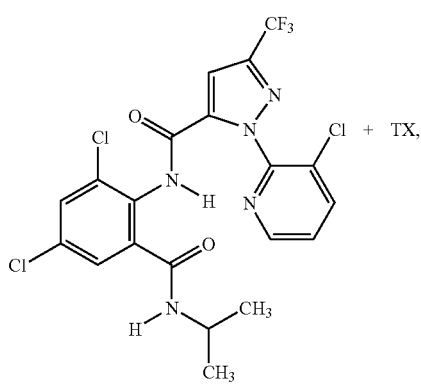
(A-20)
the formula A-21
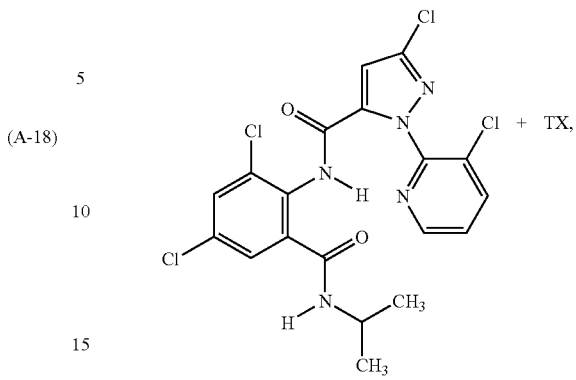
(A-21)
the formula A-22
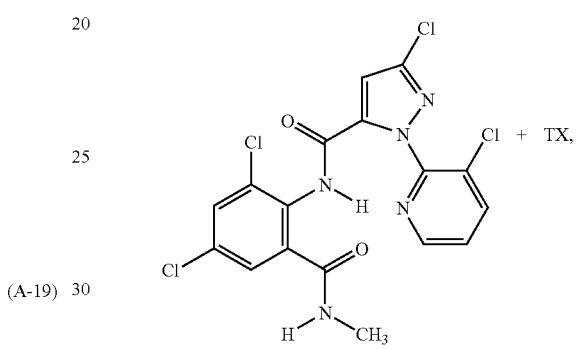
(A-22)
the formula A-23
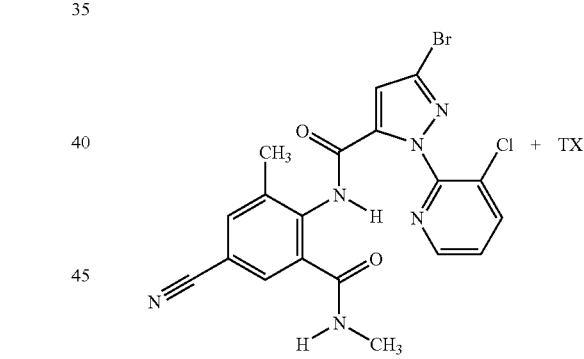
(A-23)
the formula A-24
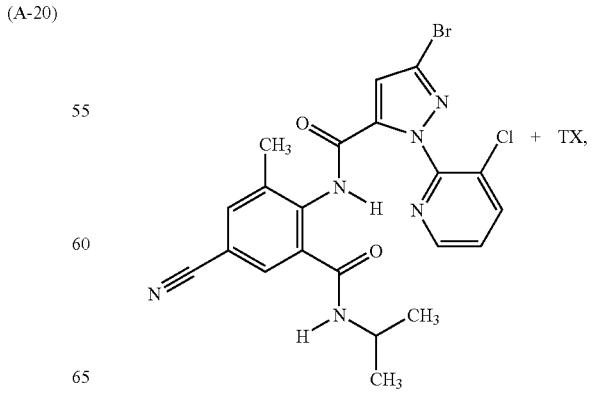
(A-24)

the formula A-25

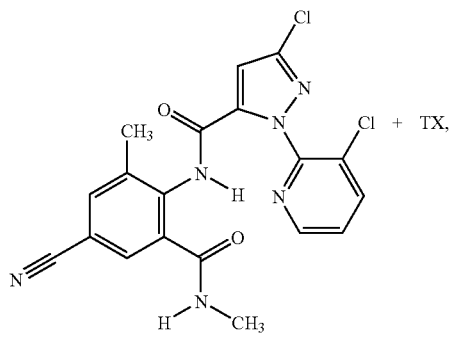

(A-25)

and the formula A-26

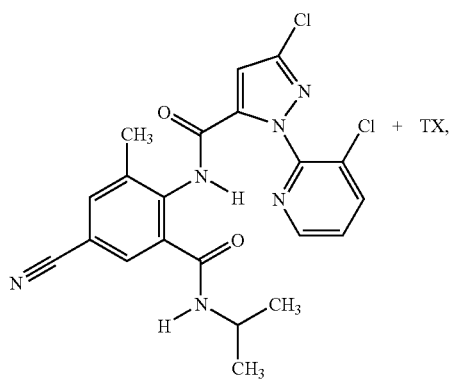

(A-26)

and biologically active compounds selected from the group consisting of Azaconazole (60207-31-0]+TX, Bitertanol [70585-36-3]+TX, Bromuconazole [116255-48-2]+TX, Cyproconazole [94361-06-5]+TX, Difenoconazole [119446-68-3]+TX, Diniconazole [83657-24-3]+TX, Epoxiconazole [106325-08-0]+TX, Fenbuconazole [114369-43-6]+TX, Fluquinconazole [136426-54-5]+TX, Flusilazole [85509-19-9]+TX, Flutriafol [76674-21-0]+TX, Hexaconazole [79983-71-4]+TX, Imazalil [35554-44-0]+TX, Imibenconazole [86598-92-7]+TX, Ipconazole [125225-28-7]+TX, Metconazole [125116-23-6]+TX, Myclobutanil [88671-89-0]+TX, Pefurazoate [101903-30-4]+TX, Penconazole [66246-88-6]+TX, Prothioconazole [178928-70-6]+TX, Pyrifenox [88283-41-4]+TX, Prochloraz [67747-09-5]+TX, Propiconazole [60207-90-1]+TX, Simeconazole [149508-90-7]+TX, Tebuconazole [107534-96-3]+TX, Tetraconazole [112281-77-3]+TX, Triadimefon [43121-43-3]+TX, Triadimenol [55219-65-3]+TX, Triflumizole [99387-89-0]+TX, Triticonazole [131983-72-7]+TX, Ancymidol [12771-68-5]+TX, Fenarimol [60168-88-9]+TX, Nuarimol [63284-71-9]+TX, Bupirimate [41483-43-6]+TX, Dimethirimol [5221-53-4]+TX, Ethirimol [23947-60-6]+TX, Dodemorph [1593-77-7]+TX, Fenpropidine [67306-00-7]+TX, Fenpropimorph [67564-91-4]+TX, Spiroxamine [118134-30-8]+TX, Tridemorph [81412-43-3]+TX, Cyprodinil [121552-61-2]+TX, Mepanipyrim [110235-47-7]+TX, Pyrimethanil [53112-28-0]+TX, Fenpiclonil [74738-17-3]+TX, Fludioxonil [131341-86-1]+TX, Benalaxyl [71626-11-4]+TX, Furalaxyl [57646-30-7]+TX, Metalaxyl [57837-19-1]+TX, R-Metalaxyl [70630-17-0]+TX, Ofurace [58810-48-3]+TX, Oxadixyl [77732-09-3]+TX, Benomyl [17804-35-2]+TX, Carbendazim [10605-21-7]+TX, Debacarb [62732-91-6]+TX, Fuberidazole [3878-19-1]+TX, Thiabendazole [148-79-8]+TX, Chlozolinate [84332-86-5]+TX, Dichlozoline [24201-58-9]+TX, Iprodione [36734-19-7]+TX, Myclozoline [54864-61-8]+TX, Procymidone [32809-16-8]+TX, Vinclozoline [50471-44-8]+TX, Boscalid [188425-85-6]+TX, Carboxin [5234-68-4]+TX, Fenfuram [24691-80-3]+TX, Flutolanil [66332-96-5]+TX, Mepronil [55814-41-0]+TX, Oxycarboxin [5259-88-1]+TX, Penthiopyrad [183675-82-3]+TX, Thifluzamide [130000-40-7]+TX, Guazatine [108173-90-6]+TX, Dodine [2439-10-3] [112-65-2] (freie Base)+TX, Iminoctadine [13516-27-3]+TX, Azoxystrobin [131860-33-8]+TX, Dimoxystrobin [149961-52-4]+TX, enestroburin {Proc. BCPC, Int. Congr., Glasgow, 2003, 1, 93}+TX, Fluoxastrobin [361377-29-9]+TX, Kresoxim-methyl [143390-89-0]+TX, Metominostrobin [133408-50-1]+TX, Trifloxystrobin [141517-21-7]+TX, Orysastrobin [248593-16-0]+TX, Picoxystrobin [117428-22-5]+TX, Pyraclostrobin [175013-18-0]+TX, Ferbam [14484-64-1]+TX, Mancozeb [8018-01-7]+TX, Maneb [12427-38-2]+TX, Metiram [9006-42-2]+TX, Propineb [12071-83-9]+TX, Thiram [137-26-8]+TX, Zineb [12122-67-7]+TX, Ziram [137-30-4]+TX, Captafol [2425-06-1]+TX, Captari [133-06-2]+TX, Dichlofluanid [1085-98-9]+TX, Fluoroimide [41205-21-4]+TX, Folpet [133-07-3]+TX, Tolylfluanid [731-27-1]+TX, Bordeaux Mixture [8011-63-0]+TX, Copperhydroxid [20427-59-2]+TX, Copperoxychlorid [1332-40-7]+TX, Coppersulfat [7758-98-7]+TX, Copperoxid [1317-39-1]+TX, Mancopper [53988-93-5]+TX, Oxine-copper [10380-28-6]+TX, Dinocap [131-72-6]+TX, Nitrothalisopropyl [10552-74-6]+TX, Edifenphos [17109-49-8]+TX, Iprobenphos [26087-47-8]+TX, Isoprothiolane [50512-35-1]+TX, Phosdiphen [36519-00-3]+TX, Pyrazophos [13457-18-6]+TX, Tolclofos-methyl [57018-04-9]+TX, Acibenzolar-S-methyl [135158-54-2]+TX, Anilazine [101-05-3]+TX, Benthiavalicarb [413615-35-7]+TX, Blasticidin-S [2079-00-7]+TX, Chinomethionat [2439-01-2]+TX, Chloroneb [2675-77-6]+TX, Chlorothalonil [1897-45-6]+TX, Cyflufenamid [180409-60-3]+TX, Cymoxanil [57966-95-7]+TX, Dichlone [117-80-6]+TX, Diclocymet [139920-32-4]+TX, Diclomezine [62865-36-5]+TX, Dicloran [99-30-9]+TX, Diethofencarb [87130-20-9]+TX, Dimethomorph [110488-70-5]+TX, SYP-LI90 (Flumorph) [211867-47-9]+TX, Dithianon [3347-22-6]+TX, Ethaboxam [162650-77-3]+TX, Etridiazole [2593-15-9]+TX, Famoxadone [131807-57-3]+TX, Fenamidone [161326-34-7]+TX, Fenoxanil [115852-48-7]+TX, Fentin [668-34-8]+TX, Ferimzone [89269-64-7]+TX, Fluazinam [79622-59-6]+TX, Fluopicolide [239110-15-7]+TX, Flusulfamide [106917-52-6]+TX, Fenhexamid [126833-17-8]+TX, Fosetylaluminium [39148-24-8]+TX, Hymexazol [10004-44-1]+TX, Iprovalicarb [140923-17-7]+TX, IKF-916 (Cyazofamid) [120116-88-3]+TX, Kasugamycin [6980-18-3]+TX, Methasulfocarb [66952-49-6]+TX, Metrafenone [220899-03-6]+TX, Pencycuron [66063-05-6]+TX, Phthalide [27355-22-2]+TX, Polyoxins [11113-80-7]+TX, Probenazole [27605-76-1]+TX, Propamocarb [25606-41-1]+TX, Proquinazid [189278-12-4]+TX, Pyroquilon [57369-32-1]+TX, Quinoxyfen [124495-18-7]+TX, Quintozene [82-68-8]+TX, Schwefel [7704-34-

9]+TX, Tiadinil [223580-51-6]+TX, Triazoxide [72459-58-6]+TX, Tricyclazole [41814-78-2]+TX, Triforine [26644-46-2]+TX, Validamycin [37248-47-8]+TX, Zoxamide (RH7281) [156052-68-5]+TX, Mandipropamid [374726-62-2]+TX, the compound of formula F-1

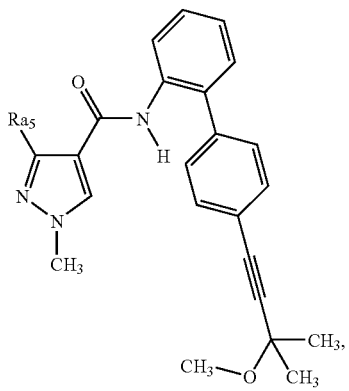
(F-1)

wherein $Ra_5$ is trifluoromethyl or difluoromethyl (WO2004/058723)+TX, the compound of formula F-2

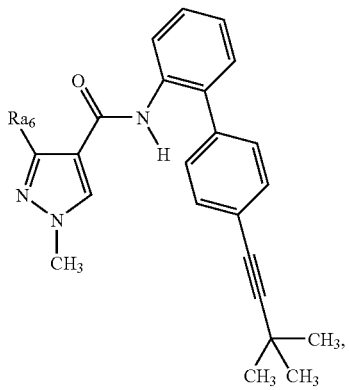
(F-2)

wherein $Ra_6$ is trifluoromethyl or difluoromethyl (WO2004/058723)+TX, the racemic compound of formula F-3 (syn)

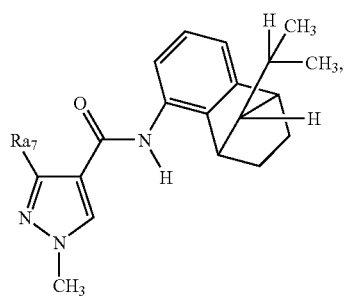
(F-3)

wherein $Ra_7$ is trifluoromethyl or difluoromethyl (WO2004/035589)+TX, the racemic mixture of formula F-4 (anti)

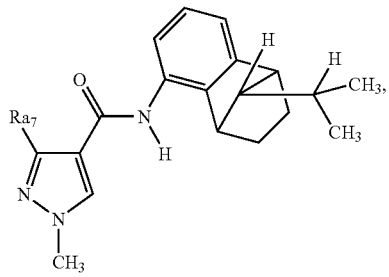
(F-4)

wherein $Ra_7$ is trifluoromethyl or difluoromethyl (WO2004/035589)+TX, the compound of formula F-5

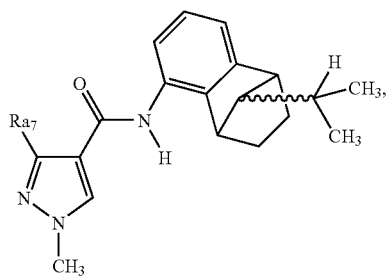
(F-5)

which is an epimeric mixture of racemic compounds of formulae F-3 (syn) and F-4 (anti), wherein the ratio from racemic compounds of formula F-3 (syn) to racemic cmpounds of formula F-4 (anti) is from 1000:1 to 1:1000 and wherein $Ra$, is trifluoromethyl or difluoromethyl (WO2004/035589)+TX, the compound of formula F-6

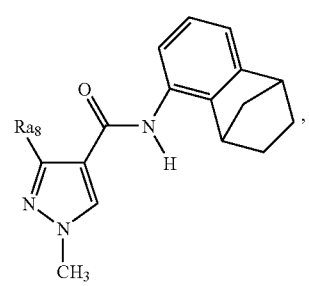
(F-6)

wherein $Ra_8$ is trifluoromethyl or difluoromethyl (WO2004/035589)+TX, the racemic compound of formula F-7 (trans)

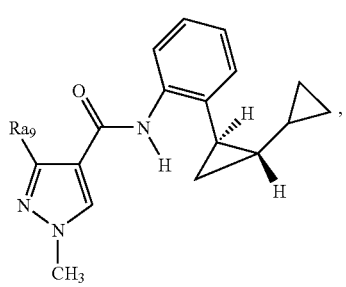
(F-7)

wherein Ra₉ is trifluoromethyl or difluoromethyl (WO03/074491)+TX, the racemic compound of formula F-8 (cis)

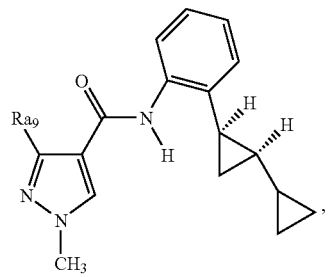
(F-8)

wherein Ra₉ is trifluoromethyl or difluoromethyl (WO03/074491)+TX, the compound of formula F-9

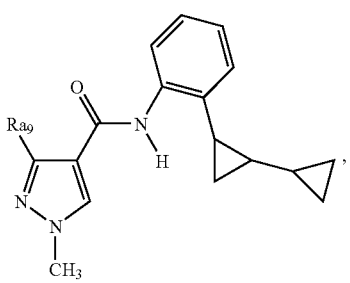
(F-9)

which is a mixture of the racemic compounds of formulae F-7 (trans) and F-8 (cis), wherein the ratio of the racemic compound of formula F-7 (trans) to the racemic compound of formula F-8 (cis) is 2:1 to 100:1; and wherein Ra₉ is trifluoromethyl or difluoromethyl (WO03/074491)+TX, the compound of formula F-10

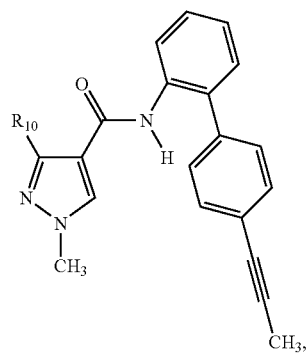
(F-10)

wherein R₁₀ is trifluoromethyl or difluoromethyl (WO2004/058723)+TX, the racemic compound of formula F-11 (trans)

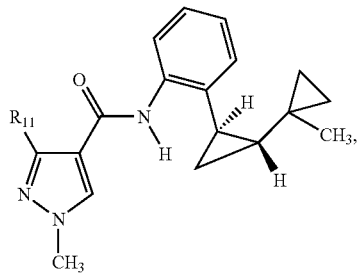
(F-11)

wherein R₁₁ is trifluoromethyl or difluoromethyl (WO03/074491)+TX, the racemic compound of formula F-12 (cis)

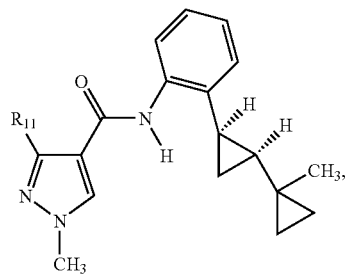
(F-12)

wherein R₁₁ is trifluoromethyl or difluoromethyl (WO03/074491)+TX, the compound of formula F-13

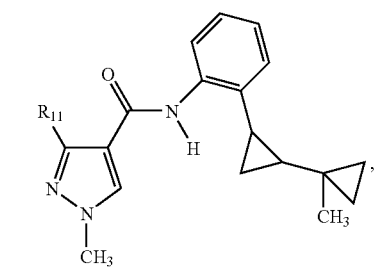
(F-13)

which is a racemic mixture of formulae F-11 (trans) and F-12 (cis), and wherein R₁₁ is trifluoromethyl or difluoromethyl (WO 03/074491)+TX, the compound of formula F-14

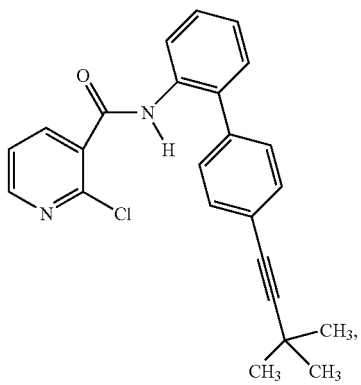
(F-14)

(WO2004/058723)+TX, and the compound of formula F-15

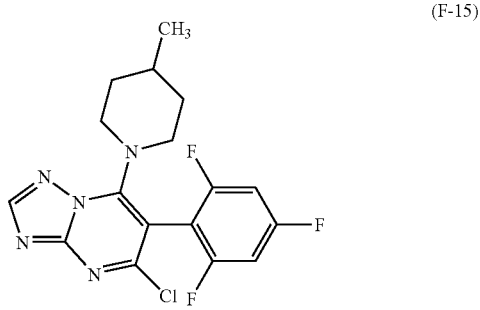 [SMILES: CC1CCN(c2c(-c3c(F)cc(F)cc3F)c(Cl)nc3ncnn23)CC1]

(F-15)

[214706-53-3]+TX.

The references in brackets behind the active ingredients, e.g. [3878-19-1] refer to the Chemical Abstracts Registry number. The compouds of the formulae A-1 to A-26 are described in WO 03/015518 or in WO 04/067528. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright©1995-2004]; for example, the compound "acetoprole" is described under the internet address http://www.alanwood.net/pesticides/acetoprole.htmL.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from tables T1 to T99 with active ingredients described above comprises a compound selected from tables T1 to T99 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures comprising a compound of formula I selected from tables T1 to T99 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from tables T1 to T99 and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

Biological Examples

%=Percent by Weight, Unless Otherwise Specified

Example B1

Activity Against *Spodoptera littoralis* (Egyptian Cotton Leafworm)

(Larvicide, Feeding/Residual Contact Activity, Preventive)

Cotton leaf discs are placed on agar in a 24-well microtiter plate and sprayed with test solutions. After drying, the leaf discs are infested with 5 $L_1$ larvae. The samples are checked for mortality, repellent effect, feeding behaviour, and growth regulation 3 days after treatment. In this test, compounds listed in Table P above show good activity. In particular compounds P.1, P.2, P.3, P.4, P.5, P.6, P.7, P.9, P.10, P.11, P.12, P.13, P.15, P.16, P.17, P.18, P.19, P.20, P.21, P.22, P.23, P.24, P.25, P.26, P.27, P.28, P.29, P.30, P.31, P.32, P.33, P.34, P.35, P.36, P.37, P.38, P.39, P.40, P.41, P.42, P.43, P.44, P.45, P.46, P.47, P.48, P.49, P.50, P.51, P.52, P.53, P.54, P.55, P.56, P.57, P.58, P.59, P.60, P.61, P.63, P.64, P.67, P.68 and P.70 show an activity of over 80% at a concentration of 400 ppm.

Example B2

Activity Against *Heliothis virescens* (Tobacco Budworm)

(Ovo-Larvicide, Feeding/Contact Activity, Curative)

Eggs (0-24 h old) are placed in 24-well microtiter plate on artificial diet and treated with test solutions by pipetting. After an incubation period of 4 days, samples are checked for egg mortality, larval mortality, and growth regulation.

In this test, compounds listed in Table P above show good activity. In particular compounds P.1, P.2, P.3, P.4, P.5, P.6, P.7, P.9, P.10, P.11, P.12, P.13, P.15, P.16, P.17, P.18, P.19, P.20, P.21, P.22, P.23, P.25, P.26, P.27, P.28, P.29, P.30, P.31, P.32, P.33, P.34, P.35, P.36, P.37, P.38, P.39, P.40, P.41, P.42, P.43, P.44, P.46, P.47, P.48, P.49, P.50, P.51, P.52, P.53, P.54, P.55, P.56, P.57, P.58, P.59, P.60, P.61, P.63, P.64, P.67, P.68, P.69, P.70, P.71, P.72, P.74, P.77 and P.78 show an activity of over 80% at a concentration of 400 ppm.

Example B3

*Plutella xylostella* (Diamond Back Moth)

(Larvicide, Feeding/Residual Contact Activity, Preventive)

24-well microtiter plate (MTP) with artificial diet is treated with test solutions by pipetting. After drying, the MTP's are infested with larvae (L2)(10-15 per well). After an incubation period of 5 days, samples are checked for larval mortality, antifeedant and growth regulation. In this test, compounds listed in Table P above show good activity. In particular compounds P.1, P.2, P.3, P.4, P.5, P.6, P.7, P.9, P.10, P.11, P.12, P.13, P.15, P.16, P.17, P.18, P.19, P.20, P.21, P.22, P.23, P.25, P.26, P.27, P.28, P.29, P.30, P.31, P.32, P.33, P.34, P.35, P.36, P.37, P.38, P.39, P.40, P.41, P.42, P.43, P.44, P.46, P.47, P.48, P.49, P.50, P.51, P.52, P.53, P.54, P.55, P.56, P.57, P.58, P.59, P.60, P.61, P.63, P.64, P.67, P.68, P.69 P.70, P.72, P.74, P.77, P78 and P.79 show an activity of over 80% at a concentration of 400 ppm.

Example B4

*Diabrotica balteata* (Corn Root Worm)

(Larvicide, Feeding/Residual Contact Activity, Preventive)

24-well microtiter plate (MTP) with artificial diet is treated with test solutions by pipetting. After drying, the MTP's are infested with larvae (L2)(6-10 per well). After an incubation period of 5 days, samples are checked for larval mortality, antifeedant and growth regulation. In this test, compounds listed in Table P above show good activity. In particular compounds P.1, P.2, P.5, P.6, P.10, P.11, P.12, P.13, P.15, P.16, P.17, P.18, P.19, P.24, P.25, P.27, P.28, P.29, P.30, P.31, P.33, P.34, P.35, P.37, P.38, P.39, P.42, P.43, P.44, P.45, P.46, P.47, P.48, P.49, P.50, P.52, P.53, P.65, P.67, P.68, P.69, P.70, P.71, P.72, P.75, P.78, and P.79 show an activity of over 80% at a concentration of 400 ppm.

Example B5

Activity Against *Myzus persicae* (Green Peach Aphid)

(Mixed Population, Feeding/Residual Contact Activity, Preventive)

Sunflower leaf discs are placed on agar in a 24-well microtiter plate and sprayed with test solutions. After drying, the leaf discs are infested with an aphid population of mixed ages. After an incubation period of 6 days, samples are checked for mortality and special effects (e.g. phytotoxicity).

In this test, compounds listed in Table P above show good activity. In particular compounds P.2, P.9, P.10, P.11, P.12, P.13, P.15, P.16, P.17, P.18, P.19, P.25, P.27, P.28, P.29, P.30, P.31, P.32, P.33, P.34, P.35, P.36, P.37, P.38, P.39, P.40, P.41, P.42, P.43, P.44, P.45, P.46, P.47, P.48, P.49, P.50, P.51, P.52, P.53, P.54, P.55, P.56, P.57, P.58, P.59, P.60, P.61 and P.70 show an activity of over 80% at a concentration of 400 ppm.

Example B6

Activity Against *Myzus persicae* (Green Peach Aphid)

(Mixed Population, Systemic/Feeding Activity, Curative)

Roots of pea seedlings, infested with an aphid population of mixed ages, are placed directly in the test solutions. 6 days after introduction, samples are checked for mortality and special effects on the plant.

In this test, compounds listed in Table P above show good activity. In particular compounds P.10, P.12, P.13, P.15, P.17, P.19, P.27, P.28, P.29, P.30, P.32, P.33, P.34, P.35, P.36, P.37, P.39, P.40, P.42, P.43, P.44, P.45, P.46, P.47, P.48, P.49, P.50, P.51, P.52, P.53, P.54, P.55, P.56, P.57, P.58, P.59, P.60, P.61, P.65, P.70 and P.71 show an activity of over 80% at a concentration of 400 ppm.

Example B7

Activity Against *Thrips tabaci* (Onion *Thrips*)

(Mixed Population, Feeding/Residual Contact Activity, Preventive)

Sunflower leaf discs are placed on agar in a 24-well microtiter plate and sprayed with test solutions. After drying, the leaf discs are infested with a thrips population of mixed ages.

After an incubation period of 6 days, samples are checked for mortality and special effects (e.g. phytotoxicity).

In this test, compounds listed in Table P above show good activity. In particular compounds P.3, P.10, P.12, P.13, P.16, P.18, P.25, P.26, P.27, P.28, P.29, P.32, P.33, P.34, P.35, P.37, P.39, P.40, P.41, P.42, P.43, P.44, P.45, P.46, P.47, P.48, P.49, P.50, P.51, P.52, P.53, P.54, P.55, P.56, P.57, P.58, P.59, P.63, P.64, P.65, P.67, P.68, P.70 and P.71 show an activity of over 80% at a concentration of 400 ppm.

Example B8

Activity Against *Cydia pomonella* (Codling Moth)

Standard *Cydia* diet cubes (1.5 cm width) are pierced with a tooth-pick and are immersed in liquid paraffin (ca. 80° C.). After the paraffin coat has hardened, an aqueous emulsion containing 400 ppm of active ingredient is applied using a De Vilbis sprayer (25 ml, 1 bar). After the spray coating has dried, the cubes are put into plastic containers which are then populated with two freshly hatched *Cydia pomonella* ($1^{st}$ instar). The containers are then closed with a plastic cap. After 14 days incubation at 26° C. and 40-60% relative humidity, the survival rate of the caterpillars as well as their growth regulation is determined. In this test, compounds listed in Table P above show good activity. In particular compounds P.10, P.11, P.12, P.18, P.19, P.20, P.29, P.30, P.31, P.32, P.33, P.34, P.35, P.37, P.38, P.39, P.42, and P.43 show an activity of over 80% at a concentration of 400 ppm.

Example B9

Activity Against *Frankliniella occidentalis* (Western Flower Thrips)

Bean leaf discs on agar in petri dishes or bean plants in a spray chamber are treated with diluted test solutions. After drying leaf discs are cut and placed in plastic cups on the surface of an agar layer and infested with mixed population. 6 days (leaf discs) or 14 days (plants) after the infestation, samples are checked for reduction of treated population and compared to the non treated population.

In this test, compounds listed in Table P above show good activity. In particular compounds P.10, P.11, P.12, P.13, P.15, P.17, P.18, P.19, P.22, P.27, P.28, P.30, P.33, P.34, P.35, P.38, P.39, P.40, P.41, P.42, P.43, P.44, P.45, P.46, P.47, P.48, P.49, P.52, P.54, P.56, P.60, P.61 and P.70 show an activity of over 80% at a concentration of 400 ppm.

Example B9

Activity Against *Bemisia tabaci* (Tobacco White Fly)

(Larvicide, Contact/Feeding)
Bean plants are infested with 20-30 adults that removed after a 4 day egg-laying period. After another 7 days, bean plants with hatched nymphs (N-2) are treated (2 replicates) with the test solutions in a spray chamber. Three weeks later, samples are checked for number of emerged adults. Efficacy was calculeted by comparing number of emerged adults in treated and non treated samples.

In this test, compounds listed in Table P above show good activity. In particular compounds P.10, P.12, P.18, P.19, P.29, P.30 and P.33 show an activity of over 80% at a concentration of 400 ppm.

Example B9

Activity Against *Nilaparvata lugens* (Brown Rice Planthopper)

(Larvicide, Feeding/Contact)
Rice seedlings are treated with the diluted test solutions in a spray chamber. After drying, they are infested with 20 $N_3$ nymphs (2 replicates). 6-12 days after the treatment samples are checked for mortality, growth regulation, and effects on the $F_1$ generation.

In this test, compounds listed in Table P above show good activity. In particular compounds P.27, P.28, P.40, P.42, P.43, P.45 and P.47 show an activity of over 80% at a concentration of 400 ppm.

Example B10

Activity Against *Aphis craccivora* (Pea Aphid)

(Mixed Population, Contact/Feeding)
Pea seedlings, infested with an aphid population of mixed ages, are treated (2 replicates) with diluted test solutions in a spray chamber. 6 days after treatment, samples are checked for mortality.

In this test, compounds listed in Table P above show good activity. In particular compounds P.10, P.27, P.28, P.30, P.40, P.42, P.43, P.44, P.46, P.47 and P.49, show an activity of over 80% at a concentration of 400 ppm.

Example B11

Activity Against *Aphis craccivora* (Pea Aphid)

(Mixed Population, Systemic/Feeding)
Roots of pea seedlings, infested with an aphid population of mixed ages, are placed (2 replicates) directly in the test solution. 6 days later, samples are checked for mortality.

In this test, compounds listed in Table P above show good activity. In particular compounds P.10, P.13, P.27, P.28, P.30, P.33, P.39, P.40, P.42, P.43, P.44, P.45, P.46, P.47, P.49, P.52, P.54, P.56, P.60 and P.61 show an activity of over 80% at a concentration of 400 ppm.

Example B12

Activity Against *Aphis qossvpii* (Cotton Aphid)

(Mixed Population, Contact/Feeding)
Pea seedlings, infested with an aphid population of mixed ages, are treated (2 replicates) with diluted test solutions in a spray chamber. 6 days after treatment, samples are checked for mortality.

In this test, compounds listed in Table P above show good activity. In particular compounds P.10, P.27, P.40, P.42 and P.47 show an activity of over 80% at a concentration of 400 ppm.

Example B13

Activity Against *Aphis aossypii* (Cotton Aphid)

(Mixed Population, Systemic/Feeding)
Roots of pea seedlings, infested with an aphid population of mixed ages, are placed (2 replicates) directly in the test solution. 6 days later, samples are checked for mortality.

In this test, compounds listed in Table P above show good activity. In particular compounds P.27, P.28, P.30, P.39, P.40, P.42, P.43, P.44, P.47, P.56, P.60 and P.61 show an activity of over 80% at a concentration of 400 ppm.

Example B14 to B15

Comparison of the Insecticidal Activity of Compounds According to the Invention with the Structurally Most Closely Comparable Compound from the State of the Art (Compound No. T81.3 Described on Page 67 of WO2005/085234)

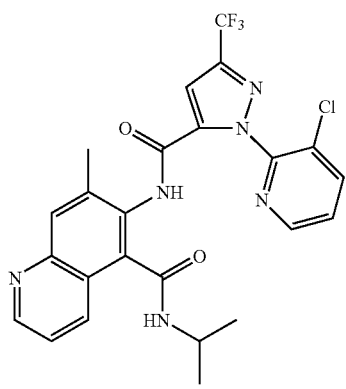

(Compound No. P.78 according to the invention)

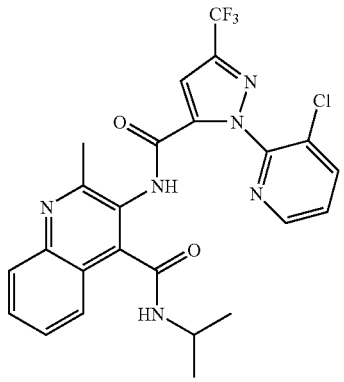

(Compound No. T81.3 according to state of the art)

Example B14

*Plutella xylostella* (Diamond Back Moth)

(Larvicide, Feeding/Residual Contact Activity, Preventive)

24-well microtiter plate (MTP) with artificial diet is treated with test solutions by pipetting. After drying, the MTP's are infested with larvae (L2) (10-15 per well). After an incubation period of 5 days, samples are checked for larval mortality, antifeedant and growth regulation.

Results are shown in Table B14:

TABLE B14

Activity against *Plutella xylostella* (diamond back moth):

| Compound: | Concentration (ppm) | Death rate (%) after 5 days |
|---|---|---|
| Comp. T81.3 (state of the art) | 50 | 100 |
| Comp. T81.3 (state of the art) | 12.5 | 60 |
| Comp. T81.3 (state of the art) | 3.1 | 0 |
| Comp. T81.3 (state of the art) | 0.8 | 0 |
| Comp. P.78 (invention) | 50 | 100 |
| Comp. P.78 (invention) | 12.5 | 100 |
| Comp. P.78 (invention) | 3.1 | 100 |
| Comp. P.78 (invention) | 0.8 | 50 |

Table B14 shows that compound No. P.78 according to the invention exerts a substantially better insecticidal action on *Plutella xylostella* than the compound from the state of the art. Especially at low application rates (12.5, 3.1 and 0.8 ppm) the compound according to the invention is far superior to the compound of the state of the art. This enhanced effect was not to be expected on the basis of the structural similarity of these compounds.

Example B15

Activity Against *Heliothis virescens* (Ovo-Larvicide Test)

Eggs (0-24 h old) are placed in 24-well microtiter plate on artificial diet and treated with test solutions by pipetting. After an incubation period of 4 days, samples are checked for egg mortality, larval mortality, and growth regulation.

Results are shown in Table B15:

TABLE B15

Activity Activity against *Heliothis virescens* (ovo-larvicide test):

| Compound: | Concentration (ppm) | Ovo-larvicidal activity (%) after 4 days |
|---|---|---|
| Comp. T81.3 (state of the art) | 50 | 80 |
| Comp. T81.3 (state of the art) | 12.5 | 65 |
| Comp. T81.3 (state of the art) | 3.1 | 25 |
| Comp. T81.3 (state of the art) | 0.8 | 0 |
| Comp. P.78 (invention) | 50 | 80 |
| Comp. P.78 (invention) | 12.5 | 80 |
| Comp. P.78 (invention) | 3.1 | 50 |
| Comp. P.78 (invention) | 0.8 | 50 |

Table B15 shows that compound No. P.78 according to the invention exerts a substantially better insecticidal action on *Heliothis virescens* than the compound from the state of the art. Especially at low application rates (12.5, 3.1 and 0.8 ppm) the compound according to the invention is far superior to the compound of the state of the art. This enhanced effect was not to be expected on the basis of the structural similarity of these compounds.

What is claimed is:

1. A compound represented by formula T24:

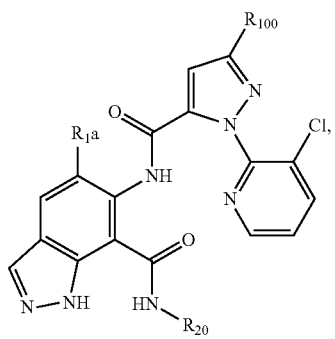
(T24)

wherein $R_{1a}$ is hydrogen, $C_1$-$C_4$alkyl, $C_2$-$C_4$alkynyl, halogen or cyano;

$R_{20}$ is hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl, thiethan-3-yl, thiethan-3-yl substituted by $C_1$-$C_4$alkyl,

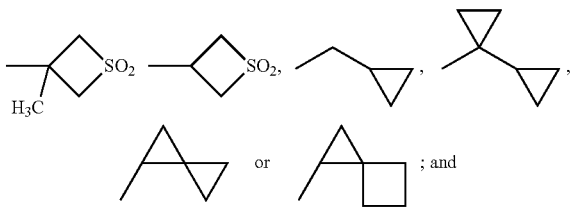

$R_{100}$ is halogen, $C_1$-$C_6$alkyl, $C_1$-$C_6$haloalkyl, $C_1$-$C_6$alkoxy or $C_1$-$C_6$haloalkoxy.

2. A compound according to claim 1, wherein $R_{1a}$ is chloro or methyl;

$R_{20}$ is hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl,

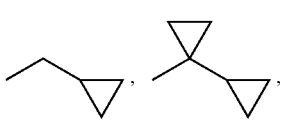

$R_{100}$ is trifluoromethyl, difluoromethyl, methoxy, bromo, chloro or 2,2,2-trifluoroethoxy.

3. A compound according to claim 2, wherein $R_{1a}$ is methyl;

$R_{20}$ is $C_1$-$C_6$alkyl; and $R_{100}$ is methoxy.

4. Treated plant propagation material wherein said plant propagation material is treated with a pesticidal composition that includes the compound of claim 1.

5. Treated plant propagation material wherein said plant propagation material is treated with a pesticidal composition that includes the compound of claim 2.

6. Treated plant propagation material wherein said plant propagation material is treated with a pesticidal composition that includes the compound of claim 3.

7. A pesticidal composition comprising the compound of claim 1 and optionally one or more auxiliaries.

8. A pesticidal composition comprising the compound of claim 2 and optionally one or more auxiliaries.

9. A pesticidal composition comprising the compound of claim 3 and optionally one or more auxiliaries.

10. A method for controlling insect or Acarina pests, which comprises applying a pesticidal composition to the pests or their environment wherein the composition comprises the compound of claim 1.

11. A method for controlling insect or Acarina pests, which comprises applying a pesticidal composition to the pests or their environment wherein the composition comprises the compound of claim 2.

12. A method for controlling insect or Acarina pests, which comprises applying a pesticidal composition to the pests or their environment wherein the composition comprises the compound of claim 3.

13. A method of protecting plant propagation material from the attack by insect or Acarina pests, which comprises treating said plant propagation material or the area surrounding said propagation material with a pesticidal composition comprising the compound of claim 1.

14. A method of protecting plant propagation material from the attack by insect or Acarina pests, which comprises treating said plant propagation material or the area surrounding said propagation material with a pesticidal composition comprising the compound of claim 2.

15. A method of protecting plant propagation material from the attack by insect or Acarina pests, which comprises treating said plant propagation material or the area surrounding said propagation material with a pesticidal composition comprising the compound of claim 3.

* * * * *